US010577625B2

(12) United States Patent
Messier

(10) Patent No.: US 10,577,625 B2
(45) Date of Patent: *Mar. 3, 2020

(54) DIRIGENT GENE EG261 AND ITS ORTHOLOGS AND PARALOGS AND THEIR USES FOR PATHOGEN RESISTANCE IN PLANTS

(71) Applicant: EG Crop Science, Inc., Longmont, CO (US)

(72) Inventor: Walter Messier, Longmont, CO (US)

(73) Assignee: EG Crop Science, Inc., Longmont, CO (US)

(*) Notice: Subject to any disclaimer, the term of this patent is extended or adjusted under 35 U.S.C. 154(b) by 112 days.

This patent is subject to a terminal disclaimer.

(21) Appl. No.: 15/800,179

(22) Filed: Nov. 1, 2017

(65) Prior Publication Data

US 2018/0265889 A1 Sep. 20, 2018

Related U.S. Application Data

(63) Continuation of application No. 13/901,071, filed on May 23, 2013, now Pat. No. 9,834,783.

(60) Provisional application No. 61/789,463, filed on Mar. 15, 2013, provisional application No. 61/652,029, filed on May 25, 2012.

(51) Int. Cl.
C12N 15/82 (2006.01)
C07K 14/415 (2006.01)

(52) U.S. Cl.
CPC ........ *C12N 15/8285* (2013.01); *C07K 14/415* (2013.01); *C12N 15/8218* (2013.01); *Y02A 40/164* (2018.01)

(58) Field of Classification Search
CPC .................................................. C12N 15/8285
See application file for complete search history.

(56) References Cited

U.S. PATENT DOCUMENTS

| | | | |
|---|---|---|---|
| 5,501,967 A | 3/1996 | Offringa et al. | |
| 7,569,389 B2 | 8/2009 | Feldmann et al. | |
| 7,842,850 B2 | 11/2010 | Singh | |
| 8,586,363 B2 | 11/2013 | Voytas et al. | |
| 8,710,300 B2 | 4/2014 | Messier | |
| 9,605,274 B2 | 3/2017 | Messier | |
| 9,834,783 B2 | 12/2017 | Messier | |
| 2004/0031072 A1* | 2/2004 | La Rosa | C07H 21/04 800/278 |
| 2007/0277269 A1 | 11/2007 | Alexandrov et al. | |
| 2009/0100537 A1 | 4/2009 | Concibido et al. | |
| 2011/0247096 A1* | 10/2011 | McCaig | C12N 15/8227 800/279 |
| 2012/0060240 A1 | 3/2012 | Lightfoot et al. | |
| 2012/0131693 A1 | 5/2012 | Bai et al. | |
| 2012/0260368 A1 | 10/2012 | Mitchum et al. | |
| 2013/0318652 A1 | 11/2013 | Messier | |
| 2014/0068807 A1 | 3/2014 | Messier | |
| 2014/0380518 A1 | 12/2014 | Messier | |

FOREIGN PATENT DOCUMENTS

| | | |
|---|---|---|
| WO | WO 2008/153804 A2 | 12/2008 |
| WO | WO 2009/021153 A2 | 2/2009 |
| WO | WO 2013/177376 A2 | 11/2013 |

OTHER PUBLICATIONS

Bourque, et al., "Suppression of gene expression in plant cells utilizing antisense sequences transcribed by RNA polymerase III." Plant Molecular Biology (1992); 19: 641-647.
Chen, et al., "The Soybean Cyst Nematode." U. Minnesota Extension Service Distribution Center (2001); F0-03935-S. pp. 1-8.
Concibido, et al., "A Decade of QTL Mapping for Cyst Nematode Resistance in Soybean." Crop Science (2004); 44: 1121-1131.
Hernandez-Garcia and Finer. "Identification and validation of promoters and cis-acting regulatory elements." Plant Science (2014); 217-218: 109-119.
Lam, Hon-Ming, et al., "Resequencing of 31 wild and cultivated soybean genomes identifies patterns of genetic diversity and selection." Nature Genetics (2010); 42(12): 1053-1062.
Komarnytsky and Borisjuk. "Functional analysis of promoter elements in plants." Genetic Engineering (2003); 25: 113-141, 29 pages.
PCT/US13/42382, Invitation to Pay Additional Fees dated May 30, 2013, 2 pages.
PCT/US13/42382, International Preliminary Report on Patentability dated May 19, 2015, 17 pages.
PCT/US13/42382, International Search Report dated Mar. 3, 2014, 7 pages.
PCT/US13/42382, Written Opinion dated Mar. 3, 2014, 16 pages.
Topping and Lindsey, "Promoter Trap Markers Differentiate Structural and Positional Components of Polar Development in *Arabidopsis*." The Plant Cell (1997); 9: 1713-1725.
Xu, et al., "Differentially Expressed Genes of Soybean During Infection by Phytophthora sojae." Journal of Integrative Agriculture (2012); 11 (3): 368-377.
Yue, et al., "Mapping Resistance to Multiple Races of Heterodera Glycines in Soybean PI 89772." Crop Science (2001); 41 (5): 1589-1595.
Yue, et al., "Genetic analysis of resistance to soybean cyst nematode in PI 438489B." Euphytica (2000); 116: 181-186.
Zeevi, et al., "Zinc Finger Nuclease and Homing Endonuclease-Mediated Assembly of Multigene Plant Transformation Vectors." Plant Physiology (2012); 158: 132-144.
Zhang, et al., "Gene Expression of Soybean During Infection by Phytophthora sojae." Genbank. May 30, 2011. Accession No. HQ993047.

* cited by examiner

*Primary Examiner* — Weihua Fan
(74) *Attorney, Agent, or Firm* — Cooley LLP

(57) ABSTRACT

The present invention provides the identification and use of EG261, homologs of EG261, orthologs of EG261, paralogs of EG261, and fragments and variations thereof for altering, e.g. increasing, pathogen tolerance and/or resistance in plants.

20 Claims, 5 Drawing Sheets

Specification includes a Sequence Listing.

Figure 2.

```
SEQ_ID_NO_9   MASHFLKSLLLLSTYALTISAEYTGFVGTLDPKSIGIHHKKTLSHFRFYWHEVFSGENPT
SEQ_ID_NO_10  MASHFLKSLLLLSTYALTISAEYTGFVGTLDPKSIGIHHKKTLSHFRFYWHEVFSGENPT
SEQ_ID_NO_12  MASHFLKSLLLLSTYALTISAEYTGFVGTLDPKSIGIHHKKTLNHFRFYWHEVFSGENPT
SEQ_ID_NO_14  MASHFLKSLLLLSTYALTISAEYTGFVGTLDPKSIGIHHKKTLNHFRFYWHEVFSGENPT
SEQ_ID_NO_15  MASHFLKSLLLLSTYALTISAEYTGFVGTLDPKSIGIHHKKTLNHFRFYWHEVFSGENPT
SEQ_ID_NO_11  MASHFLKSLLLLSTYALTISAEYTGFVGTLDPKSIGIHHKKTLSHFRFYWHEVFSGENPT
SEQ_ID_NO_13  MASHFLKSLLLLSTYALTISAEYTGFVGTLDPKSIGIHHKKTLSHFRFYWHEVFSGENPT
              *********************************************.************

SEQ_ID_NO_9   SVRIIPSLPKYNATTFGSVGIFDTPLTVGPEVYSKVVGKAEGLFASTSQTQFDLLLIYN
SEQ_ID_NO_10  SVRIIPSLPKYNATTFGSVGIFDTPLTVGPEVYSKVVGKAEGLFASTSQTQFDLLLIYN
SEQ_ID_NO_12  SVRIIPSLPKYNTTTFGSVGISDNALTVGPEVYSKVVGKAEGLFVSTSQTQFDLLLIYN
SEQ_ID_NO_14  SVRIIPSLPKYNTTTFGSVGISDNALTVGPEVYSKVVGKAEGLFVSTSQTQFDLLLIYN
SEQ_ID_NO_15  SVRIIPSLPKYNTTTFGSVGIFDNTLTVGPEVYSKVVGKAEGLFASTSQTQFDLLLIYN
SEQ_ID_NO_11  TVRIIPSLPKYNTTTFGSVGIFDNTLTVGPEVYSKVAGKAEGLFASTSQTQFNLLLIYS
SEQ_ID_NO_13  TVRIIPSLPKYNTTTFGSVGIFDNTLTVGPEVYSKVAGKAEGLFASTSQTQFNLLLIYS
              :***********.:***********.:.:.***********.***********:*****:

SEQ_ID_NO_9   FALTQGKYNGSTITFTGRSPLSEKVRELPIVGGSGVFKFATGYVESRTLSFDPQTRNNTV
SEQ_ID_NO_10  FALTQGKYNGSTITFTGRSPLSEKVRELPIVGGSGVFKFATGYVESRTLSFDPQTRNNTV
SEQ_ID_NO_12  FALTQGKYNGSTITFTGRSPLSEKVRELPIVGGSGVFKFSTGYVESRTLSFDPQTRNNTV
SEQ_ID_NO_14  FALTQGKYNGSTITFTGRSPLSEKVRELPIVGGSGVFKFSTGYVESRTLSFDPQTRNNTV
SEQ_ID_NO_15  FALTQGKYNGSTITFTGRSPLSEKVRELPIVGGSGVFKFSTGYYESRMLSFDPQTRNNTV
SEQ_ID_NO_11  FALTQGKYNGSTITFTGRSPLSEKVRELPIVGGSGVFKFATGYVESRTLSFDPQTRNNTV
SEQ_ID_NO_13  FALTQGKYNGSTITFTGRSPLSEKVRELPIVGGSGVFKFATGYVESRTLSFDPQTRNNTV
              ***************************************:***:***:***********

SEQ_ID_NO_9   QFDVYIYY
SEQ_ID_NO_10  QFDVYIYY
SEQ_ID_NO_12  QFDVYIYY
SEQ_ID_NO_14  QFDVYIYY
SEQ_ID_NO_15  QFDVYIYY
SEQ_ID_NO_11  QFDVYIYY
SEQ_ID_NO_13  QFDVYIYY
              ********
```

Figure 3.

```
SEQ_ID_NO_25  Cultivated_tomato       ----------------MAKLILQIFTISLFLSLVAFRATGEEDNYIFGKSIN
SEQ_ID_NO_27  Solanum_chmielewskii    ----------------MAKLILQIFTISLFLSLVAFRATGEEDNYIFGKSIN
SEQ_ID_NO_28  Solanum_habrochaites    ----------------MAKLILQIFTISLFLSLVAFRATGEEDNXIFEKSIN
SEQ_ID_NO_26  Peruvian_tomato         ----------------MAKLILQIFTISLFLSLVAFRATGEEDNXIFGKSIN
SEQ_ID_NO_29  Solanum_corneliomulleri ----------------MAKLILIFTISVFLSLVAFRATGEEDNYIFGKSIN
SEQ_ID_NO_33  Potato                  ----------------MAKLILQIFTISIFLSLVAFPATGEEDTYIFGKSIN
SEQ_ID_NO_32  Eggplant                ----------------MAKLSLQIFTISILLFLVAFPATGEEDNYTFGKSIN
SEQ_ID_NO_30  Chili_pepper            ----------------MAKLILQIFSISVLYSLVAFPATGEED-HIFGKSIN
SEQ_ID_NO_31  Hot_pepper              ----------------MAKLILQIFSISVLYSLVAFPATGEED-HIFGKSIN
                                                      ***: * **:***::  **** ****** * ****

SEQ_ID_NO_25  Cultivated_tomato       KKPTRLRKEKISHFRFFWHDILSGSKPTSMMIIPPPKNTTTGFGQMNMID
SEQ_ID_NO_27  Solanum_chmielewskii    KKPTRLRKEKISHFRFYWHDILSGSKPTSMMIIPPPKNTTTGFGQMNMID
SEQ_ID_NO_28  Solanum_habrochaites    KKPTRLRKXKFSHFRFYWHDILSGSKPTSMMIIPPPKNTTTGFGQMNMID
SEQ_ID_NO_26  Peruvian_tomato         KKPTRLRKEKFSHFRFYWHDILSGSKPTSMMIIPPPKNTTTGFGQMNMID
SEQ_ID_NO_29  Solanum_corneliomulleri KKPTRLRKEKFSHFRFYWHDILSGSKPTSMMIIPPPKNTTTGFGQMNMID
SEQ_ID_NO_33  Potato                  KKPTRLKKEKFSHFRFYWHDILSGSKPTSMMIIPPSKNTTTGFGQMNMID
SEQ_ID_NO_32  Eggplant                KKSMRLRKEKLSHFRFYWHDVLSGSKPTSMMIIPPPKNTTTGFGQMNMID
SEQ_ID_NO_30  Chili_pepper            EKSMRLKREKLSHFRFYWHDVLSGSKPTSMIIIPPPKNTTTGFGQMNMID
SEQ_ID_NO_31  Hot_pepper              EKSMRLKREKLSHFRFYWHDVLSGSKPTSMIIIPPPKNTTTGFGQMNMID
                                      :*. **:: *:*****:***.:********.:****************

SEQ_ID_NO_25  Cultivated_tomato       NALTLGPKLSSKIVGRAQGFYGAASLNDVGLMMVMNFAFIEGKYNGSTFT
SEQ_ID_NO_27  Solanum_chmielewskii    NALTLGPKLSSKIVGRAQGFYGAASLNDVGLMMVMNFAFIEGKYNGSTFT
SEQ_ID_NO_28  Solanum_habrochaites    NALTLGPKLSSKIVGRAQGFYGAASLNDVGLMMVMNFAFIEGKYNGSTFT
SEQ_ID_NO_26  Peruvian_tomato         NALTLGPKLSSKIVGRAQGFYGAASLNDVGLMMVMNFAFIEGKYNGSTFT
SEQ_ID_NO_29  Solanum_corneliomulleri NALTLGPKLSSKIVGRAQGFYGAASLNDVGLMMVMNFAFIEGKYNGSTFT
SEQ_ID_NO_33  Potato                  NALTLGPELSSKIVGRAQGFYGAASLNDVGLMMVMNFAFIEGKYNGSTFT
SEQ_ID_NO_32  Eggplant                NALTLGAELSSKIVGRAQGFYAAASLNDVGLMMVMNFAFIEGKYNGSTFT
SEQ_ID_NO_30  Chili_pepper            NALTLGPELSSRIVGRAQGFYAAASLNDVGLMMVMNFAFIEGKYNGSTFT
SEQ_ID_NO_31  Hot_pepper              NALTLGPELSSRIVGRAQGFYAAASLNDVGLMMVMNFAFIEGKYNGSTFT
                                      ******.:****.*******.************************** 
```

Figure 3. Continued

```
SEQ_ID_NO_25  Cultivated_tomato       ILGRNPVFEKVREMAVIGGSGLFRFARGYVQASTHSWDFKTGDATVQYDA
SEQ_ID_NO_27  Solanum_chmielewskii    ILGRNPVFEKVREMAVIGGSGLFRFARGYVQASTHSWDFKTGDATVX---
SEQ_ID_NO_28  Solanum_habrochaites    ILGRNPVXEKVREMAVIGGSGLFRFARGYVQASTHSWDFKTGDATVQYDA
SEQ_ID_NO_26  Peruvian_tomato         ILGRNPVFEKVREMAVIGGTGLFRFARGYVEASTHSWDFKTGDATVQYDA
SEQ_ID_NO_29  Solanum_corneliomulleri ILGRNPVFEKVREMAVIGGSGLFRFARGYVEASTHSWDFKTGDATVQYDA
SEQ_ID_NO_33  Potato                  ILGRNPVFEKVREMAVIGGSGLFRFARGYVEASTHSWDFKTGDATVQYDA
SEQ_ID_NO_32  Eggplant                ILGRNPVFEKVREMAVIGGSGLFRFARGYVQASTHSWDYKTGDATVKYDA
SEQ_ID_NO_30  Chili_pepper            ILGRNPVFEKVREMAVIGGSGLFRFARGYVQASTHSLDFKTGDATVQYDA
SEQ_ID_NO_31  Hot_pepper              ILGRNPVFEKVREMAVIGGSGLFRFARGYVQASTHSLDFKTGDATVQYDA
                                      *******  ***************:***************  ********

SEQ_ID_NO_25  Cultivated_tomato       YVFALLRFTNFIYFHRVNLX------
SEQ_ID_NO_27  Solanum_chmielewskii    --------------------------
SEQ_ID_NO_28  Solanum_habrochaites    YVLHY---------------------
SEQ_ID_NO_26  Peruvian_tomato         YVLHY---------------------
SEQ_ID_NO_29  Solanum_corneliomulleri YVLHY---------------------
SEQ_ID_NO_33  Potato                  YVLHYG-FTNFVCFRCVNFIRFSLTGY
SEQ_ID_NO_32  Eggplant                X-------------------------
SEQ_ID_NO_30  Chili_pepper            YVLHY---------------------
SEQ_ID_NO_31  Hot_pepper              YVLHY---------------------
```

Figure 4.

```
SEQ ID NO: 51   maize     MAAAVPLLLLLLPTTLMAASAASGGEKSTHIKLYWHDVVSGPS-PTAVPVAQAAVTNTS     59
SEQ ID NO: 53   rice      ------------------ETTAT----TTHIKVYWHDVVSGPS-PTAVQVARAATTNSS    36
SEQ ID NO: 54   wheat     -MAS-AVLFVLLALATMQPQTASS--QKETHLKVYWHDVVSGPD-PTSVFVARATTTNTS    55
SEQ ID NO: 55   barley    -MASAALFFVLLALATMLPQTASS--EKETHLKVYWHDVVSGPN-PTSVPVARAATTNTS    56
SEQ ID NO: 52   sorghum   -MATTLFLLLCAAAALASAAAAADDTGFTTFKLYFHDIVAGTSSPTAVRIAQAASSNTS    59
                              :   * :*:*:**:.*..  **:* **:..*

SEQ ID NO: 51   maize     KTAFGMVVVIDDPLTEGPDLKSSKPLGRAQGTYVGAGKDELSLMMNMNFVFQAGEYNGST   119
SEQ ID NO: 53   rice      ASFFGAVVVIDDPLTSGPDLNASSPVGRAQGTYVSAGKDTVALLMNMNFVFQSGRYNGST    96
SEQ ID NO: 54   wheat     KTAFGVVMVMDNSLTEGPSLNSSRLMGRAQGTYIAAGKDQLALLMLMNFLFTAGKYNGSS   115
SEQ ID NO: 55   barley    KTAFGVVMVIDNPLTEGGSLNSSRLMGRAQGTYIAAGKDQLALLMLMNFVFTAGEYNGSS   116
SEQ ID NO: 52   sorghum   STSFGAVVAIDDPLTTGPTRSSGTEIGRAQGTYTFADQTTFGLLMVMNFVFTAGDHNGST   119
                           ** *:*::**..**  ..  ..: .*******  * :.*   * :.**::.*  *.::

SEQ ID NO: 51   maize     VAIMGRNAVFDAVREMAVVGGTGAFRMARGYAQARTHTFDLNTGDATVEYNLYIKH-    175
SEQ ID NO: 53   rice      VAIMGRNEVFAAVREMAVVGGTGVFRWARGYAQARTHTFDMKTGDATVEYNLYINH-    152
SEQ ID NO: 54   wheat     VAIMGRNAVFTEVREMAVVGGTGVFRWAPGYAQARTHTLDLKTGDATVEYNVFIMH-    171
SEQ ID NO: 55   barley    VAIMGRNAVFTEVREMAVVGGTGVFRWARGYAQARTHTLDLKTGDATVEYKVFVMH-    172
SEQ ID NO: 52   sorghum   LSILGRNEVLTDVREMSIVGGSGKFRMAKGYVQAHTIDSGATTGETVVQYTVNVKTP   176
                          ::*:****.*:  ****:****.*:**  **.**:*: *  * ..*..*:: :  :
```

DIRIGENT GENE EG261 AND ITS ORTHOLOGS AND PARALOGS AND THEIR USES FOR PATHOGEN RESISTANCE IN PLANTS

CROSS-REFERENCE TO RELATED APPLICATIONS

This application is a Continuation Application of U.S. patent application Ser. No. 13/901,071, filed on May 23, 2013, which claims the benefit of priority to U.S. provisional application No. 61/789,463 filed on Mar. 15, 2013 and U.S. provisional application No. 61/652,029 filed on May 25, 2012 each of which is hereby incorporated by reference in their entirety for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: EVOL_004_7US_SeqList_ST25.txt, date recorded: Oct. 27, 2017, file size 84 kilobytes).

TECHNICAL FIELD

The invention relates to the identification and use of nucleic acid sequences for pathogen resistance in plants.

BACKGROUND

"Dirigent" refers to genes or proteins which are members of a gene or protein family, respectively, members of which have been identified in many plants. Dirigents have been implicated in resistance to various types of pathogens in a range of different, and sometimes distantly related, plants.

Dirigent proteins confer a broad response to many pathogens in a number of plants species, including for conifers (Ralph et al., *Plant Molecular Biology* (2006) 60:21-40); cotton (L. Zhu, X. Zhang, L. Tu, F. Zeng, Y. Nie and X. Guo *Journal of Plant Pathology*. 2007. 89 (1), 41-45); barley (Ralph et al., *Plant Molecular Biology*, 2006, 60:21-40 _DOI 10.1007/s11103-005-2226-y), barley, (Kristensen et al., *Plant Physiology*, June 1999, Vol. 120, pp. 501-512); orange trees ("Gene expression in *Citrus sinensis* (L.) Osbeck following infection with the bacterial pathogen *Candidatus Liberibacter asiaticus* causing Huanglongbing in Florida" Albrecht et al., *Plant Science*, Volume 175, Issue 3, September 2008, Pages 291-306); wheat (poster presentation: "Cloning and Transcriptional Profiling of a Dirigent-like Gene from Wheat Responding to Hessian Fy Infestation", C. Williams, Poster PO910, Plant and Animal Genome 20); and pea ("Transgenic canola lines expressing pea defense gene DRR206 have resistance to aggressive blackleg isolates and to *Rhizoctonia solanil*.", Wang and Fristensky, *Molecular Breeding* Volume 8, Number 3 (2001), 263-271, DOI: 10.1023/A:1013706400168). Thus, dirigents have been implicated in pathogen response in many plants, and this response has been shown for a number of different pathogens, including but not limited to fungi, bacteria, insects and nematodes.

The identification and use of dirigents is important to plant husbandry and crop production, particularly for commercial crop production in agronomy and horticulture.

SUMMARY OF THE INVENTION

The present invention provides the identification and use of EG261, homologs of EG261, orthologs of EG261, paralogs of EG261, and fragments and variations thereof for altering, e.g. conferring or increasing, pathogen tolerance and/or resistance in plants. Importantly, such pathogen altered, e.g., increased, tolerance and/or resistance can be obtained using conventional plant breeding methods, whereby such methods optionally also include using any of various biotechnological methods for verifying that the desired EG261, homologs of EG261, orthologs of EG261, paralogs of EG261, and fragments and variations thereof are present in the resulting crosses and offspring.

In embodiments, the present invention provides isolated nucleic acid sequences coding for EG261, homologs of EG261, orthologs of EG261, paralogs of EG261, and fragments and variations thereof. The present invention also provides chimeric genes, constructs, recombinant DNA, vectors, plant cells, plant tissues, plant parts, plant tissue cultures and/or whole plants comprising such nucleic acid sequences.

In one embodiment, the present invention provides polynucleotides for altering and/or increasing pathogen tolerance and/or resistance comprising a nucleic acid sequence that shares at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to nucleic acids coding for EG261, homologs of EG261, orthologs of EG261, paralogs of EG261, and fragments and variations thereof.

The present invention further provides isolated amino acid sequences (e.g., a peptide, polypeptide and the like) comprising an amino acid sequence encoded by the nucleic acid sequences for EG261, homologs of EG261, orthologs of EG261, paralogs of EG261, and fragments and variations thereof.

In some embodiments, the present invention provides isolated amino acid sequences which form a protein that shares an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to an amino acid sequence encoded by the nucleic acid sequences for EG261, homologs of EG261, orthologs of EG261, paralogs of EG261, and fragments and variations thereof.

In one embodiment, the present invention provides isolated amino acid sequences which form a protein that shares an amino acid having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to an amino acid sequence encoded by the nucleic acid sequences for EG261, homologs of EG261, orthologs of EG261, paralogs of EG261, and fragments and variations thereof.

The present invention also provides a chimeric gene comprising the isolated nucleic acid sequence of any one of the polynucleotides described above operably linked to suitable regulatory sequences.

The present invention also provides a recombinant construct comprising the chimeric genes as described above.

The present invention further comprises interfering RNA (RNAi) based on the expression of the nucleic acid sequences of the present invention, wherein such RNAi includes but is not limited to microRNA (miRNA) and small interfering RNA (siRNA) which can be used in gene silencing constructs.

The present invention also provides transformed host cells comprising the chimeric genes as described above. In one embodiment, said host cells are selected from the group consisting of bacteria, yeasts, filamentous fungi, algae, animals, and plants.

The present invention in another aspect provides plants comprising in its genome one or more genes as described herein, one or more genes with mutations as described herein, or the chimeric genes as described herein. In some embodiments, the plant is derived from a soybean variety sensitive to soybean cyst nematode (SCN), and wherein the gene comprises nucleic acid sequence encoding an EG261 ortholog derived from G. pescadrensis.

The present invention in another aspect provides plant seed obtained from the plants described herein, wherein the plants producing such seeds comprise in their genomes one or more genes as described herein, one or more genes with mutations as described herein, or the chimeric genes as described herein.

In some embodiments, the methods comprise introducing mutations in one or more nucleic acid sequences for EG261, homologs of EG261, orthologs of EG261, paralogs of EG261, and fragments and variations thereof.

In one aspect, the present invention provides methods of breeding plants to alter, e.g. confer or increase, pathogen tolerance and/or resistance. In one embodiment, such methods comprise making a cross between a first plant comprising one or more nucleic acid sequences for EG261, homologs of EG261, orthologs of EG261, paralogs of EG261, and fragments and variations with a second plant of the same or different species to produce an F1 plant; backcrossing the F1 plant to the second plant; and repeating the backcrossing step to generate a near isogenic line, wherein the one or more nucleic acid sequences for EG261, homologs of EG261, orthologs of EG261, paralogs of EG261, and fragments and variations thereof are integrated into the genome of the second plant; wherein the near isogenic line derived from the second plant has altered, e.g. increased, pathogen tolerance and/or resistance. Optionally, such methods can be facilitated by using various biotechnological methods to verify that the nucleic acid sequences for EG261, homologs of EG261, orthologs of EG261, paralogs of EG261, and fragments and variations thereof are included in the second plant. In some embodiments, the first plant comprises a nucleic acid sequence encoding an EG261 ortholog derived from G. pescadrensis. In some embodiments, the second plant is a soybean variety sensitive to soybean cyst nematode (SCN).

The present invention provides isolated polynucleotides comprising a nucleic acid sequence selected from the group consisting of: (a) a nucleic acid sequence having at least 95% identical nucleotides to a nucleic acid sequence coding for EG261; (b) a nucleic acid sequence having at least 95% identical nucleotides to a nucleic acid sequence coding for a homolog of EG261; (c) a nucleic acid sequence having at least 95% identical nucleotides to a nucleic acid sequence coding for an ortholog of EG261; (d) a nucleic acid sequence having at least 95% identical nucleotides to a nucleic acid sequence coding for a paralog of EG261; (e) complements of a nucleic acid sequence of (a), (b), (c) or (d); (0 reverse complements of a nucleic acid sequence of (a), (b), (c) or (d); (g) reverse sequences of a nucleic acid sequence of (a), (b), (c) or (d); and, (h) fragments and variations of a nucleic acid sequence of (a), (b), (c), (d), (e), (0 and (g).

The present invention provides vectors comprising one or more of the polynucleotides described herein.

The present invention also provides genetic constructs comprising one or more of the isolated polynucleotides described herein.

The present invention also provides genetic constructs comprising, in the 5'-3' direction: (a) a promoter sequence, (b) one or more of the isolated polynucleotides described herein; and (c) a gene termination sequence.

In some embodiments of the present invention the genetic constructs comprise an open reading frame encoding a polypeptide capable of altering pathogen tolerance and/or resistance.

In some embodiments of the present invention the pathogen tolerance and/or resistance is conferred or enhanced.

In some embodiments of the present invention the pathogen is soybean cyst nematode.

The present invention further provides transgenic cells comprising the genetic constructs described herein.

The present invention also provides organisms comprising the transgenic cells described herein.

In some embodiments of the present invention the organism is a plant. In some specific embodiments of the present invention the plant is a soybean plant.

The present invention provides plants and progeny plants thereof having altered pathogen tolerance and/or resistance as a result of inheriting the polynucleotides described herein.

The present invention provides methods of producing hybrid seed which include crossing the plants and progeny plants described herein with a different plant of the same species, and harvesting the resultant seed.

The present invention also provides methods for modifying gene expression in a target organism comprising stably incorporating into the genome of the organism a genetic construct described herein. In some such embodiments of the present invention the organism is a plant. In some specific embodiments the plant is a soybean plant.

The present invention provides methods for producing a plant having altered pathogen tolerance and/or resistance comprising: (a) transforming a plant cell with a genetic construct to provide a transgenic cell, wherein the genetic construct comprises: (i) a promoter sequence; (ii) an isolated polynucleotide sequence of the present invention as described herein; and (iii) a gene termination sequence; and (b) cultivating the transgenic cell under conditions conducive to regeneration and mature plant growth of a plant having altered pathogen tolerance and/or resistance. In some such embodiments the plant cell is a soybean plant cell.

The present invention also provides methods for modifying a phenotype of a target organism, comprising stably incorporating into the genome of the target organism a genetic construct comprising: (a) a promoter sequence; (b) an isolated polynucleotide sequence of the present invention as described herein; and (c) a gene termination sequence. In some such embodiments the target organism is a plant. In some specific embodiments the plant is a soybean plant.

The present invention provides processes of determining the presence or absence of a polynucleotide coding for EG261, homologs of EG261, orthologs of EG261, paralogs of EG261, and fragments and variations thereof in a plant, wherein the process comprises at least one of: (a) isolating nucleic acid molecules from said plant and amplifying sequences homologous to the polynucleotide; (b) isolating nucleic acid molecules from said plant and performing a Southern hybridization to detect the polynucleotide; (c) isolating proteins from said plant and performing a Western Blot using antibodies to a protein encoded by the polynucleotide; and/or (d) demonstrating the presence of mRNA sequences derived from a polynucleotide mRNA transcript and unique to the polynucleotide.

The present invention provides methods of breeding plants to produce altered pathogen tolerance and/or resistance comprising: i) making a cross between a first plant with an isolated polynucleotide sequence of claim 1 with a second plant to produce a F1 plant; ii) backcrossing the F1 plant to the second plant; and iii) repeating the backcrossing step to generate a near isogenic or isogenic line, wherein the isolated polynucleotide sequence of claim 1 is integrated into the genome of the second plant and the near isogenic or isogenic line derived from the second plant with the isolated polynucleotide sequence has conferred or enhanced pathogen tolerance and/or resistance compared to that of the second plant without the isolated polynucleotide sequence. In some such embodiments of the present invention the plant is soybean. In some such embodiments of the present invention the pathogen is soybean cyst nematode. In some embodiments, the first plant comprises a nucleic acid sequence encoding an EG261 ortholog derived from *G. pescadrensis*. In some embodiments, the second plant is a soybean variety sensitive to soybean cyst nematode (SCN).

The present invention provides methods of producing a plant with conferred or enhanced pathogen tolerance and/or resistance, the process comprising: (a) crossing a first plant containing a polynucleotide coding for EG261, homologs of EG261, orthologs of EG261, paralogs of EG261, and fragments and variations thereof to a second plant, and harvesting the resultant seed; (b) determining the presence of the polynucleotide in the resultant seed or in cells or tissues of a plant grown from the resultant seed; wherein the determining comprises at least one of: (i) isolating nucleic acid molecules from the resultant seed or in cells or tissues of a plant grown from the resultant seed and amplifying sequences homologous to the polynucleotide; (ii) isolating nucleic acid molecules from the resultant seed or in cells or tissues of a plant grown from the resultant seed and performing a Southern hybridization to detect the polynucleotide; (iii) isolating proteins from the resultant seed or in cells or tissues of a plant grown from the resultant seed and performing a Western Blot using antibodies to a protein encoded by the polynucleotide; and/or (iv) demonstrating the presence in the resultant seed or in cells or tissues of a plant grown from the resultant seed of mRNA sequences derived from a polynucleotide mRNA transcript and unique to the polynucleotide. In some such embodiments the method further comprises confirming that the resultant seed or the cells or tissues of the plant grown from the resultant seed contain the polynucleotide. In some such embodiments the methods further comprise using the resultant plant containing the polynucleotide in a plant breeding scheme. In some embodiments the methods further comprise crossing the resultant plant containing the polynucleotide with another plant of the same species. In some embodiments, the first plant comprises a nucleic acid sequence encoding an EG261 ortholog derived from *G. pescadrensis*. In some embodiments, the second plant is a soybean variety sensitive to soybean cyst nematode (SCN).

The EG261, homologs of EG261, orthologs of EG261, paralogs of EG261, and/or fragments and variations thereof of the present invention provide broad pathogen resistance in many, distantly related plant species. For example, orthologs of EG261 may be effective in a number of commercially important crop species, including, e.g., soybeans and cotton.

BRIEF DESCRIPTION OF THE DRAWINGS

FIG. 2 depicts sequence alignments of dirigent proteins encoded by the dirigent genes of SEQ ID NOs 9 to 15.

FIG. 3 depicts sequence alignments of dirigent proteins encoded by the dirigent genes of Solanaceae family plant species.

FIG. 4 depicts sequence alignments of dirigent proteins encoded by the dirigent genes of monocot plant species.

DETAILED DESCRIPTION

Definitions

Figure 1:
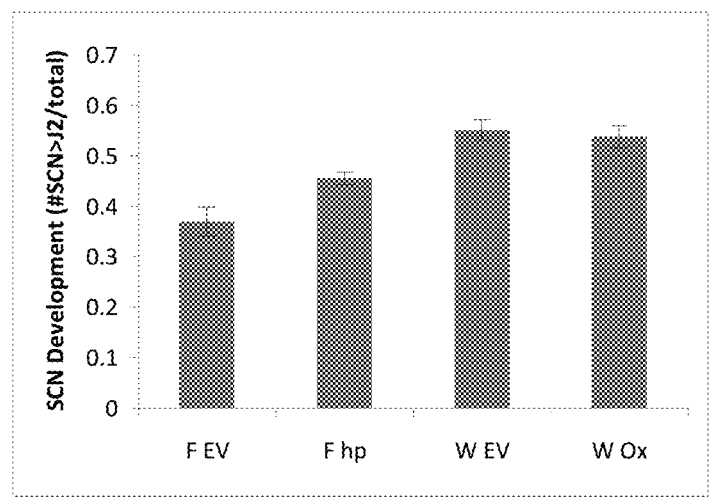
FIG. 1 depicts results showing that silencing of EG261 reduces the SCN resistance of "Fayette", a SCN-resistant variety of soybean.

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein, the verb "comprise" as is used in this description and in the claims and its conjugations are used in its non-limiting sense to mean that items following the word are included, but items not specifically mentioned are not excluded.

As used herein, the term "plant" refers to any living organism belonging to the kingdom Plantae (i.e., any genus/species in the Plant Kingdom), including but not limited to, *Glycine* spp. (e.g., soybean), Solanaceae species (e.g., *Solanum lycopersicum, Solanum chmielewskii, Solanum habrochaites, Solanum corneliomulleri, Capsicum annuum, Solanum melongena, Solanum tuberosum*), *Phaseolus vulgaris, Vigna unguiculata, Coffee arabica, Zea mays, Sorghum* spp., *Oryza sativa, Triticum* spp. *Hordeum* spp., *Gossypium hirsutum*, and *Heliotropium curassavicum*.

As used herein, the term "plant part" refers to any part of a plant including but not limited to the shoot, root, stem, seeds, fruits, stipules, leaves, petals, flowers, ovules, bracts, branches, petioles, internodes, bark, pubescence, tillers, rhizomes, fronds, blades, pollen, stamen, rootstock, scion and the like. The two main parts of plants grown in some sort of media, such as soil, are often referred to as the "above-ground" part, also often referred to as the "shoots", and the "below-ground" part, also often referred to as the "roots".

As used herein when discussing plants, the term "ovule" refers to the female gametophyte, whereas the term "pollen" means the male gametophyte.

As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

As used herein, the term "phenotype" refers to the observable characters of an individual cell, cell culture, organism (e.g., a plant), or group of organisms which results from the interaction between that individual's genetic makeup (i.e., genotype) and the environment.

As used herein, the term "nucleic acid" refers to a polymeric form of nucleotides of any length, either ribonucleotides or deoxyribonucleotides, or analogs thereof.

This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "nucleotide change" or "nucleotide modification" refers to, e.g., nucleotide substitution, deletion, and/or insertion, as is well understood in the art. For example, such nucleotide changes/modifications include mutations containing alterations that produce silent substitutions, additions, or deletions, but do not alter the properties or activities of the encoded protein or how the proteins are made. As another example, such nucleotide changes/modifications include mutations containing alterations that produce replacement substitutions, additions, or deletions, that alter the properties or activities of the encoded protein or how the proteins are made.

As used herein, the terms "polypeptide," "peptide," and "protein" are used interchangeably herein to refer to polymers of amino acids of any length. These terms also include proteins that are post-translationally modified through reactions that include glycosylation, acetylation and phosphorylation.

As used herein, the term "protein modification" refers to, e.g., amino acid substitution, amino acid modification, deletion, and/or insertion, as is well understood in the art.

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

As used herein, the term "pathogen" refers to an agent that causes disease, especially a living microorganism such as an insect, a bacterium, virus, nematode or fungus.

As used herein, the term "nematode" refers to any of several worms of the phylum Nematoda, having unsegmented, cylindrical bodies, often narrowing at each end, and including parasitic forms such as the hookworm and pinworm. They are referred to as "roundworms" in some contexts. Nematode species are very difficult to distinguish, with over 28,000 having been described. Plant-parasitic nematodes include several groups causing severe crop losses. The most common genera are *Aphelenchoides* (foliar nematodes), *Ditylenchus, Globodera* (potato cyst nematodes), *Heterodera* (soybean cyst nematodes), *Longidorus, Meloidogyne* (root-knot nematodes), *Nacobbus, Pratylenchus* (lesion nematodes), *Trichodorus* and *Xiphinema* (dagger nematodes). Several phytoparasitic nematode species cause histological damages to roots, including the formation of visible galls (e.g. by root-knot nematodes), which are useful characters for their diagnostic in the field. Some nematode species transmit plant viruses through their feeding activity on roots. One of them is *Xiphinema index*, vector of grapevine fanleaf virus), an important disease of grapes. Other nematodes attacks bark and forest trees. The most important representative of this group is *Bursaphelenchus xylophilus*, the pine wood nematode, present in Asia and America and recently discovered in Europe.

As used herein, the phrase "soybean cyst nematode" and the term "SCN" each refer to *Heterodera glycines*, a plant-parasitic nematode and a devastating pest of the soybean including *Glycine max*, worldwide. The nematode infects the roots of soybean, and the female nematode eventually becomes a cyst. Infection causes various symptoms that may include chlorosis of the leaves and stems, root necrosis, loss in seed yield and suppression of root and shoot growth. SCN has threatened the U.S. crop since the 1950s, reducing returns to soybean producers by $500 million each year and reducing yields by as much as 75 percent. It is also a significant problem in the soybean growing areas of the world, including South America and Asia.

As used herein, the term "resistant", or "resistance", describes a plant, line or cultivar that shows fewer or reduced symptoms to a biotic pest or pathogen than a susceptible (or more susceptible) plant, line or variety to that biotic pest or pathogen. These terms are variously applied to describe plants that show no symptoms as well as plants showing some symptoms but that are still able to produce marketable product with an acceptable yield. Some lines that are referred to as resistant are only so in the sense that they may still produce a crop, even though the plants may appear visually stunted and the yield is reduced compared to uninfected plants. As defined by the International Seed Federation (ISF), a non-governmental, non-profit organization representing the seed industry (see "Definition of the Terms Describing the Reaction of Plants to Pests or Pathogens and to Abiotic Stresses for the Vegetable Seed Industry", May 2005), the recognition of whether a plant is affected by or subject to a pest or pathogen can depend on the analytical method employed. Resistance is defined by the ISF as the ability of plant types to restrict the growth and development of a specified pest or pathogen and/or the damage they cause when compared to susceptible plant varieties under similar environmental conditions and pest or pathogen pressure. Resistant plant types may still exhibit some disease symptoms or damage. Two levels of resistance are defined. The term "high/standard resistance" is used for plant varieties that highly restrict the growth and development of the specified pest or pathogen under normal pest or pathogen pressure when compared to susceptible varieties. "Moderate/intermediate resistance" is applied to plant types that restrict the growth and development of the specified pest or pathogen, but exhibit a greater range of symptoms or damage compared to plant types with high resistance. Plant types with intermediate resistance will show less severe symptoms than susceptible plant varieties, when grown under similar field conditions and pathogen pressure. Methods of evaluating resistance are well known to one skilled in the art. Such evaluation may be performed by visual observation of a plant or a plant part (e.g., leaves, roots, flowers, fruits et. al) in determining the severity of symptoms. For example, when each plant is given a resistance score on a scale of 1 to 5 based on the severity of the reaction or symptoms, with 1 being the resistance score applied to the most resistant plants (e.g., no symptoms, or with the least symptoms), and 5 the score applied to the plants with the most severe symptoms, then a line is rated as being resistant when at least 75% of the plants have a resistance score at a 1, 2, or 3 level, while susceptible lines are those having more than 25% of the plants scoring at a 4 or 5 level. If a more detailed visual evaluation is possible, then one can use a scale from 1 to 10 so as to broaden out the range of scores and thereby hopefully provide a greater scoring spread among the plants being evaluated.

Another scoring system is a root inoculation test based on the development of the necrosis after inoculation and its position towards the cotyledon (such as one derived from Bosland et al., 1991), wherein 0 stands for no symptom after infection; 1 stands for a small necrosis at the hypocotyl after infection; 2 stands a necrosis under the cotyledons after infection; 3 stands for necrosis above the cotyledons after infection; 4 stands for a necrosis above the cotyledons together with a wilt of the plant after infection, while eventually, 5 stands for a dead plant.

In addition to such visual evaluations, disease evaluations can be performed by determining the pathogen bio-density in a plant or plant part using electron microscopy and/or through molecular biological methods, such as protein hybridization (e.g., ELISA, measuring pathogen protein density) and/or nucleic acid hybridization (e.g., RT-PCR, measuring pathogen RNA density). Depending on the particular pathogen/plant combination, a plant may be determined resistant to the pathogen, for example, if it has a pathogen RNA/DNA and/or protein density that is about 50%, or about 40%, or about 30%, or about 20%, or about 10%, or about 5%, or about 2%, or about 1%, or about 0.1%, or about 0.01%, or about 0.001%, or about 0.0001% of the RNA/DNA and/or protein density in a susceptible plant.

Methods used in breeding plants for disease resistance are similar to those used in breeding for other characters. It is necessary to know as much as possible about the nature of inheritance of the resistant characters in the host plant and the existence of physiological races or strains of the pathogen.

As used herein, the term "full resistance" is referred to as complete failure of the pathogen to develop after infection, and may either be the result of failure of the pathogen to enter the cell (no initial infection) or may be the result of failure of the pathogen to multiply in the cell and infect subsequent cells (no subliminal infection, no spread). The presence of full resistance may be determined by establishing the absence of pathogen protein or pathogen RNA in cells of the plant, as well as the absence of any disease symptoms in said plant, upon exposure of said plant to an infective dosage of pathogen (i.e. after 'infection'). Among breeders, this phenotype is often referred to as "immune". "Immunity" as used herein thus refers to a form of resistance characterized by absence of pathogen replication even when the pathogen is actively transferred into cells by e.g. electroporation.

As used herein, the term "partial resistance" is referred to as reduced multiplication of the pathogen in the cell, as reduced (systemic) movement of the pathogen, and/or as reduced symptom development after infection. The presence of partial resistance may be determined by establishing the systemic presence of low concentration of pathogen protein or pathogen RNA in the plant and the presence of decreased or delayed disease-symptoms in said plant upon exposure of said plant to an infective dosage of pathogen. Protein concentration may be determined by using a quantitative detection method (e.g. an ELISA method or a quantitative reverse transcriptase-polymerase chain reaction (RT-PCR)). Among breeders, this phenotype is often referred to as "intermediate resistant."

As used herein, the term "tolerant" is used herein to indicate a phenotype of a plant wherein disease-symptoms remain absent upon exposure of said plant to an infective dosage of pathogen, whereby the presence of a systemic or local pathogen infection, pathogen multiplication, at least the presence of pathogen genomic sequences in cells of said plant and/or genomic integration thereof can be established. Tolerant plants are therefore resistant for symptom expression but symptomless carriers of the pathogen. Sometimes, pathogen sequences may be present or even multiply in plants without causing disease symptoms. This phenomenon is also known as "latent infection". In latent infections, the pathogen may exist in a truly latent non-infectious occult form, possibly as an integrated genome or an episomal agent (so that pathogen protein cannot be found in the cytoplasm, while PCR protocols may indicate the present of pathogen nucleic acid sequences) or as an infectious and continuously replicating agent. A reactivated pathogen may spread and initiate an epidemic among susceptible contacts. The presence of a "latent infection" is indistinguishable from the presence of a "tolerant" phenotype in a plant.

As used herein, the term "susceptible" is used herein to refer to a plant having no or virtually no resistance to the pathogen resulting in entry of the pathogen into the plant and multiplication and systemic spread of the pathogen, resulting in disease symptoms. The term "susceptible" is therefore equivalent to "non-resistant".

As used herein, the term "offspring" refers to any plant resulting as progeny from a vegetative or sexual reproduction from one or more parent plants or descendants thereof. For instance an offspring plant may be obtained by cloning or selfing of a parent plant or by crossing two parents plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "cultivar" refers to a variety, strain or race of plant that has been produced by horticultural or agronomic techniques and is not normally found in wild populations.

As used herein, the terms "dicotyledon," "dicot" and "dicotyledonous" refer to a flowering plant having an embryo containing two seed halves or cotyledons. Examples include tobacco; tomato; the legumes, including peas, alfalfa, clover and soybeans; oaks; maples; roses; mints; squashes; daisies; walnuts; cacti; violets and buttercups.

As used herein, the term "monocotyledon," "monocot" or "monocotyledonous" refer to any of a subclass (Monocotyledoneae) of flowering plants having an embryo containing only one seed leaf and usually having parallel-veined leaves, flower parts in multiples of three, and no secondary growth in stems and roots. Examples include lilies; orchids; rice; corn, grasses, such as tall fescue, goat grass, and Kentucky bluegrass; grains, such as wheat, oats and barley; irises; onions and palms.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, organism (e.g., a plant), or group of organisms.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes. Since the present invention relates to QTLs, i.e. genomic regions that may comprise one or more genes or regulatory sequences, it is in some instances more accurate to refer to "haplotype" (i.e. an allele of a chromosomal segment) instead of "allele", however, in those instances, the term "allele" should be understood to comprise the term "haplotype". Alleles are considered identical when they express a similar phenotype. Differences in sequence are possible but not important as long as they do not influence phenotype.

As used herein, the term "locus" (plural: "loci") refers to any site that has been defined genetically. A locus may be a gene, or part of a gene, or a DNA sequence that has some regulatory role, and may be occupied by different sequences.

As used herein, the term "molecular marker" or "genetic marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence—characterized amplified regions (SCARs), cleaved amplified polymorphic sequence (CAPS) markers or isozyme markers or combinations of the markers described herein which defines a specific genetic and chromosomal location. Mapping of molecular markers in the vicinity of an allele is a procedure which can be performed quite easily by the average person skilled in molecular-biological techniques which techniques are for instance described in Lefebvre and Chevre, 1995; Lorez and Wenzel, 2007, Srivastava and Narula, 2004, Meksem and Kahl, 2005, Phillips and Vasil, 2001. General information concerning AFLP technology can be found in Vos et al. (1995, AFLP: a new technique for DNA fingerprinting, Nucleic Acids Res. 1995 Nov. 11; 23(21): 4407-4414).

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the term "heterozygote" refers to a diploid or polyploid individual cell or plant having different alleles (forms of a given gene) present at least at one locus.

As used herein, the term "heterozygous" refers to the presence of different alleles (forms of a given gene) at a particular gene locus.

As used herein, the term "homozygote" refers to an individual cell or plant having the same alleles at one or more loci.

As used herein, the term "homozygous" refers to the presence of identical alleles at one or more loci in homologous chromosomal segments.

As used herein, the term "homologous" or "homolog" is known in the art and refers to related sequences that share a common ancestor or family member and are determined based on the degree of sequence identity. The terms "homology", "homologous", "substantially similar" and "corresponding substantially" are used interchangeably herein. Homologs usually control, mediate, or influence the same or similar biochemical pathways, yet particular homologs may give rise to differing phenotypes. It is therefore understood, as those skilled in the art will appreciate, that the invention encompasses more than the specific exemplary sequences. These terms describe the relationship between a gene found in one species, subspecies, variety, cultivar or strain and the corresponding or equivalent gene in another species, subspecies, variety, cultivar or strain. For purposes of this invention homologous sequences are compared.

The term "homolog" is sometimes used to apply to the relationship between genes separated by the event of speciation (see "ortholog") or to the relationship between genes separated by the event of genetic duplication (see "paralog").

The term "ortholog" refers to genes in different species that evolved from a common ancestral gene by speciation. Normally, orthologs retain the same function in the course of evolution. Identification of orthologs is critical for reliable prediction of gene function in newly sequenced genomes.

The term "paralog" refers to genes related by duplication within a genome. While orthologs generally retain the same function in the course of evolution, paralogs can evolve new functions, even if these are related to the original one.

"Homologous sequences" or "homologs" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in *Current Protocols in Molecular Biology* (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Mich.), AlignX, and Vector NTI (Invitrogen, Carlsbad, Calif.).

As used herein, the term "hybrid" refers to any individual cell, tissue or plant resulting from a cross between parents that differ in one or more genes.

As used herein, the term "inbred" or "inbred line" refers to a relatively true-breeding strain.

The term "single allele converted plant" as used herein refers to those plants which are developed by a plant breeding technique called backcrossing wherein essentially all of the desired morphological and physiological characteristics of an inbred are recovered in addition to the single allele transferred into the inbred via the backcrossing technique.

As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (TO) plant regenerated from material of that line; (b) has a pedigree comprised of a TO plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

As used herein, the terms "introgression", "introgressed" and "introgressing" refer to the process whereby genes of one species, variety or cultivar are moved into the genome of another species, variety or cultivar, by crossing those species. The crossing may be natural or artificial. The process may optionally be completed by backcrossing to the recurrent parent, in which case introgression refers to infiltration of the genes of one species into the gene pool of another through repeated backcrossing of an interspecific hybrid with one of its parents. An introgression may also be described as a heterologous genetic material stably integrated in the genome of a recipient plant.

As used herein, the term "population" means a genetically homogeneous or heterogeneous collection of plants sharing a common genetic derivation.

As used herein, the term "variety" or "cultivar" means a group of similar plants that by structural features and performance can be identified from other varieties within the same species. The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

As used herein, the term "mass selection" refers to a form of selection in which individual plants are selected and the next generation propagated from the aggregate of their seeds. More details of mass selection are described herein in the specification.

As used herein, the term "open pollination" refers to a plant population that is freely exposed to some gene flow, as opposed to a closed one in which there is an effective barrier to gene flow.

As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein, the term "self-crossing", "self pollinated" or "self-pollination" means the pollen of one flower on one plant is applied (artificially or naturally) to the ovule (stigma) of the same or a different flower on the same plant.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

As used herein, the term "at least a portion" of a nucleic acid or polypeptide means a portion having the minimal size characteristics of such sequences, or any larger fragment of the full length molecule, up to and including the full length molecule. For example, a portion of a nucleic acid may be 12 nucleotides, 13 nucleotides, 14 nucleotides, 15 nucleotides, 16 nucleotides, 17 nucleotides, 18 nucleotides, 19 nucleotides, 20 nucleotides, 22 nucleotides, 24 nucleotides, 26 nucleotides, 28 nucleotides, 30 nucleotides, 32 nucleotides, 34 nucleotides, 36 nucleotides, 38 nucleotides, 40 nucleotides, 45 nucleotides, 50 nucleotides, 55 nucleotides, and so on, going up to the full length nucleic acid. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as hybridization probe may be as short as 12 nucleotides; in one embodiment, it is 20 nucleotides. A portion of a polypeptide useful as an epitope may be as short as 4 amino acids. A portion of a polypeptide that performs the function of the full-length polypeptide would generally be longer than 4 amino acids.

As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988).

As used herein, the term "suppression" or "disruption" of regulation refers to reduced activity of regulatory proteins, and such reduced activity can be achieved by a variety of mechanisms including antisense, mutation knockout or RNAi. Antisense RNA will reduce the level of expressed protein resulting in reduced protein activity as compared to wild type activity levels. A mutation in the gene encoding a protein may reduce the level of expressed protein and/or interfere with the function of expressed protein to cause reduced protein activity.

As used herein, the terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

As used herein, "coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

As used herein, "regulatory sequences" may include, but are not limited to, promoters, translation leader sequences, introns, and polyadenylation recognition sequences.

As used herein, "promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

As used herein, the "3' non-coding sequences" or "3' UTR (untranslated region) sequence" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. (1989) Plant Cell 1:671-680.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

As used herein, the term "vector", "plasmid", or "construct" refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, recombinant plant viruses. Non-limiting examples of plant viruses include, TMV-mediated (transient) transfection into tobacco (Tuipe, T-H et al (1993), J. Virology Meth, 42: 227-239), ssDNA genomes viruses (e.g., family Geminiviridae), reverse transcribing viruses (e.g., families Caulimoviridae, Pseudoviridae, and Metaviridae), dsNRA viruses (e.g., families Reoviridae and Partitiviridae), (−) ssRNA viruses (e.g., families Rhabdoviridae and Bunyaviridae), (+) ssRNA viruses (e.g., families Bromoviridae, Closteroviridae, Comoviridae, Luteoviridae, Potyviridae, Sequiviridae and Tombusviridae) and viroids (e.g., families Pospiviroldae and Avsunviroidae). Detailed classification information of plant viruses can be found in Fauquet et al (2008, "Geminivirus strain demarcation and nomenclature". *Archives of Virology* 153:783-821, incorporated herein by reference in its entirety), and Khan et al. (Plant viruses as molecular pathogens; Publisher Routledge, 2002, ISBN 1560228954, 9781560228950). Examples of non-viral vectors include, but are not limited to, liposomes, polyamine derivatives of DNA, and the like.

The present invention provides an isolated nucleic acid sequence comprising a sequence selected from the group consisting of EG261, homologs of EG261, orthologs of EG261, paralogs of EG261, and fragments and variations thereof. In one embodiment, the present invention provides an isolated polynucleotide encoding the dirigent protein produced by the nucleic acid sequence for EG261, comprising a nucleic acid sequence that shares at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to EG261.

Methods of alignment of sequences for comparison are well known in the art. Various programs and alignment algorithms are described in: Smith and Waterman (*Adv. Appl. Math.,* 2:482, 1981); Needleman and Wunsch (*J. Mol. Biol.,* 48:443, 1970); Pearson and Lipman (*Proc. Natl. Acad. Sci.,* 85:2444, 1988); Higgins and Sharp (Gene, 73:237-44, 1988); Higgins and Sharp (*CABIOS,* 5:151-53, 1989); Corpet et al. (*Nuc. Acids Res.,* 16:10881-90, 1988); Huang et al. (*Comp. Appls Biosci.,* 8:155-65, 1992); and Pearson et al. (*Meth. Mol. Biol.,* 24:307-31, 1994). Altschul et al. (*Nature Genet.,* 6:119-29, 1994) presents a detailed consideration of sequence alignment methods and homology calculations.

The present invention also provides a chimeric gene comprising the isolated nucleic acid sequence of any one of the polynucleotides described above operably linked to suitable regulatory sequences.

The present invention also provides a recombinant construct comprising the chimeric gene as described above. In one embodiment, said recombinant construct is a gene silencing construct, such as used in RNAi gene silencing.

The expression vectors of the present invention will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria.

The present invention also provides a transformed host cell comprising the chimeric gene as described above. In one embodiment, said host cell is selected from the group consisting of bacteria, yeasts, filamentous fungi, algae, animals, and plants.

These sequences allow the design of gene-specific primers and probes for EG261, homologs of EG261, orthologs of EG261, paralogs of EG261, and fragments and variations thereof.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T en G/C content) of primer. A pair of bi-directional primers consists of one forward and one reverse primer as commonly used in the art of DNA amplification such as in PCR amplification.

A probe comprises an identifiable, isolated nucleic acid that recognizes a target nucleic acid sequence. A probe includes a nucleic acid that is attached to an addressable location, a detectable label or other reporter molecule and that hybridizes to a target sequence. Typical labels include radioactive isotopes, enzyme substrates, co-factors, ligands, chemiluminescent or fluorescent agents, haptens, and enzymes. Methods for labelling and guidance in the choice of labels appropriate for various purposes are discussed, for example, in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989 and Ausubel et al. *Short Protocols in Molecular Biology*, $4^{th}$ ed., John Wiley & Sons, Inc., 1999.

Methods for preparing and using nucleic acid probes and primers are described, for example, in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989; Ausubel et al. *Short Protocols in Molecular Biology*, $4^{th}$ ed., John Wiley & Sons, Inc., 1999; and Innis et al. *PCR Protocols, A Guide to Methods and Applications*, Academic Press, Inc., San Diego, Calif., 1990. Amplification primer pairs can be derived from a known sequence, for example, by using computer programs intended for that purpose such as PRIMER (Version 0.5, 1991, Whitehead Institute for Biomedical Research, Cambridge, Mass.). One of ordinary skill in the art will appreciate that the specificity of a particular probe or primer increases with its length. Thus, in order to obtain greater specificity, probes and primers can be selected that comprise at least 20, 25, 30, 35, 40, 45, 50 or more consecutive nucleotides of a target nucleotide sequences.

EG261 Proteins

The present invention also provides polypeptides and amino acid sequences comprising at least a portion of the isolated proteins encoded by nucleotide sequences for EG261, homologs of EG261, orthologs of EG261, paralogs of EG261, and fragments and variations thereof.

The present invention also provides an isolated amino acid sequence encoded by the nucleic acid sequences of EG261, homologs of EG261, orthologs of EG261, paralogs of EG261, and/or fragments and variations thereof. In some embodiments, the present invention provides an isolated polypeptide comprising an amino acid sequence that shares at least about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to an amino acid sequence encoded by the nucleic acid sequences of EG261, homologs of EG261, orthologs of EG261, paralogs of EG261, and/or fragments and variations thereof. In one embodiment, the present invention provides an isolated polypeptide comprising an amino acid sequence which encodes an amino acid sequence that shares at least about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to an amino acid sequence encoded by the nucleic acid sequences of EG261, homologs of EG261, orthologs of EG261, paralogs of EG261, and/or fragments and variations thereof.

The invention also encompasses variants and fragments of proteins of an amino acid sequence encoded by the nucleic acid sequences of EG261, homologs of EG261, orthologs of EG261 and/or paralogs of EG261. The variants may contain alterations in the amino acid sequences of the constituent proteins. The term "variant" with respect to a polypeptide refers to an amino acid sequence that is altered by one or more amino acids with respect to a reference sequence. The variant can have "conservative" changes, or "nonconservative" changes, e.g., analogous minor variations can also include amino acid deletions or insertions, or both.

Functional fragments and variants of a polypeptide include those fragments and variants that maintain one or more functions of the parent polypeptide. It is recognized that the gene or cDNA encoding a polypeptide can be considerably mutated without materially altering one or more of the polypeptide's functions. First, the genetic code is well-known to be degenerate, and thus different codons encode the same amino acids. Second, even where an amino acid substitution is introduced, the mutation can be conservative and have no material impact on the essential function(s) of a protein. See, e.g., *Stryer Biochemistry* 3rd Ed., 1988. Third, part of a polypeptide chain can be deleted without impairing or eliminating all of its functions. Fourth, insertions or additions can be made in the polypeptide chain for example, adding epitope tags, without impairing or eliminating its functions (Ausubel et al. *J. Immunol.* 159(5): 2502-12, 1997). Other modifications that can be made without materially impairing one or more functions of a polypeptide can include, for example, in vivo or in vitro chemical and biochemical modifications or the incorporation of unusual amino acids. Such modifications include, but are not limited to, for example, acetylation, carboxylation, phosphorylation, glycosylation, ubiquination, labelling, e.g., with radionucleotides, and various enzymatic modifications, as will be readily appreciated by those well skilled in the art.

A variety of methods for labelling polypeptides, and labels useful for such purposes, are well known in the art, and include radioactive isotopes such as $^{32}$P, ligands which bind to or are bound by labelled specific binding partners (e.g., antibodies), fluorophores, chemiluminescent agents, enzymes, and anti-ligands. Functional fragments and variants can be of varying length. For example, some fragments have at least 10, 25, 50, 75, 100, 200, or even more amino acid residues. These mutations can be natural or purposely changed. In some embodiments, mutations containing alterations that produce silent substitutions, additions, or deletions, but do not alter the properties or activities of the proteins or how the proteins are made are an embodiment of the invention.

Conservative amino acid substitutions are those substitutions that, when made, least interfere with the properties of the original protein, that is, the structure and especially the function of the protein is conserved and not significantly changed by such substitutions. Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain. Further information about conservative substitutions can be found, for instance, in Ben Bassat et al. (*J. Bacteriol.*, 169:751-757, 1987), O'Regan et al. (*Gene*, 77:237-251, 1989), Sahin-Toth et al. (*Protein Sci.*, 3:240-247, 1994), Hochuli et al. (*Bio/Technology*, 6:1321-1325, 1988) and in widely used textbooks of genetics and molecular biology. The Blosum matrices are commonly used for determining the relatedness of polypeptide sequences. The Blosum matrices were created using a large database of trusted alignments (the BLOCKS database), in which pairwise sequence alignments related by less than some threshold percentage identity were counted (Henikoff et al., *Proc. Natl. Acad. Sci. USA*, 89:10915-10919, 1992). A threshold of 90% identity was used for the highly conserved target frequencies of the BLOSUM90 matrix. A threshold of 65% identity was used for the BLOSUM65 matrix. Scores of zero and above in the Blosum matrices are considered "conservative substitutions" at the percentage identity selected. The following table shows exemplary conservative amino acid substitutions.

| Original Residue | Very Highly - Conserved Substitutions | Highly Conserved Substitutions (from the Blosum90 Matrix) | Conserved Substitutions (from the Blosum65 Matrix) |
| --- | --- | --- | --- |
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

In some examples, variants can have no more than 3, 5, 10, 15, 20, 25, 30, 40, 50, or 100 conservative amino acid changes (such as very highly conserved or highly conserved amino acid substitutions). In other examples, one or several hydrophobic residues (such as Leu, Ile, Val, Met, Phe, or Trp) in a variant sequence can be replaced with a different hydrophobic residue (such as Leu, Ile, Val, Met, Phe, or Trp) to create a variant functionally similar to the disclosed an amino acid sequences encoded by the nucleic acid sequences of EG261, homologs of EG261, orthologs of EG261 and/or paralogs of EG261, and/or fragments and variations thereof.

In some embodiments, variants may differ from the disclosed sequences by alteration of the coding region to fit the codon usage bias of the particular organism into which the molecule is to be introduced. In other embodiments, the coding region may be altered by taking advantage of the degeneracy of the genetic code to alter the coding sequence such that, while the nucleotide sequence is substantially altered, it nevertheless encodes a protein having an amino acid sequence substantially similar to the disclosed an amino acid sequences encoded by the nucleic acid sequences of EG261, homologs of EG261, orthologs of EG261 and/or paralogs of EG261, and/or fragments and variations thereof.

In some embodiments, functional fragments derived from the EG261 orthologs of the present invention are provided. The functional fragments can still confer resistance to pathogens when expressed in a plant. In some embodiments, the functional fragments contain at least the dirigent domain of a wild type EG261 orthologs, or functional variants thereof. In some embodiments, the functional fragments contain one or more conserved region shared by two or more EG261 orthologs, shared by two or more EG261 orthologs in the same plant genus, shared by two or more dicot EG261 orthologs, and/or shared by two or more monocot EG261 orthologs. Non-limiting exemplary conserved regions are shown in FIGS. 2 to 4. The dirigent domain or conserved regions can be determined by any suitable computer program, such as NCBI protein BLAST program and NCBI Alignment program, or equivalent programs. In some embodiments, the functional fragments are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acids shorter compared to the EG261 orthologs of the present invention. In some embodiments, the functional fragments are made by deleting one or more amino acid of the EG261 orthologs of the present invention. In some embodiments, the functional fragments share at least 80%, 85%, 90%, 95%, 96%, 97%, 98%, 99%, or more identity to the EG261 orthologs of the present invention.

In some embodiments, functional chimeric or synthetic polypeptides derived from the EG261 orthologs of the present invention are provided. The functional chimeric or synthetic polypeptides can still confer resistance to pathogens when expressed in a plant. In some embodiments, the functional chimeric or synthetic polypeptides contain at least the dirigent domain of a wild type EG261 orthologs, or functional variants thereof. In some embodiments, the functional chimeric or synthetic polypeptides contain one or more conserved region shared by two or more EG261 orthologs, shared by two or more EG261 orthologs in the same plant genus, shared by two or more dicot EG261 orthologs, and/or shared by two or more monocot EG261 orthologs. Non-limiting exemplary conserved regions are shown in FIGS. 2 to 4. The dirigent domain or conserved regions can be determined by any suitable computer program, such as NCBI protein BLAST program and NCBI Alignment program, or equivalent programs. In some embodiments, the functional chimeric or synthetic polypeptides share at least 80%, 85%, 90%, 95%, 96%, 97%, 98%, 99%, or more identity to the EG261 orthologs of the present invention.

Sequences of conserved regions can also be used to knock-down the level of one or more EG261 orthologs. In some embodiments, sequences of conserved regions can be used to make gene silencing molecules to target one ore more EG261 orthologs. In some embodiments, the gene silencing molecules are selected from the group consisting of double-stranded polynucleotides, single-stranded polynucleotides or Mixed Duplex Oligonucleotides. In some embodiments, the gene silencing molecules comprises a DNA/RNA fragment of about 10 bp, 15 bp, 19 bp, 20 bp, 21 bp, 25 bp, 30 bp, 40 bp, 50 bp, 60 bp, 70 bp, 80 bp, 90 bp, 100 bp, 150 bp, 200 pb, 250 bp, 300 bp, 350 bp, 400 bp, 500 bp, 600 bp, 700 bp, 800 bp, 900 bp, 1000 bp, or more polynucleotides, wherein the DNA/RNA fragment share at least 90%, 95%, 99%, or more identity to a conserved region of the EG261 orthologs sequences of the present invention, or complementary sequences thereof.

Plant Transformation

The present polynucleotides coding for EG261, homologs of EG261, orthologs of EG261 and/or paralogs of EG261, and/or fragments and variations thereof of the present invention can be transformed into soybean or other plant genera.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538,877; 5,538,880; 5,550,318; 5,641,664; 5,736,369 and 5,736,369; International Patent Application Publication Nos. WO2002/038779 and WO/2009/117555; Lu et al., (Plant Cell Reports, 2008, 27:273-278); Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al., *Bio/Tech*. 8:33-38 (1990)), each of which is expressly incorporated herein by reference in their entirety.

*Agrobacterium tumefaciens* is a naturally occurring bacterium that is capable of inserting its DNA (genetic information) into plants, resulting in a type of injury to the plant known as crown gall. Most species of plants can now be transformed using this method, including cucurbitaceous species.

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants have been transformed using this method.

The most common method for the introduction of new genetic material into a plant genome involves the use of living cells of the bacterial pathogen *Agrobacterium tumefaciens* to literally inject a piece of DNA, called transfer or T-DNA, into individual plant cells (usually following wounding of the tissue) where it is targeted to the plant nucleus for chromosomal integration. There are numerous patents governing *Agrobacterium* mediated transformation and particular DNA delivery plasmids designed specifically for use with *Agrobacterium*—for example, U.S. Pat. No. 4,536,475, EP0265556, EP0270822, WO8504899, WO8603516, U.S. Pat. No. 5,591,616, EP0604662, EP0672752, WO8603776, WO9209696, WO9419930, WO9967357, U.S. Pat. No. 4,399,216, WO8303259, U.S. Pat. No. 5,731,179, EP068730, WO9516031, U.S. Pats. No. 5,693,512, 6,051,757 and EP904362A1. *Agrobacterium*-mediated plant transformation involves as a first step the placement of DNA fragments cloned on plasmids into living *Agrobacterium* cells, which are then subsequently used for transformation into individual plant cells. *Agrobacterium*-mediated plant transformation is thus an indirect plant transformation method. Methods of *Agrobacterium*-mediated plant transformation that involve using vectors with no T-DNA are also well known to those skilled in the art and can have applicability in the present invention. See, for example, U.S. Pat. No. 7,250,554, which utilizes P-DNA instead of T-DNA in the transformation vector.

A transgenic plant formed using *Agrobacterium* transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

Direct plant transformation methods using DNA have also been reported. The first of these to be reported historically is electroporation, which utilizes an electrical current applied to a solution containing plant cells (M. E. Fromm et al., Nature, 319, 791 (1986); H. Jones et al., Plant Mol. Biol., 13, 501 (1989) and H. Yang et al., Plant Cell Reports, 7, 421 (1988). Another direct method, called "biolistic bombardment", uses ultrafine particles, usually tungsten or gold, that are coated with DNA and then sprayed onto the surface of a plant tissue with sufficient force to cause the particles to penetrate plant cells, including the thick cell wall, membrane and nuclear envelope, but without killing at least some of them (U.S. Pat. Nos. 5,204,253, 5,015,580). A third direct method uses fibrous forms of metal or ceramic consisting of sharp, porous or hollow needle-like projections that literally impale the cells, and also the nuclear envelope of cells. Both silicon carbide and aluminium borate whiskers have been used for plant transformation (Mizuno et al., 2004; Petolino et al., 2000; U.S. Pat. No. 5,302,523 US Application 20040197909) and also for bacterial and animal transformation (Kaepler et al., 1992; Raloff, 1990; Wang, 1995). There are other methods reported, and undoubtedly, additional methods will be developed. However, the efficiencies of each of these indirect or direct methods in introducing foreign DNA into plant cells are invariably extremely low, making it necessary to use some method for selection of only those cells that have been transformed, and further, allowing growth and regeneration into plants of only those cells that have been transformed.

For efficient plant transformation, a selection method must be employed such that whole plants are regenerated from a single transformed cell and every cell of the transformed plant carries the DNA of interest. These methods can employ positive selection, whereby a foreign gene is supplied to a plant cell that allows it to utilize a substrate present in the medium that it otherwise could not use, such as mannose or xylose (for example, refer U.S. Pat. Nos. 5,767,378; 5,994,629). More typically, however, negative selection is used because it is more efficient, utilizing selective agents such as herbicides or antibiotics that either kill or inhibit the growth of non-transformed plant cells and reducing the possibility of chimeras. Resistance genes that are effective against negative selective agents are provided on the introduced foreign DNA used for the plant transformation. For example, one of the most popular selective agents used is the antibiotic kanamycin, together with the resistance gene neomycin phosphotransferase (nptII), which confers resistance to kanamycin and related antibiotics (see, for example, Messing & Vierra, Gene 19: 259-268 (1982); Bevan et al., Nature 304:184-187 (1983)). However, many different antibiotics and antibiotic resistance genes can be used for transformation purposes (refer U.S. Pat. Nos. 5,034,322, 6,174,724 and 6,255,560). In addition, several herbicides and herbicide resistance genes have been used for transformation purposes, including the bar gene, which confers resistance to the herbicide phosphinothricin (White et al., Nucl Acids Res 18: 1062 (1990), Spencer et al., Theor Appl Genet 79: 625-631(1990), U.S. Pat. Nos. 4,795,855, 5,378,824 and 6,107,549). In addition, the dhfr gene, which confers resistance to the anticancer agent methotrexate, has been used for selection (Bourouis et al., EMBO J. 2(7): 1099-1104 (1983).

Non-limiting examples of binary vectors suitable for soybean species transformation and transformation methods are described by Yi et al. 2006 (Transformation of multiple soybean cultivars by infecting cotyledonary-node with *Agrobacterium tumefaciens*, African Journal of Biotechnology Vol. 5 (20), pp. 1989-1993, 16 Oct. 2006), Paz et al., 2004 (Assessment of conditions affecting *Agrobacterium*-mediated soybean transformation using the cotyledonary node explant, Euphytica 136: 167-179, 2004), U.S. Pat. Nos. 5,376,543, 5,416,011, 5,968,830, and 5,569,834, or by similar experimental procedures well known to those skilled in the art. Soybean plants can be transformed by using any method described in the above references.

The expression control elements used to regulate the expression of a given protein can either be the expression control element that is normally found associated with the coding sequence (homologous expression element) or can be a heterologous expression control element. A variety of homologous and heterologous expression control elements are known in the art and can readily be used to make expression units for use in the present invention. Transcription initiation regions, for example, can include any of the various opine initiation regions, such as octopine, mannopine, nopaline and the like that are found in the Ti plasmids of *Agrobacterium tumefaciens*. Alternatively, plant viral promoters can also be used, such as the cauliflower mosaic virus 19S and 35S promoters (CaMV 19S and CaMV 35S promoters, respectively) to control gene expression in a plant (U.S. Pat. Nos. 5,352,605; 5,530,196 and 5,858,742 for example). Enhancer sequences derived from the CaMV can also be utilized (U.S. Pat. Nos. 5,164,316; 5,196,525; 5,322,938; 5,530,196; 5,352,605; 5,359,142; and 5,858,742 for example). Lastly, plant promoters such as prolifera promoter, fruit specific promoters, Ap3 promoter, heat shock promoters, seed specific promoters, etc. can also be used.

Either a gamete-specific promoter, a constitutive promoter (such as the CaMV or Nos promoter), an organ-specific promoter (such as the E8 promoter from tomato), or an inducible promoter is typically ligated to the protein or antisense encoding region using standard techniques known in the art. The expression unit may be further optimized by employing supplemental elements such as transcription terminators and/or enhancer elements.

Thus, for expression in plants, the expression units will typically contain, in addition to the protein sequence, a plant promoter region, a transcription initiation site and a transcription termination sequence. Unique restriction enzyme sites at the 5' and 3' ends of the expression unit are typically included to allow for easy insertion into a pre-existing vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the *Agrobacterium* octopine synthase signal (Gielen et al., EMBO J 3:835-846 (1984)) or the nopaline synthase signal (Depicker et al., Mol. and Appl. Genet. 1:561-573 (1982)). The resulting expression unit is ligated into or otherwise constructed to be included in a vector that is appropriate for higher plant transformation. One or more expression units may be included in the same vector. The vector will typically contain a selectable marker gene expression unit by which transformed plant cells can be identified in culture. Usually, the marker gene will encode resistance to an antibiotic, such as G418, hygromycin, bleomycin, kanamycin, or gentamicin or to an herbicide, such as glyphosate (Round-Up) or glufosinate (BASTA) or atrazine. Replication sequences, of bacterial or viral origin, are generally also included to allow the vector to be cloned in a bacterial or phage host; preferably a broad host range for prokaryotic origin of replication is included. A selectable marker for bacteria may also be included to allow selection of bacterial cells bearing the desired construct. Suitable prokaryotic selectable markers include resistance to antibiotics such as ampicillin, kanamycin or tetracycline. Other DNA sequences encoding additional functions may also be present in the vector, as is known in the art. For instance, in the case of *Agrobacterium* transformations, T-DNA sequences will also be included for subsequent transfer to plant chromosomes.

To introduce a desired gene or set of genes by conventional methods requires a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as improved fatty acid composition, and to introduce these genes into already useful varieties of plants. Once the foreign genes have been introduced into a plant, that plant can then be used in conventional plant breeding schemes (e.g., pedigree breeding, single-seed-descent breeding schemes, reciprocal recurrent selection) to produce progeny which also contain the gene of interest.

Genes can be introduced in a site directed fashion using homologous recombination. Homologous recombination permits site-specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451,513; 5,501,967 and 5,527,695.

Breeding Methods

Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988). For population improvement methods specific for soybean see, e.g., J. R. Wilcox, editor (1987) SOYBEANS: Improvement, Production, and Uses, Second Edition, American Society of Agronomy, Inc., Crop Science Society of America, Inc., and Soil Science Society of America, Inc., publishers, 888 pages.

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or toperosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enters a synthetic varies widely. In practice, numbers of parental lines range from 10 to several hundred, with 100-200 being the average. Broad based synthetics formed from 100 or more clones would be expected to be more stable during seed multiplication than narrow based synthetics.

Hybrids. A hybrid is an individual plant resulting from a cross between parents of differing genotypes. Commercial hybrids are now used extensively in many crops, including corn (maize), sorghum, sugar beet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

Bulk Segregation Analysis (BSA). BSA, a.k.a. bulked segregation analysis, or bulk segregant analysis, is a method described by Michelmore et al. (Michelmore et al., 1991, Identification of markers linked to disease-resistance genes by bulked segregant analysis: a rapid method to detect markers in specific genomic regions by using segregating populations. *Proceedings of the National Academy of Sciences*, USA, 99:9828-9832) and Quarrie et al. (Quarrie et al., Bulk segregant analysis with molecular markers and its use for improving drought resistance in maize, 1999, *Journal of Experimental Botany*, 50(337):1299-1306).

For BSA of a trait of interest, parental lines with certain different phenotypes are chosen and crossed to generate F2, doubled haploid or recombinant inbred populations with QTL analysis. The population is then phenotyped to identify individual plants or lines having high or low expression of the trait. Two DNA bulks are prepared, one from the individuals having one phenotype (e.g., resistant to pathogen), and the other from the individuals having reversed phenotype (e.g., susceptible to pathogen), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs). Markers linked to the phenotype can be identified and used for breeding or QTL mapping.

Gene Pyramiding. The method to combine into a single genotype a series of target genes identified in different parents is usually referred as gene pyramiding. A non-limiting example of gene pyramiding scheme is shown in FIG. 3. The first part of a gene pyramiding breeding is called a pedigree and is aimed at cumulating one copy of all target genes in a single genotype (called root genotype). The second part is called the fixation steps and is aimed at fixing the target genes into a homozygous state, that is, to derive the ideal genotype (ideotype) from the root genotype. Gene pyramiding can be combined with marker assisted selection (MAS, see Hospital et al., 1992, 1997a, and 1997b, and Moreau et al, 1998) or marker based recurrent selection (MBRS, see Hospital et al., 2000).

RNA Interference (RNAi)

RNA interference (RNAi) is the process of sequence-specific, post-transcriptional gene silencing or transcriptional gene silencing in animals and plants, initiated by double-stranded RNA (dsRNA) that is homologous in sequence to the silenced gene. The preferred RNA effector molecules useful in this invention must be sufficiently distinct in sequence from any host polynucleotide sequences for which function is intended to be undisturbed after any of the methods of this invention are performed. Computer algorithms may be used to define the essential lack of homology between the RNA molecule polynucleotide sequence and host, essential, normal sequences.

The term "dsRNA" or "dsRNA molecule" or "double-strand RNA effector molecule" refers to an at least partially double-strand ribonucleic acid molecule containing a region of at least about 19 or more nucleotides that are in a double-strand conformation. The double-stranded RNA effector molecule may be a duplex double-stranded RNA formed from two separate RNA strands or it may be a single RNA strand with regions of self-complementarity capable of assuming an at least partially double-stranded hairpin conformation (i.e., a hairpin dsRNA or stem-loop dsRNA). In various embodiments, the dsRNA consists entirely of ribonucleotides or consists of a mixture of ribonucleotides and deoxynucleotides, such as RNA/DNA hybrids. The dsRNA may be a single molecule with regions of self-complementarity such that nucleotides in one segment of the molecule base pair with nucleotides in another segment of the molecule. In one aspect, the regions of self-complementarity are linked by a region of at least about 3-4 nucleotides, or about 5, 6, 7, 9 to 15 nucleotides or more, which lacks complementarity to another part of the molecule and thus remains single-stranded (i.e., the "loop region"). Such a molecule will assume a partially double-stranded stem-loop structure, optionally, with short single stranded 5' and/or 3' ends. In one aspect the regions of self-complementarity of the hairpin dsRNA or the double-stranded region of a duplex dsRNA will comprise an Effector Sequence and an Effector Complement (e.g., linked by a single-stranded loop region in a hairpin dsRNA). The Effector Sequence or Effector Strand is that strand of the double-stranded region or duplex which is incorporated in or associates with RISC. In one aspect the double-stranded RNA effector molecule will comprise an at least 19 contiguous nucleotide effector sequence, preferably 19 to 29, 19 to 27, or 19 to 21 nucleotides, which is a reverse complement to the RNA of nucleic acid sequences coding for EG261, homologs of EG261, orthologs of EG261 and/or paralogs of EG261, and/or fragments and variations thereof, or an opposite strand replication intermediate. In one embodiment, said double-stranded RNA effector molecules are provided by providing to a soybean or other plant, plant tissue, or plant cell an expression construct comprising one or more double-stranded RNA effector molecules. In one embodiment, the expression construct comprises a double-strand RNA derived from any one of nucleic acid sequences coding for EG261, homologs of EG261, orthologs of EG261 and/or paralogs of EG261, and/or fragments and variations thereof. In other embodiments, the expression construct comprises a double-strand RNA derived from more than one sequences of nucleic acid sequences coding for EG261, homologs of EG261, orthologs of EG261 and/or paralogs of EG261, and/or fragments and variations thereof. In further embodiments, the expression construct comprises a double-strand RNA derived from more than one sequences of nucleic acid sequences coding for EG261, homologs of EG261, orthologs of EG261 and/or paralogs of EG261, and/or fragments and variations thereof, and one or more other genes involved in pathogen resistance. One skilled in the art will be able to design suitable double-strand RNA effector molecule based on the nucleotide sequences of nucleic acid sequences coding for EG261, homologs of EG261, orthologs of EG261 and/or paralogs of EG261, and/or fragments and variations thereof in the present invention.

In some embodiments, the dsRNA effector molecule of the invention is a "hairpin dsRNA", a "dsRNA hairpin", "short-hairpin RNA" or "shRNA", i.e., an RNA molecule of less than approximately 400 to 500 nucleotides (nt), or less than 100 to 200 nt, in which at least one stretch of at least 15 to 100 nucleotides (e.g., 17 to 50 nt, 19 to 29 nt) is based paired with a complementary sequence located on the same RNA molecule (single RNA strand), and where said sequence and complementary sequence are separated by an unpaired region of at least about 4 to 7 nucleotides (or about 9 to about 15 nt, about 15 to about 100 nt, about 100 to about 1000 nt) which forms a single-stranded loop above the stem structure created by the two regions of base complementarity. The shRNA molecules comprise at least one stem-loop structure comprising a double-stranded stem region of about 17 to about 500 bp; about 17 to about 50 bp; about 40 to about 100 bp; about 18 to about 40 bp; or from about 19 to about 29 bp; homologous and complementary to a target sequence to be inhibited; and an unpaired loop region of at least about 4 to 7 nucleotides, or about 9 to about 15 nucleotides, about 15 to about 100 nt, about 250-500 bp, about 100 to about 1000 nt, which forms a single-stranded loop above the stem structure created by the two regions of base complementarity. It will be recognized, however, that it is not strictly necessary to include a "loop region" or "loop sequence" because an RNA molecule comprising a sequence followed immediately by its reverse complement will tend to assume a stem-loop conformation even when not separated by an irrelevant "stuffer" sequence.

The expression construct of the present invention comprising DNA sequence which can be transcribed into one or more double-stranded RNA effector molecules can be transformed into a plant, wherein the transformed plant produces different fatty acid compositions than the untransformed plant. The target sequence to be inhibited by the dsRNA effector molecule include, but are not limited to, coding region, 5' UTR region, 3' UTR region of fatty acids synthesis genes. In one embodiment, the target sequence is from one or more nucleic acid sequences coding for EG261, homologs of EG261, orthologs of EG261 and/or paralogs of EG261, and/or fragments and variations thereof.

The effects of RNAi can be both systemic and heritable in plants. In plants, RNAi is thought to propagate by the transfer of siRNAs between cells through plasmodesmata. The heritability comes from methylation of promoters targeted by RNAi; the new methylation pattern is copied in each new generation of the cell. A broad general distinction between plants and animals lies in the targeting of endogenously produced miRNAs; in plants, miRNAs are usually perfectly or nearly perfectly complementary to their target genes and induce direct mRNA cleavage by RISC, while animals' miRNAs tend to be more divergent in sequence and induce translational repression. Detailed methods for RNAi in plants are described in David Allis et al (Epigenetics, CSHL Press, 2007, ISBN 0879697245, 9780879697242), Sohail et al (Gene silencing by RNA interference: technology and application, CRC Press, 2005, ISBN 0849321417, 9780849321412), Engelke et al. (RAN Interference, Academic Press, 2005, ISBN 0121827976, 9780121827977), and Doran et al. (RNA Interference: Methods for Plants and Animals, CABI, 2009, ISBN 1845934105, 9781845934101), which are all herein incorporated by reference in their entireties for all purposes.

The present invention provides methods of producing soybeans or other plants containing altered and/or increased levels of pathogen tolerance and/or resistance. Such methods comprise utilizing the soybean or other plants comprising the chimeric genes as described above.

The present invention also provides methods of breeding soybean and other plants producing altered and/or increased levels of pathogen tolerance and/or resistance. In one embodiment, such methods comprise:

i) making a cross between the soybean or other plant species with nucleic acid sequences coding for EG261, homologs of EG261, orthologs of EG261 and/or paralogs of EG261, and/or fragments and variations thereof as described above to a second soybean or other plant species to make F1 plants;

ii) backcrossing said F1 plants to said second soybean or plant species, respectively;

iii) repeating backcrossing step until said nucleic acid sequences are integrated into the genome of said second soybean or other plant species, respectively. Optionally, such method can be facilitated by molecular markers.

The present invention provides methods of breeding species close to *Glycine max*, wherein said species produces altered and/or increased levels of pathogen tolerance and/or resistance. In one embodiment, such methods comprise i) making a cross between the non-*Glycine max* species containing nucleic acid sequences coding for homologs of EG261, orthologs of EG261 and/or paralogs of EG261, and/or fragments and variations thereof as described above to *Glycine max* to make F1 plants;

ii) backcrossing said F1 plants to *Glycine max*;

iii) repeating backcrossing step until said nucleic acid sequences are integrated into the genome of *Glycine max*. Special techniques (e.g., somatic hybridization) may be necessary in order to successfully transfer a gene from non-*Glycine max* species to *Glycine max*. Optionally, such method can be facilitated by molecular markers.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Example 1

Identification and Characterization of EG261 in Domesticated Soybean (*Glycine max*)

This invention involves the discovery that the soybean gene referred to herein as 'EG261' codes for a dirigent protein that confers resistance to pathogens, including resistance to nematodes. There are 2 copies of EG261 in soybeans, but only one of the gene copies, which is referred to herein as "copy A," is positively selected. The second copy, which is referred to herein as "copy B," is well-conserved and there is no evidence that it plays any role in nematode resistance (or in any other trait of agronomic interest). Unless otherwise specified herein, all references to EG261 are referring to copy A of the gene.

EG261 is very highly expressed in roots, as might be expected for a gene that confers resistance to SCN, as this is a primary route for SCN entrance to the plant.

It appears that EG261 maps into a predicted location (i.e., a QTL) on soybean chromosome 1 for SCN resistance. This QTL is supported by two different studies (Vergel C. Concibido, Brian W. Diers, and Prakash R. Arelli, *Crop Science*, VOL. 44, JULY-AUGUST 2004, 1121-1131, and Pin Yue, David A. Sleper and Prakash R. Arelli, *Crop Science*, VOL. 41, SEPTEMBER-OCTOBER 2001, 1589-1595). However, this QTL is broad, and likely contains hundreds of genes, so the exact gene-of-interest has not previously been isolated. That positively-selected EG261 appears to fall within this QTL is consistent with our hypothesis that EG controls and confers SCN resistance. (It is noted, however, that the QTL location is still only tentatively mapped due to differences in size and structure of mapping populations, DNA marker platforms, and limited availability of DNA markers.)

EG261 soybean sequences follow. Initiation codons shown in underlined lower case font. Termination codons shown in bolded lower case font. The UTR sequence is in lower case.

The gene sequence of EG261 (SEQ ID NO: 1), derived from cultivated soybean (*Glycine max*) follows:

5'-
agcaagagatgctcaaacccaaattcacctacttcgatgcttccccacc ttataaattcttgcattaatttaccactttcatcacccaatccacttcct ctaattgacacccacctaaacc<u>atg</u>GCTTCCCACTTCCTCAAATCCCTCC

TTCTCCTCTCCACCTATGCCCTCACCATCTCAGCAGAATACACAGGCTTC

GTGGGAACACTAGACCCAAAGTCCATAGGCATACACCACAAGAAAACCCT

AAGCCACTTCAGGTTCTACTGGCACGAAGTCTTCAGCGGAGAAAACCCCA

-continued
CATCGGTTAGAATCATTCCCTCACTCCCCAAATACAACGCAACCACAACC

TTCGGCTCCGTTGGAATCTTTGACACCCCTTTAACCGTGGGACCTGAGGT

GTACTCCAAGGTTGTCGGAAAAGCCGAGGGCTTGTTTGCCTCCACGTCAC

AAACGCAGTTTGACCTGTTACTGATTTACAACTTCGCGTTGACCCAAGGG

AAGTACAACGGCAGCACCATCACGTTCACGGGGAGGAGCCCCTCTCGGA

GAAGGTGAGGGAGCTGCCCATTGTTGGTGGTAGTGGGGTCTTCAAATTTG

CCACTGGGTATGTTGAGTCTAGGACGCTAAGTTTTGATCCCCAAACAAGG

AATAACACGGTTCAGTTCGACGTGTATATTTACTATtgagattattgaa tgtgttttttcatgttgatgcgttatcgctttggtctgtctcacctagtt tcta EG261 coding sequence (cultivated soybean; *Glycine max*, SEQ ID NO: 2):

<u>atg</u>GCTTCCCACTTCCTCAAATCCCTCCTTCTCCTCTCCACCTATGCCCT

CACCATCTCAGCAGAATACACAGGCTTCGTGGGAACACTAGACCCAAAGT

CCATAGGCATACACCACAAGAAAACCCTAAGCCACTTCAGGTTCTACTGG

CACGAAGTCTTCAGCGGAGAAAACCCCACATCGGTTAGAATCATTCCCTC

ACTCCCCAAATACAACGCAACCACAACCTTCGGCTCCGTTGGAATCTTTG

ACACCCCTTTAACCGTGGGACCTGAGGTGTACTCCAAGGTTGTCGGAAAA

GCCGAGGGCTTGTTTGCCTCCACGTCACAAACGCAGTTTGACCTGTTACT

GATTTACAACTTCGCGTTGACCCAAGGGAAGTACAACGGCAGCACCATCA

CGTTCACGGGGAGGAGCCCCTCTCGGAGAAGGTGAGGGAGCTGCCCATT

GTTGGTGGTAGTGGGGTCTTCAAATTTGCCACTGGGTATGTTGAGTCTAG

GACGCTAAGTTTTGATCCCCAAACAAGGAATAACACGGTTCAGTTCGACG

TGTATATTTACTATtga

The EG261 gene sequence is more than 99% identical to Sequences 65260 and 33011 of U.S. Pat. No. 7,569,389, each of which are identical to each other (SEQ ID NO: 3):

```
  1 atcacccaat ccacttcctc taattgacac ccacctaaac catggcttcc cacttcctca
 61 aatccctcct tctcctctcc acctatgccc tcaccatctc agcagaatac acaggcttcg
121 tgggaacact agacccaaag tccataggca tacaccacaa gaaaacccta agccacttca
181 ggttctactg gcacgaagtc ttcagcggag aaaaccccac atcggttaga atcattccct
241 cactccccaa atacaacgca accacaacct tcggctccgt tggaatcttt gacacccctt
301 taaccgtggg acctgaggtg tactccaagg ttgtcggaaa agccgagggc ttgtttgcct
361 ccacgtcaca aacgcagttt gacctgttac tgatttacaa cttcgcgttg acccaaggga
421 agtacaacgg cagcaccatc acgttcacgg ggaggagccc cctctcggag aaggtgaggg
481 agctgcccat tgttggtggt agtggggtct tcaaatttgc cactgggtat gttgagtcta
541 ggacgctaag ttttgatccc caaacaagga ataacacggt tcagttcgac gtgtatattt
601 actattgatg attattgaaa gtgttttttt catgttgatg cgttatcgct ttggtctgtc
661 tcacctagtt tctacataag tttcctcttt tgagggcatg tggtgtcatg gaataaagtc
721 atctttgggc aaaaaaaaa aaaaaaaa
```

Example 2

Identification of Orthologs of EG261 in Wild Soybean Species

Using analysis techniques derived from molecular evolutionary biology, gene sequences from the cultivated (i.e., domesticated) soybean, *Glycine max*, were compared to orthologous genes from species of wild soybean that are relatives to *G. max* and that were suspected to be resistant to attack by the Soybean Cyst Nematode (SCN). This analysis was performed in high-throughput fashion, applying Evolutionary Genomics' proprietary software and patented approach. See, e.g., U.S. Pat. Nos. 6,228,586; 6,274,319; and 6,280,953.

Most varieties of cultivated soybeans are susceptible to one or more races (now more commonly known as HG groups) of SCN, and even those soybean cultivars bred for resistance to SCN are now often losing that resistance as the cyst nematodes evolve the ability to evade the current resistance mechanisms. Present resistance mechanisms all depend upon only one or two genes, so are relatively easy targets for the evolution of resistance.

Wild soybean relatives were chosen for analysis; these species were those that the scientific literature suggested were tolerant to one or more races of SCN. These putatively SCN-resistant species were then tested in standard assays for SCN susceptibility/resistance. Multiple races (HG groups) were used to test each wild soybean accession. In multiple replicates, multiple plants of each wild soybean species were challenged by SCN; each challenge involved multiple SCN races/HG groups.

After demonstrating that several wild species were indeed resistant to SCN, these species were grown to maturity in order to collect RNA. Total RNA was prepared from individual plants of each of 5 SCN-resistant species. RNA was pooled from several tissues from each individual plant in order to maximize how comprehensively the transcriptome of that species was sampled. RNA was used to create cDNA libraries which were used to sequence the species' transcriptome. This was accomplished by Roche 454 high-throughput next-gen sequencing, although any appropriate DNA sequencing method could have been used.

The resulting ESTs were compared on a gene-by-gene basis. The homologous sequences were analyzed to identify those that have nucleic acid sequence differences between the two species. Then molecular evolution analysis was conducted to evaluate quantitatively and qualitatively the evolutionary significance of the differences between orthologous genes derived from cultivated soybean (*G. max*) and each wild species (for example, *Glycine tabacina*) on a pairwise basis. Each wild species was also compared in pairwise fashion to every other wild soybean species. Automated bioinformatics analysis was then applied to each pairwise comparison and only those sequences that contain a nucleotide change (or changes) that yield evolutionarily significant change(s) were retained for further analysis. This enabled the identification of genes that have evolved to confer some evolutionary advantage as well as the identification of the specific evolved changes.

Any of several different molecular evolution analyses or Ka/Ks-type methods can be employed to evaluate quantitatively and qualitatively the evolutionary significance of the identified nucleotide changes between homologous gene sequences from related species. Kreitman and Akashi (1995) Annu. Rev. Ecol. Syst. 26:403 422; Li, Molecular Evolution, Sinauer Associates, Sunderland, Mass., 1997. For example, positive selection on proteins (i.e., molecular-level adaptive evolution) can be detected in protein-coding genes by pairwise comparisons of the ratios of nonsynonymous nucleotide substitutions per nonsynonymous site (Ka) to synonymous substitutions per synonymous site (Ks) (Li et al., 1985; Li, 1993). Any comparison of Ka and Ks may be used, although it is particularly convenient and most effective to compare these two variables as a ratio. Sequences are identified by exhibiting a statistically significant difference between Ka and Ks using standard statistical methods.

Preferably, the Ka/Ks analysis by Li et al. is used to carry out the present invention, although other analysis programs that can detect positively selected genes between species can also be used. Li et al. (1985) Mol. Biol. Evol. 2:150 174; Li (1993); see also J. Mol. Evol. 36:96 99; Messier and Stewart (1997) Nature 385:151 154; Nei (1987) Molecular Evolutionary Genetics (New York, Columbia University Press). The Ka/Ks method, which comprises a comparison of the rate of non-synonymous substitutions per non-synonymous site with the rate of synonymous substitutions per synonymous site between homologous protein-coding regions of genes in terms of a ratio, is used to identify sequence substitutions that may be driven by adaptive selections as opposed to neutral selections during evolution. A synonymous ("silent") substitution is one that, owing to the degeneracy of the genetic code, makes no change to the amino acid sequence encoded; a non-synonymous substitution results in an amino acid replacement. The extent of each type of change can be estimated as Ka and Ks, respectively, the numbers of synonymous substitutions per synonymous site and non-synonymous substitutions per non-synonymous site. Calculations of Ka/Ks may be performed manually or by using software. An example of a suitable program is MEGA (Molecular Genetics Institute, Pennsylvania State University).

For the purpose of estimating Ka and Ks, either complete or partial protein-coding sequences are used to calculate total numbers of synonymous and non-synonymous substitutions, as well as non-synonymous and synonymous sites. The length of the polynucleotide sequence analyzed can be any appropriate length. Preferably, the entire coding sequence is compared, in order to determine any and all significant changes. Publicly available computer programs, such as Li93 (Li (1993) J. Mol. Evol. 36:96 99) or INA, can be used to calculate the Ka and Ks values for all pairwise comparisons. This analysis can be further adapted to examine sequences in a "sliding window" fashion such that small numbers of important changes are not masked by the whole sequence. "Sliding window" refers to examination of consecutive, overlapping subsections of the gene (the subsections can be of any length).

The comparison of non-synonymous and synonymous substitution rates is commonly represented by the Ka/Ks ratio. Ka/Ks has been shown to be a reflection of the degree to which adaptive evolution has been at work in the sequence under study. Full length or partial segments of a coding sequence can be used for the Ka/Ks analysis. The higher the Ka/Ks ratio, the more likely that a sequence has undergone adaptive evolution and the non-synonymous substitutions are evolutionarily significant. See, for example, Messier and Stewart (1997).

Ka/Ks ratios significantly greater than unity strongly suggest that positive selection has fixed greater numbers of amino acid replacements than can be expected as a result of chance alone, and is in contrast to the commonly observed pattern in which the ratio is less than or equal to one. Nei (1987); Hughes and Nei (1988) *Nature* 335:167 170; Messier and Stewart (1994) *Current Biol.* 4:911 913; Kreitman and Akashi (1995) *Ann. Rev. Ecol. Syst.* 26:403 422; Messier and Stewart (1997). Ratios less than one generally signify the role of negative, or purifying selection: there is strong pressure on the primary structure of functional, effective proteins to remain unchanged.

All methods for calculating Ka/Ks ratios are based on a pairwise comparison of the number of nonsynonymous substitutions per nonsynonymous site to the number of synonymous substitutions per synonymous site for the protein-coding regions of homologous genes from related species. Each method implements different corrections for estimating "multiple hits" (i.e., more than one nucleotide substitution at the same site). Each method also uses different models for how DNA sequences change over evolutionary time. Thus, preferably, a combination of results from different algorithms is used to increase the level of sensitivity for detection of positively-selected genes and confidence in the result.

It is understood that the methods described herein could lead to the identification of soybean polynucleotide sequences that are functionally related to soybean protein-coding sequences. Such sequences may include, but are not limited to, non-coding sequences or coding sequences that do not encode proteins. These related sequences can be, for example, physically adjacent to the soybean protein-coding sequences in the soybean genome, such as introns or 5'- and 3'-flanking sequences (including control elements such as promoters and enhancers). These related sequences may be obtained via searching a public genome database such as GenBank or, alternatively, by screening and sequencing an appropriate genomic library with a protein-coding sequence as probe. Methods and techniques for obtaining non-coding sequences using related coding sequence are well known to one skilled in the art.

After candidate genes were identified, the nucleotide sequences of the genes in each orthologous gene pair were carefully verified by standard DNA sequencing techniques and then Ka/Ks analysis was repeated for each carefully sequenced candidate gene pair.

More specifically to this Example, the software ran through all possible pairwise comparisons between putative orthologs of every gene from cultivated soybean, *G. max*, as compared to the likely orthologs from the wild species, looking for high Ka/Ks ratios. The software BLASTed (in automated fashion) every mRNA sequence from cultivated soybean against every sequence in the transcriptome that was sequenced from a wild relative, for example, *G. pescadrensis*. The software then performed Ka/Ks analysis for each gene pair (i.e., each set of 'orthologs'), flagging the gene pairs with high Ka/Ks scores. The software then compared every *G max* sequence against every sequence of another wild relative, for example, *G. tabacina*, again by doing a series of BLASTs, and then sifting through for high Ka/Ks scores. It thus does this for the transcriptome sequence of all the wild species in succession. This gives a set of candidates (see below) for subsequent analysis.

The software next compared every gene sequence in the transcriptome of *G. pescadrensis* against every sequence of *G. tabacina*, again doing BLASTs, etc. It thus ultimately compared all of the expressed genes represented in the utilized cDNA libraries of every soybean species against all the genes of every other soybean species, both wild and cultivated, the goal being to find every gene that shows evidence of positive selection. While software was used to accomplish this analysis it can be accomplished by one skilled in the art using a calculator, i.e., it can all be "done by hand"—the software simply speeds things up.

The flagged gene pairs that emerged were then individually and carefully re-sequenced in the lab to check the accuracy of the original high-throughput reads; thus false positives were eliminated.

Next, every remaining candidate gene pair with a high Ka/Ks score was examined to determine if the comparison was truly orthologous, or just an artifactual false positive caused by a paralogous comparison.

Following are provided the nucleotide sequences of the orthologous genes that were definitely, positively selected based on this analysis. Information about the geographic locations from which each accession was originally collected, as well any other available data about each accession are also given below.

*Glycine microphylla* (SEQ ID NO: 4):

```
ttaattcatcactttcatcacccaatccact:cctctaattaacacccacc
aacaccatgGCTTCCCACTTCCTCAAATCCCTCCTTCTCCTCTCCACCTAT
GCCCTCACCATCTCAGCAGAATACACAGGCTTCGTGGGGACACTAGACCCA
AAGTCCATAGGCATACACCACAAGAAAACCCTAAGCCACTTCAGGTTCTAC
TGGCACGAAGTCTTCAGCGGAGAAAACCCCACAACGGTTAGAATCATTCCC
TCACTCCCCAAATACAACACAACCACAACCTTCGGTTCCGTTGGAATCTTT
GACAACACTTTAACCGTGGGACCTGAGGTGTACTCCAAGGTTGCCGGAAAA
GCCGAGGGCTTGTTTGCCTCCACGTCACAAACGCAGTTTAACCTGTTACTG
ATTTACAGCTTCGCGTTGACCCAAGGGAAGTACAACGGCAGCACCATCACG
TTCACGGGGAGGAGCCCCCTCTCGGAGAAGGTGAGGGAGCTGCCCATTGTT
GGTGGCAGTGGGGTCTTCAAATTTGCCACTGGGTATGTTGAGTCTAGGACG
CTAAGTTTTGATCCCCAAACGAGGAATAACACGGTTCAGTTCGACGTGTAT
ATTTACTATtgatgattattgaatgtgttttttacatgttgatgtgttaga
gctttggtgtgtgtcacttagtttcta
```

This sequence is from Accession PI505196 which was collected 30 Jul. 1983. Queensland, Australia. Locality: 5.4 km from road junction (Evelyn) towards Tumoulin. Latitude: 17 deg 32 min S (−17.53333333), Longitude: 145 deg 26 min E (145.43333333) Elevation: 900 meters.

Demonstrated to be resistant to SCN race 3 (Bauer, S., T. Hymowitz, and G. R. Noel. 2007. Soybean cyst nematode resistance derived from *Glycine tomentella* in amphiploid (*G. max×G. tomentella*) hybrid lines. *Nematropica* 37:277-285).

*Glycine pescadrensis* (SEQ ID NO: 5):

```
ataaattcttgcattaattcatcactttcatcacccaatccatttcctct
aattaacacccaccaaaaccatgGCTTCCCACTTCCTCAAATCCCTCCTT
CTCCTCTCCACCTATGCCCTCACCATCTCAGCAGAATACACAGGCTTCGT
GGGCACACTAGACCCAAAGTCCATAGGCATACACCACAAGAAAACCCTAA
ACCACTTCAGGTTCTACTGGCACGAAGTCTTCAGCGGAGAAAACCCCACA
TCGGTTAGAATCATTCCCTCACTCCCCAAATACAACACAACCACAACCTT
CGGTTCCGTTGGAATCTCTGACAACGCTTTAACCGTGGGACCTGAGGTGT
ACTCCAAGGTTGTCGGAAAAGCCGAGGGCTTGTTTGTCTCCACGTCACAA
ACGCAGTTTGACCTGTTACTGATTTACAACTTCGCGTTGACCCAAGGGAA
GTACAACGGCAGCACCATCACGTTCACGGGGAGGAGCCCCCTCTCGGAGA
AGGTGAGGGAGCTGCCCATTGTAGGTGGCAGTGGGGTCTTCAAATTTTCC
ACTGGGTATGTTGAGTCTAGGACGCTAAGTTTTGATCCCCAAACGAGGAA
TAACACGGTTCAGTTCGACGTGTATATTTACTATtgatgattattgaatg
tgtttttaccatgagatgtgttatagctttggtatgtgtcacttagttt
cta
```

This sequence is from Accession PI537287, which was collected 7 Apr. 1988. Taiwan. Locality: Military area, Sea Stride (Penghu Bridge), Paisha Island, Pescadores Islands. Latitude: 23 deg 40 min 0 sec N (23.66666667), Longitude: 119 deg 34 min 48 sec E (119.58). Elevation: 5 meters.

*Glycine tabacina* (New South Wales, Australia, SEQ ID NO: 6):

```
catcacccaatccact:cctctaattaacacccaccaacaccatgGCTTC
CCACTTCCTCAAATCCCTCCTTCTCCTCTCCACCTATGCCCTCACCATCT
CAGCAGAATACACAGGCTTCGTGGGGACACTAGACCCAAAGTCCATAGGC
ATACACCACAAGAAAACCCTAAGCCACTTCAGGTTCTACTGGCACGAAGT
CTTCAGCGGAGAAAACCCCACAACGGTTAGAATCATTCCCTCACTCCCCA
AATACAACACAACCACAACCTTCGGTTCCGTTGGAATCTTTGACAACACT
TTAACCGTGGGACCTGAGGTGTACTCTAAGGTTGCCGGAAAAGCCGAGGG
CTTGTTTGCCTCCACGTCACAAACGCAGTTTAACCTGTTACTGATTTACA
GCTTCGCGTTGACCCAAGGGAAGTACAACGGCAGCACCATCACGTTCACG
GGGAGGAGCCCCCTCTCGGAGAAGGTGAGGGAGCTGCCCATTGTTGGTGG
CAGTGGGGTCTTCAAATTTGCCACTGGGTATGTTGAGTCTAGGACGCTAA
GTTTTGATCCCCAAACGAGGAATAACACGGTTCAGTTCGACGTGTATATT
TACTATtgatgattattgaatgtgttttttacatgttgatgtgttagagc
tttggtgtgtgtcacttagtttcta
```

This sequence is from *G. tabacina* Accession PI446968, collected in: New South Wales, Australia, and some time prior to 1980. Locality: Toward west Wyalong, 35 km from Condobolin. Latitude: 33 deg 20 min S (−33.33333333), Longitude: 147 deg 8 min E (147.13333333) Elevation: 260 meters.

Demonstrated to be resistant to SCN race 3 (Bauer, S., T. Hymowitz, and G. R. Noel. 2007. Soybean cyst nematode resistance derived from *Glycine tomentella* in amphiploid (*G. max*×*G. tomentella*) hybrid lines. Nematropica 37:277-285).

*Glycine tabacina* (Taiwan, SEQ ID NO: 7):

cctacttcgatgcttcccccaccttataaattcttgcattaattcatcac
tttcatcacccaatccatttcctctaattaacacccaccaaaaccatgGC
TTCCCACTTCCTCAAATCCCTCCTTCTCCTCTCCACCTATGCCCTCACCA
TCTCAGCAGAATACACAGGCTTCGTGGGCACACTAGACCCAAAGTCCATA
GGCATACACCACAAGAAAACCCTAAACCACTTCAGGTTCTACTGGCACGA
AGTCTTCAGCGGAGAAAACCCCACATCGGTTAGAATCATTCCCTCACTCC
CCAAATACAACACAACCACAACCTTCGGTTCCGTTGGAATCTCTGACAAC
GCTTTAACCGTGGGACCTGAGGTGTACTCCAAGGTTGTCGGAAAAGCCGA
GGGCTTGTTTGTCTCCACGTCACAAACGCAGTTTGACCTGTTACTGATTT
ACAACTTCGCGTTGACCCAAGGGAAGTACAACGGCAGCACCATCACGTTC
ACGGGGAGGAGCCCCCTCTCGGAGAAGGTGAGGGAGCTGCCCATTGTAGG
TGGCAGTGGGGTCTTCAAATTTTCCACTGGGTATGTTGAGTCTAGGACGC
TAAGTTTTGATCCCCAAACGAGGAATAACACGGTTCAGTTCGACGTGTAT
ATTTACTATtgatgattattgaatgtgtttttccatgttgatgtgttat
agctttggtatgtgtcacttagtttcta This sequence is from *G. tabacina* Accession PI559281, collected in Penghu, Taiwan, 8 Apr. 1988. Locality: Airport (NE) on Chimei Island. Latitude: 23 deg 33 min 48 sec N (23.5633577), Longitude: 119 deg 37 min 41 sec E (119.628067).

Demonstrated to be resistant to SCN race 3 (Bauer, S., T. Hymowitz, and G. R. Noel. 2007. Soybean cyst nematode resistance derived from *Glycine tomentella* in amphiploid (*G. max*×*G. tomentella*) hybrid lines. Nematropica 37:277-285.)

*Glycine tomentella* (An alternate name for this species, used in some literature, is *G. latifolia*.) (Australia, SEQ ID NO: 8):

cacctacttcgatgcttcccccaccttataaattcttgcattaattcat
cactttcatcacccaatccatttcctctaattaacacccaccaaaaccat
gGCTTCCCACTTCCTCAAATCCCTCCTTCTCCTCTCCACCTATGCCCTCA
CCATCTCAGCAGAATACACAGGCTTCGTGGGCACACTAGACCCAAAGTCC
ATAGGCATACACCACAAGAAAACCCTAAACCACTTCAGGTTCTACTGGCA
CGAAGTCTTCAGCGGAGAAAACCCCACATCGGTTAGAATCATTCCCTCAC
TCCCCAAATACAACACAACCACAACCTTCGGTTCCGTTGGAATCTCTGAC
AACGCTTTAACCGTGGGACCTGAGGTGTACTCCAAGGTTGTCGGAAAAGC
CGAGGGCTTGTTTGTCTCCACGTCACAAACGCAGTTTGACCTGTTACTGA
TTTACAACTTCGCGTTGACCCAAGGGAAGTACAACGGCAGCACCATCACG
TTCACGGGGAGGAGCCCCCTCTCGGAGAAGGTGAGGGAGCTGCCCATTGT
AGGTGGCAGTGGGGTCTTCAAATTTTCCACTGGGTATGTTGAGTCTAGGA
TGCTAAGTTTTGATCCCCAAACGAGGAATAACACGGTTCAGTTCGACGTG
TATATTTACTATtgatgattattgaatgtgtttttccatgttgatgtgt
tatagctaggtatgtgtcacttagtttctatataagtttccama This sequence is from *G. tomentella* Accession PI 499946, collected in New South Wales, Australia. Locality: Delungra. Latitude: 29 deg 39 min 0 sec S (−29.65), Longitude: 150 deg 50 min E (150.83333333) Elevation: 600 meters.

Demonstrated to be resistant to SCN (Bauer, S., T. Hymowitz, and G. R. Noel. 2007. Soybean cyst nematode resistance derived from *Glycine tomentella* in amphiploid (*G. max*×*G. tomentella*) hybrid lines. *Nematropica* 37:277-285).

All of the above EG261 sequences from the wild relatives of *G. max* are all "copy A" (as given above for *G. max*). Copy A from each wild species has been strongly positively selected as compared to copy A of *G. max*. In addition, when compared to each other (i.e., not compared only to cultivated soybeans) EG261 copy A from each wild species examined has been strongly positively selected relative to each of the other wild species. This suggests that each wild species has likely been confronted by several different races of SCN, as well as by different species and even categories of pathogens (such as bacteria, fungi, insects, and nematodes) so that each wild species of soybean has thus likely evolved/achieved resistance to multiple SCN races.

Our demonstration of the clear episodes of positive selection in the wild soybean species, relative to each of the other wild species, suggests strongly that the orthologs of EG261 from each of these wild species is of value for creating SCN resistance in cultivated soybeans.

Example 3

Characterization of Orthologs of EG261 in Wild Soybean Species

Plants from wild, related species containing the orthologs identified according to Example 2 were assayed for their actual ability to confer resistance. In this example, wild soybean species of the genus *Glycine* were tested for their innate ability to resist challenge by soybean cyst nematode (SCN). Germplasm accessions were obtained from the National Plant Germplasm System (NPGS).

Seeds were geminated and seedlings were tested for SCN resistance in conical cone-tainers. (Niblack, T., Tylka, G. L., Arelli, P., Bond, J., Diers, B., Donald, P., Faghihi, J., Ferris, V. R., Gallo, K., Heinz, R. D., Lopez-Nicora, H., Von Qualen, R., Welacky, T., and Wilcox, J. 2009. A standard greenhouse method for assessing soybean cyst nematode resistance in soybean: SCE08 (standardized cyst evaluation 2008). Online. *Plant Health Progress* doi:10.1094/PHP-2009-0513-01-RV.)

For those species that were confirmed to have innate ability to resist SCN, RNAs from several tissues (including root, stem, and leaf) were flash-frozen and both genomic DNA and RNA were prepared from the frozen tissues. RNAs from multiple tissues from each plant then were pooled for subsequent construction of cDNA libraries (one library per species). High-throughput 454 Titanium sequencing was performed for each cDNA library. It is noted, however, that any suitable high-throughput sequencing format would have been acceptable and using this particular method was not critical to the success of these experiments.

The resulting transcriptome sequence datasets for each species were analyzed in order to identify any positively selected transcripts using proprietary analysis software of Evolutionary Genomics, Inc.

Candidate genes were verified using protocols in transgenic soybean plants that test for effectiveness in protecting the transformed soybean plants from attack by the SCN organism as well as the *Phytophthora* fungus. We report here results from experiments where RNAi is used to knock out EG261 in an SCN-resistant line (Fayette). After knockout, the normally resistant Fayette line became SCN sensitive. The control for this experiment was RNAi silencing of EG261 in the Williams 82, which is SCN-sensitive: no difference in sensitivity was observed after silencing of EG261 in this line. These experiments are interpreted to mean that resistance to SCN is conferred by the EG261 gene; if one knocks out the EG261 allele in SCN-resistant lines, the result is that SCN resistance is then lost. (Interestingly, the allele of EG261 in the SCN-sensitive William 82 line is already either non-functional or at least not very effective in conferring SCN-resistance, so that silencing of the EG261 allele does not change the SCN-sensitive phonotype of Williams 82.) Importantly, the resistant line (Fayette) is one that was created by cross-breeding to soybean land-races that display SCN-resistance. (It is believed that the land-races became SCN-resistant because of introgression with wild SCN-resistant soybean species.)

Example 4

Silencing of EG261 Eliminates the SCN-Resistant Phenotype in SCN-Resistant Soybeans Construct pG2RNAi2 was produced carrying a hairpin to silence the target gene EG261 and the constructs were used to produce transgenic roots in the soybean variety 'Fayette.' Two replications of SCN demographics experiments were conducted for the 'Fayette' transgenic roots. For a detailed description of the test protocol used herein, see Melito et al. (2010) A nematode demographics assay in transgenic roots reveals no significant impacts of the Rhg1 locus LRR-Kinase on soybean cyst nematode resistance, BMC Plant Biology 10:104, 14 pages.

Approximately 250 hatched J2 nematodes were placed near the tip of each transgenic soybean root, with root identities blinded by assignment of randomized numbers. After two weeks, roots were fixed and stained with acid fuchsin and the number and growth stage of all nematodes within or attached to each root was assessed (average 76 total nematodes per root).

In the first of two replicate experiments, in the 'Fayette' transgenic roots, expression levels of EG261 are on average about 12% of Fayette wild-type. 11 of 14 transgenic roots had silencing >50% and were included; 3 roots were excluded due to poor silencing. In the second replicate experiment, tissue was saved but silencing was not checked. Therefore, all of the data was included (hence the phenotypic impact of silencing may be masked a bit due to inclusion of some non-silenced roots in the data that was obtained).

Data show significant shift toward susceptibility (FIG. 1). Bars show the proportion of nematode population on each root that advanced past the J2 stage (mean±std.error). F: Fayette (SCN-resistant); W: Williams 82 (SCN-susceptible); EV: transformed with empty vector; hp: transformed with EG261 hairpin gene silencing construct; Ox: transformed with construct expressing Glyma01g31770 under control of strong *G. max* ubiquitin promoter. ANOVA P value for similarity of means is 0.005 for F EV compared to F hp, and 0.97 for W EV compared to W Ox.

The control for this experiment was RNAi silencing of EG261 in the soybean cultivar Williams 82, which is SCN-sensitive: no difference in sensitivity was observed after silencing of EG261 in this line. These experiments were interpreted to mean that resistance to SCN is conferred by the EG261 gene; if one knocks out the EG261 allele in SCN-resistant lines, the result is that SCN resistance is then lost. However, the allele of EG261 in the sensitive William 82 line is already either non-functional or at least not very effective in conferring SCN-resistance, so that silencing of the EG261 allele does not change the SCN-sensitive phonotype of Williams 82. Importantly, the resistant line (Fayette) is one that was created by cross-breeding to soybean land-races that display SCN-resistance. (It is believed that the land-races became SCN-resistant because of introgression with wild SCN-resistant soybean species.) This is strong evidence for the role of EG261 in influencing/controlling SCN resistance in soybeans.

Example 5

Transformation of Tomato with EG261

'Big Boy' tomato plants can be transformed with a construct containing EG261 using standard transformation technology for tomato plants. See, e.g., Antonio Di Matteo, Maria Manuela Rigano, Adriana Sacco, Luigi Frusciante and Amalia Barone (2011). Genetic Transformation in Tomato: Novel Tools to Improve Fruit Quality and Pharmaceutical Production, Genetic Transformation, Prof. MarÃa Alvarez (Ed.), ISBN: 978-953-307-364-4, InTech.

Transformation of tomato plants with a construct containing EG261 can be accomplished with either the cultivated/ the wild soybean orthologs included in this patent, or with the tomato ortholog (SEQ ID NO 16) of the EG261 gene.

The transformed tomato plants can be tested for disease resistance as compared to the untransformed, control 'Big Boy' tomato plants.

Diseases which can be tested for conferred or enhanced pathogen tolerance and/or resistance as a result of such transformation include root rot caused by *Rhizoctonia solani, Fusarium solani* and *Sclerotiumrolfsii*. For procedures used to test for tolerance/resistance to these root diseases see, e.g., Abd-El-Kareem, F., Nehal S. El-Mougy, Nadia G. El-Gamal and Y. O. Fotouh (2006) Use of Chitin and Chitosan Against Tomato Root Rot Disease under Greenhouse Conditions Research, Journal of Agriculture and Biological Sciences, 2(4): 147-152.

The transformed tomato plants showing conferred and/or enhanced resistance to one or more of these root diseases can be tested to confirm the presence of EG261 by using one or more of the following procedures: (a) isolating nucleic acid molecules from said plant and amplifying sequences homologous to the EG261 polynucleotide; (b) isolating nucleic acid molecules from said plant and performing a Southern hybridization to detect the EG261 polynucleotide; (c) isolating proteins from said plant and performing a Western Blot using antibodies to a protein encoded by the EG261 polynucleotide; and/or (d) demonstrating the presence of mRNA sequences derived from a EG261 polynucleotide mRNA transcript and unique to the EG261 polynucleotide.

Example 6

Tomato Breeding with Tomato Plants Expressing EG261

A 'Big Boy' tomato plant with a conferred copy of the coding sequence for EG261 as obtained in Example 6 can be crossed to a plant of the 'Early Girl' variety and the resultant progeny can be tested for tolerance/resistance to the three root diseases.

The presence of the EG261 polynucleotide can be confirmed in the resultant 'Early Girl' progeny according to the procedures set forth in Example 5.

In a further procedure, the transformed 'Early Girl' tomato plant can be backcrossed one or more times to 'Early Girl' to produce a near isogenic or isogenic 'Early Girl' tomato with the coding sequence for EG261.

Example 7

Transformation of Maize with EG261

'B73' and/or 'Mo17' inbred maize plants can be transformed with a construct containing EG261 using standard transformation technology for maize. See, e.g., Sidorov and Duncan, 2008 (*Agrobacterium*-Mediated Maize Transformation: Immature Embryos Versus Callus, Methods in Molecular Biology, 526:47-58); Frame et al., 2002 (*Agrobacterium tumefaciens*-Mediated Transformation of Maize Embryos Using a Standard Binary Vector System, Plant Physiology, May 2002, Vol. 129, pp. 13-22); and, Ahmadabadi et al., 2007 (A leaf-based regeneration and transformation system for maize (*Zea mays* L.), TransgenicRes. 16, 437-448).

Transformation of maize plants with a construct containing EG261 can be accomplished with either the cultivated/ the wild soybean orthologs included in this patent, or with the maize ortholog of these EG261 genes.

The transformed maize plants can be tested for nematode/ pest resistance as compared to the untransformed, control 'B73' or 'Mo17' maize plants. For procedures used to test for tolerance/resistance to nematodes see, e.g., Sasser, et al. (1984) Standardization of Host Suitability Studies and Reporting of Resistance to Root-Knot Nematodes, Crop Nematode Research & Control Project (CNRCP), a cooperative publication of The Department of Plant Pathology, North Carolina State University and the United States Agency for International Development, North Carolina State University Graphics, Raleigh, N.C., 10 pages; and, Cook, R. and K. Evans (1987) Resistance and Tolerance, In: Principles and practice of nematode control in plants, R. H. Brown and B. R. Kerry (editors), pg. 179-231.

The transformed maize plants showing conferred and/or enhanced resistance to one or more races of nematodes can be tested to confirm the presence of EG261 by using one or more of the following procedures: (a) isolating nucleic acid molecules from said plant and amplifying sequences homologous to the EG261 polynucleotide; (b) isolating nucleic acid molecules from said plant and performing a Southern hybridization to detect the EG261 polynucleotide; (c) isolating proteins from said plant and performing a Western Blot using antibodies to a protein encoded by the EG261 polynucleotide; and/or (d) demonstrating the presence of mRNA sequences derived from a EG261 polynucleotide mRNA transcript and unique to the EG261 polynucleotide.

The transformed maize plants with confirmed tolerance and/or resistance to one or more nematode races can be maintained by self-pollinating the plants, harvesting the resultant seed and growing the resistant plants from such harvested seed.

Example 8

Maize Breeding with Maize Plants Expressing EG261

A 'B73' or 'Mo17' corn inbred plant with a conferred copy of the coding sequence for EG261 as obtained in Example 7 can be crossed to a transformed or non-transformed inbred 'Mo17' 'B73' plant, respectively, and the resultant hybrid F1 progeny can be tested for tolerance/ resistance to nematodes.

The presence of the EG261 polynucleotide can be confirmed in the resultant hybrid progeny according to the procedures set forth in Example 7.

In a further procedure, the transformed hybrid maize plant can be backcrossed one or more times to its recurrent parent (i.e., either 'B73' or 'Mo17' as applicable) to produce a near isogenic or isogenic maize inbred with the coding sequence for EG261.

Example 9

EG261 Overexpression

Overexpression of EG261 was tested using two replications of the soybean variety 'Williams 82.' For a detailed description of the test protocol used herein, see Melito et al. (2010) A nematode demographics assay in transgenic roots reveals no significant impacts of the Rhg1 locus LRR-Kinase on soybean cyst nematode resistance, BMC Plant Biology 10:104, 14 pages.

Expression level in "overexpression roots" was found to be 4.3-fold greater, however native EG261 gene is expressed very highly, only 5-fold less than ubiquitin, so these expression levels appear to be consistent with expectations.

Data show no significance difference from normal 'Williams 82' (i.e., without overexpression of EG261), but these inconclusive results are probably because expression levels were not as rigorously controlled as was desirable.

Example 10

Identification of Orthologs of EG261 in Other Plant Species

Using analysis techniques derived from molecular evolutionary biology, gene sequences from the cultivated (i.e., domesticated) soybean, *Glycine max*, were used to identify orthologous genes from other plant species. The following table provides the SEQ ID Nos. of the nucleotide sequences of genes that are orthologous to the positively selected soybean EG261 copy A gene. Predicted amino acid sequences, and information about the geographic locations from which each accession was originally collected, as well any other available information about each accession are also given below.

| Plant species | Nucleotide sequence SEQ ID NO. | Amino acid sequence SEQ ID NO. | Geographic locations and accession information |
|---|---|---|---|
| *Solanum lycopersicum* (or *Solanum esculentum*) | 16 | 25 | cultivated tomato |
| *Solanum peruvianum* | 17 | 26 | Peruvian tomato, a.k.a., Peruvian nightshade |
| *Solanum chmielewskii* | 18 | 27 | |
| *Solanum habrochaites* | 19 | 28 | |
| *Solanum corneliomulleri* | 20 | 29 | |
| *Capsicum annuum* | 21 | 30 | chili pepper |
| *Capsicum annuum* | 22 | 31 | hot pepper |
| *Solanum melongena* | 23 | 32 | eggplant |
| *Solanum tuberosum* | 24 | 33 | potato |
| *Phaseolus vulgaris* | 34 | 37 | Common bean varieties "Blue Lake" (a bush type snap bean that was developed from the Blue Lake Pole bean), Henderson Bush Lima Bean (bean variety dates to 1885), Dixie Speckled Butterpea Lima Bean, Hidatsa Red Indian, and Kabouli Black Garbanzo Asian Bean (collected in Kabul, Afghanistan) |
| *Phaseolus vulgaris* | 35 | 38 | Common bean variety Scarlet Emperor (dates at least to 1750, was originally from Central America) |
| *Phaseolus vulgaris* | 36 | 39 | Jacob's Cattle Bean |
| *Coffea arabica* | 40 | 43 | coffee plant, Allele A |
| *Coffea arabica* | 41 | 44 | coffee plant, Allele B |
| *Capsicum annuum* | 42 | 45 | cultivated pepper ("ornamental" pepper) |
| *Zea mays* | 46 | 51 | |
| *Sorghum* sp. | 47 | 52 | |
| *Oryza sativa,* | 48 | 53 | |
| *Triticum* sp. | 49 | 54 | |
| *Hordeum* sp. | 50 | 55 | |
| *Gossypium hirsutum* | 56 | 57 | Variety FJ600364 |
| *Gossypium hirsutum* | 58 64 65 | 59 | Variety FJ600365 |
| *Vigna unguiculata* (Cowpea) | 60 | 61 | Monkey tail (collected in Africa) |
| *Vigna unguiculata* (Cowpea) | 62 | 63 | Pea, varieties Risina Del Trasiorfino (collected in Perugia, Italy) and Shanty Pea (collected in South Carolina, USA) |

Example 11

Characterization of Orthologs of EG261 Isolated from Additional Plant Species The gene orthologs from wild, related species can be assayed for their ability to confer resistance. (In this example, corresponding wild plant species can also be tested for their innate ability to resist challenge by one or more parasitic nematodes. Seeds are germinated and seedlings are tested for resistance to one or more parasitic nematodes by any suitable standard testing methods.)

For each species examined, the species-specific ortholog of EG261 can be analyzed for evidence of positive selection, using proprietary analysis software of Evolutionary Genomics, Inc. Orthologs that appear to have been positively selected can then be assayed for the ability to confer resistance as described for soybean (*G. max*) in Examples 3 and 4.

Example 12

Silencing of EG261 Eliminates the Nematode Resistant Phenotype in Nematode-Resistant Plants Constructs are produced carrying an RNAi silencing DNA fragment (e.g., a hairpin, a double strand, an antisense, an inverted repeat, etc.) targeting each one of the EG261 orthologs isolated in Example 10. These constructs are used to produce transgenic plants for each plant species.

Hatched J2 nematodes are placed near the tip of each transgenic plant. After a time sufficient for nematode infection, roots are fixed and stained with acid fuchsin and the number and growth stage of all nematodes within or attached to each root is assessed.

Data shows significant shift toward susceptibility in one or more transgenic plant species compared to their corresponding wild-type nematode-resistant control plant species.

Example 13

Introducing EG261 Orthologs into Heterologous Plant Species

In some embodiments, the EG261 orthologs conferring nematode resistance isolated according to the present invention from one plant species can be introduced into a nematode-susceptible plant of the same species in order to create nematode resistance into the plant.

However, in some other embodiments, the EG261 orthologs of the present invention isolated from one plant species can be introduced into a nematode-susceptible plant of different species of the same genus, or a plant species of different genus in order to introduce nematode resistance into the plant.

For example, a gene encoding any one of the proteins of SEQ ID NOs: 9-15 which were isolated from soybean can be also introduced into other plant species, such as Solanaceae species (e.g., *Solanum lycopersicum, Solanum chemielewskii, Solanum habrochaites, Solanum corneliomulleri, Capsicum annuum, Solanum melongena, Solanum tuberosum*), *Phaseolus vulgaris, Vigna unguiculata, Coffee arabica, Zea mays, Sorghum* spp., *Oryza sativa, Triticum* spp. *Hordeum* spp., *Gossypium hirsutum*, and *Heliotropium curassavicum*. Similarly, a gene encoding anyone of the proteins of SEQ ID NOs: 25, 26, 27, 28, 29, 30, 31, 32, 33, 37, 38, 39, 43, 44, 45, 51, 52, 53, 54, 55, 57, 59, 61, 63, 64, and 65 can be introduced into other plant species.

Following the methods described in Example 11, plant species comprising a heterologous EG261 gene or an ortholog thereof are created and tested. The results will confirm that one or more EG261 genes or orthologs thereof can introduce nematode resistance when heterologously expressed in a plant species different from the plant species from which the heterologous EG261 genes or orthologs thereof were isolated.

Example 14

Introducing Nematode Resistance into Nematode-Susceptible Plants

This example shows that a gain-of-SCN-resistance phenotype in a previously SCN-sensitive soybean cultivar was observed when the EG261 ortholog from a wild SCN-resistant soybean species (*Glycine pescadrensis*) was transformed into the SCN-sensitive 'Williams 82' soybean cultivar. That is, by using transformation (knock-in) a cultivated SCN-sensitive soybean cultivar becomes SCN resistant. In fact, the level of resistance achieved is roughly equivalent to that of the only known commercially-available SCN-resistant soybean cultivar. The results indicate that, by using an EG261 ortholog isolated from a nematode resistant plant to transform a plant that one can achieve SCN suppression, to near zero in some cases, in that plant.

More specifically, EG261 orthologs from 2 species, (*G. pescadrensis* and *G. microphylla*) were tested.

The *G. pescadrensis* EG261 ORF with 5' and 3' UTR was PCR amplified from cDNA and ligated into pCR8. A NOS terminator was cloned into pSM101-Gmubi to create an over-expression construct with a strong promoter and terminator. The *G. pescadrensis* EG261 ORF was excised from pCR8 (5' PstI, 3' BamHI) and ligated into pSM101-Gmubi-NOS. Vector pSM101-Gmubi-*G. pescadrensis* EG261-NOS was verified by sequencing.

Similarly, the *G. microphylla* EG261 ORF with UTR was PCR-amplified from cDNA and ligated into pCR8. A NOS terminator was cloned into pSM101-Gmubi to create an over-expression construct with a strong promoter and terminator. The *G. microphylla* EG261 ORF was excised from pCR8 (5' PstI, 3' BamHI) and ligated into pSM101-Gmubi-NOS. Vector pSM101-Gmubi-*G. microphylla* EG261-NOS was verified by sequencing. These constructs were transformed into *Agrobacterium rhizogenes*. Cotyledons of SCN-susceptible genotype ('Williams 82') and SCN-resistant genotype ('Fayette') were germinated and then transformed with *Agrobacterium* containing these EG261 over-expression constructs. Hairy roots emerged from these cotyledons and GFP positive roots (those expressing the genes of interest as well as an empty control vector) were harvested and subcultured (approximately 10 roots per genotype with each construct). SCN cysts were crushed and eggs hatched to produce infective juveniles (J2). Approximately 220 sterile J2 were placed onto these transgenic hairy roots.

The second-stage juvenile, or J2, is the only life stage that soybean cyst nematode can penetrate roots. The first-stage juvenile occurs in the egg, and third- and fourth-stages occur in the roots. The J2 enters the root moving through the plant cells to the vascular tissue where it feeds. The J2 induces cell division in the root to form specialized feeding sites. As the nematode feeds, it swells. The female swells so much that her posterior end bursts out of the root and she becomes visible to the naked eye. In contrast, the adult male regains a wormlike shape, and he leaves the root in order to find and fertilize the large females. The female continues to feed as she lays 200 to 400 eggs in a yellow gelatinous matrix, forming an egg sac which remains inside her. She then dies and her cuticle hardens forming a cyst. The eggs may hatch when conditions in the soil are favorable, the larvae developing inside the cyst and the biological cycle repeating itself. There are usually three generations in the year. In the autumn or in unfavorable conditions, the cysts containing dormant larvae may remain intact in the soil for several years. The juvenile molts to the J3 and begins enlarging as the reproductive system develops. Nematodes which become females are no longer able to leave the root. They continue to enlarge as they go through the J3 and J4 stages. During this time, cells around the head of the nematode enlarge to form nurse cells or giant cells. For root-knot nematode, galls will typically develop on the root. Upon becoming adults, root-knot nematodes will begin to lay eggs (up to several hundred) which are contained in a gelatinous matrix at the posterior end of the body. The egg mass may be within the root or partly or wholly exposed on the root surface while the swollen body of the female remains within the root. Therefore, we count the J2 and J3 numbers to assess the extent of the nematode infestation.

As mentioned above, variety 'Williams' was used as a SCN susceptible cultivar and variety 'Fayette' was used as a SCN-resistant control. Experimental results are provided in the table below. The testing methods used herein are described in Melito et al. (BMC Plant Biology, 2010, 10:104, incorporated herein by reference in its entirety). In the following table, "EV" refers to 'empty vector', i.e., a control plant that has been transformed with a vector construct that lacks the experimental gene but that otherwise consists of the complete vector. "OX" refers to 'overexpression', i.e., those experimental plants in which the vector contains the experimental EG261 ortholog, and the experimental knock-in gene is actively expressed at high levels. "Will" refers to the SCN-sensitive Williams 82 soybean cultivar, while "Fay" refers to the normally SCN-resistant soybean cultivar. "Mic" refers to the EG261 ortholog derived from *G. microphylla*, while "Pesc" refers to the EG261 ortholog derived from *G. pescadrensis*.

| Sample | J2 | J3 (and >+ Males) | Notes | J3 & Above/Total (J2 + J3 and Above) |
|---|---|---|---|---|
| 1 | 32 | 13 | | 0.289 |
| 2 | 38 | 7 | | 0.156 |
| 3 | 8 | 9 | | 0.529 |
| 4 | 24 | 19 | 3 males | 0.442 |
| 5 | 11 | 3 | | 0.214 |
| 6 | 14 | 19 | | 0.576 |
| 7 | 19 | 12 | Confusing | 0.387 |
| 8 | 20 | 3 | 2 males | 0.130 |
| 9 | 16 | 25 | | 0.610 |
| 10 | 22 | 27 | 2 males | 0.551 |
| 11 | 8 | 6 | | 0.429 |
| 12 | 10 | 9 | | 0.474 |
| 13 | 30 | 10 | 6 males | 0.250 |
| 14 | 38 | 4 | | 0.095 |
| 15 | 22 | 5 | | 0.185 |
| 16 | 50 | 41 | | 0.451 |
| 17 | 37 | 21 | | 0.362 |
| 18 | 32 | 13 | | 0.289 |
| 19 | 4 | 9 | | 0.692 |
| 20 | 18 | 20 | | 0.526 |
| 21 | 4 | 16 | | 0.800 |
| 22 | 5 | 20 | | 0.800 |
| 23 | | | | |
| 24 | 6 | 5 | Faint stain | 0.455 |
| 25 | 32 | 16 | | 0.333 |
| 26 | 8 | 16 | | 0.667 |
| 27 | 8 | 9 | Faint stain | 0.529 |
| 28 | 9 | 5 | | 0.357 |
| 29 | 8 | 11 | | 0.579 |
| 30 | 14 | 5 | | 0.263 |
| 31 | 10 | 23 | 8 males | 0.697 |
| 32 | 40 | 9 | | 0.184 |
| 33 | 3 | 10 | | 0.769 |
| 34 | 8 | 13 | | 0.619 |
| 35 | 11 | 5 | Faint - Not confident at all | 0.313 |
| 36 | 3 | 7 | | 0.700 |
| 37 | 2 | 9 | | 0.818 |
| 38 | 5 | 7 | | 0.583 |
| 39 | 3 | 10 | | 0.769 |
| 40 | 7 | 7 | | 0.500 |
| 41 | 4 | 11 | | 0.733 |
| 42 | 8 | 6 | Faint, hard to count | 0.429 |
| 43 | 27 | 9 | | 0.250 |
| 44 | 6 | 11 | | 0.647 |
| 45 | 15 | 9 | | 0.375 |
| 46 | 67 | 20 | | 0.230 |

| | J3/Total | SE |
|---|---|---|
| Williams EV (45, 37, 36, 14, 28, 44, 35, 34, 9, 11, 41, 6, 10, 21, 4) | 0.551 | 0.052 |
| Will Mic OX (19, 42, 31, 20, 26, 39, 22, 12, 7, 40, 30, 3, 47, 17, 23) | 0.546 | 0.043 |
| Will Pesc OX (15, 48, 2, 33, 1, 18, 13, 16, 5) | 0.325 | 0.064 |
| Fay EV (8, 27, 43, 25, 46, 29, 38, 24) | 0.337 | 0.059 |

Examination of the results make clear that transformation with the EG261 ortholog from *G. pescadrensis* causes the normally SCN-sensitive Williams 82 cultivar to acquire a level of SCN-resistance that approximates that of the SCN-resistant cultivar Fayette. Although the *G. microphylla* ortholog didn't appear to show obvious SCN suppression in the initial assessment, this may not rule out the effectiveness of the *G. microphylla* EG261 ortholog, given the number of variables that can affect transformation experiments. (We are repeating this first-pass experiment for the *G. microphylla* ortholog.) In contrast, the EG261 ortholog from *G. pescadrensis* is clearly capable of conferring resistance to SCN when introduced into SCN-sensitive soybean plants. We are currently investigating the effectiveness of EG261 orthologs from additional wild soybean relatives that are SCN tolerant. Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, patent publications, and nucleic acid and amino acid sequences cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. A transgenic soybean plant, plant part, plant cell, or plant tissue culture comprising a construct comprising a nucleic acid sequence encoding an EG261 polypeptide having at least 95% sequence identity to SEQ ID NO: 11, wherein said transgenic soybean plant, or a transgenic soybean plant produced from said transgenic plant part, plant cell, or plant tissue culture, expresses said EG261 polypeptide, and has enhanced tolerance and/or resistance to soybean cyst nematodes (SCN) compared to control soybean plants.

2. The transgenic soybean plant, plant part, plant cell, or plant tissue culture of claim 1, wherein the construct further comprises a gene termination sequence.

3. The transgenic soybean plant, plant part, plant cell, or plant tissue culture of claim 2, wherein the gene termination sequence is a nopaline synthase (NOS) terminator.

4. The transgenic soybean plant, plant part, plant cell, or plant tissue culture of claim 1, wherein the construct is an overexpression construct.

5. The transgenic soybean plant, plant part, plant cell, or plant tissue culture of claim 4, wherein the overexpression construct comprises a gene termination sequence.

6. A method for producing a transgenic soybean plant having enhanced tolerance and/or resistance to soybean cyst nematode, said method comprising:
  (i) transforming a soybean plant cell with a construct comprising a nucleic acid sequence encoding an EG261 polypeptide having at least 95% identity to SEQ ID NO: 11; and
  (ii) cultivating the transgenic soybean cell under conditions conducive to regeneration and mature plant growth;
wherein the transgenic soybean plant regenerated from said transgenic plant cell expresses said EG261 polypeptide, and has enhanced tolerance and/or resistance to soybean cyst nematodes compared to control soybean plants.

7. The method of claim 6, wherein the construct is an overexpression construct.

8. A method of producing hybrid soybean seed, said method comprising crossing the transgenic soybean plant of claim 1 with another soybean plant, and harvesting a resultant seed, wherein the resultant seed comprises the nucleic acid sequence encoding the EG261 polypeptide.

9. A hybrid soybean plant, or part thereof, produced by growing the seed of claim 8.

10. A Progeny plant of the soybean plant produced by the seed produced by the method of claim 8, wherein the progeny soybean plant has enhanced tolerance and/or resistance to soybean cyst nematodes compared to an control soybean plant, wherein the progeny plant comprises the nucleic acid encoding the EG261 polypeptide.

11. A method of breeding soybean plants to produce plants with enhanced tolerance and/or resistance to soybean cyst nematodes, said method comprising:
   (i) making a cross between a first transgenic soybean plant of claim 1 with a second plant to produce an F1 plant;
   (ii) backcrossing the F1 plant to the second plant; and
   (iii) repeating the backcrossing step one or more times to generate a near isogenic or isogenic line,
wherein the construct comprising the nucleic acid sequence encoding the EG261 polypeptide is integrated into the genome of the second plant and the near isogenic or isogenic line derived from the second plant with the nucleic acid sequence encoding the EG261 polypeptide has enhanced pathogen tolerance and/or resistance to soybean cyst nematodes compared to that of the second plant without said nucleic acid sequence.

12. The method of claim 11, wherein the second plant is Glycine max.

13. The transgenic soybean plant, plant part, plant cell, or plant tissue culture of claim 1, wherein the nucleic acid sequence encodes an EG261 polypeptide having at least 97% sequence identity to SEQ ID NO: 11.

14. The transgenic soybean plant, plant part, plant cell, or plant tissue culture of claim 1, wherein the nucleic acid sequence encodes an EG261 polypeptide having at least 98% sequence identity to SEQ ID NO: 11.

15. The transgenic soybean plant, plant part, plant cell, or plant tissue culture of claim 1, wherein the nucleic acid sequence encodes an EG261 polypeptide having at least 99% sequence identity to SEQ ID NO: 11.

16. The transgenic soybean plant, plant part, plant cell, or plant tissue culture of claim 1, wherein the nucleic acid sequence encodes an EG261 polypeptide having at least 100% sequence identity to SEQ ID NO: 11.

17. The method for producing a transgenic soybean plant having enhanced tolerance and/or resistance to soybean cyst nematodes of claim 6, wherein the nucleic acid sequence encodes an EG261 polypeptide having at least 97% sequence identity to SEQ ID NO: 11.

18. The method for producing a transgenic soybean plant having enhanced tolerance and/or resistance to soybean cyst nematodes of claim 6, wherein the nucleic acid sequence encodes an EG261 polypeptide having at least 98% sequence identity to SEQ ID NO: 11.

19. The method for producing a transgenic soybean plant having enhanced tolerance and/or resistance to soybean cyst nematodes of claim 6, wherein the nucleic acid sequence encodes an EG261 polypeptide having at least 99% sequence identity to SEQ ID NO: 11.

20. The method for producing a transgenic soybean plant having enhanced tolerance and/or resistance to soybean cyst nematodes of claim 6, wherein the nucleic acid sequence encodes an EG261 polypeptide having at least 100% sequence identity to SEQ ID NO: 11.

\* \* \* \* \*

SEQUENCE LISTING

<160> NUMBER OF SEQ ID NOS: 65

<210> SEQ ID NO 1
<211> LENGTH: 755
<212> TYPE: DNA
<213> ORGANISM: Glycine max

<400> SEQUENCE: 1

| | | | | | | |
|---|---|---|---|---|---|---|
| agcaagagat | gctcaaaccc | aaattcacct | acttcgatgc | ttcccccacc | ttataaattc | 60 |
| ttgcattaat | ttaccacttt | catcacccaa | tccacttcct | ctaattgaca | cccacctaaa | 120 |
| ccatggcttc | ccacttcctc | aaatccctcc | ttctcctctc | acctatgcc | ctcaccatct | 180 |
| cagcagaata | cacaggcttc | gtgggaacac | tagacccaaa | gtccataggc | atacaccaca | 240 |
| agaaaaccct | aagccacttc | aggttctact | ggcacgaagt | cttcagcgga | gaaaacccca | 300 |
| catcggttag | aatcattccc | tcactcccca | aatacaacgc | aaccacaacc | ttcggctccg | 360 |
| ttggaatctt | tgacacccct | ttaaccgtgg | gacctgaggt | gtactccaag | gttgtcggaa | 420 |
| aagccgaggg | cttgtttgcc | tccacgtcac | aaacgcagtt | tgacctgtta | ctgatttaca | 480 |
| acttcgcgtt | gacccaaggg | aagtacaacg | gcagcaccat | cacgttcacg | ggaggagcc | 540 |
| ccctctcgga | gaaggtgagg | gagctgccca | ttgttggtgg | tagtggggtc | ttcaaatttg | 600 |
| ccactgggta | tgttgagtct | aggacgctaa | gttttgatcc | ccaaacaagg | aataacacgg | 660 |
| ttcagttcga | cgtgtatatt | tactattgat | gattattgaa | tgtgtttttt | tcatgttgat | 720 |
| gcgttatcgc | tttggtctgt | ctcacctagt | ttcta | | | 755 |

<210> SEQ ID NO 2
<211> LENGTH: 567
<212> TYPE: DNA
<213> ORGANISM: Glycine max

<400> SEQUENCE: 2

| | | | | | | |
|---|---|---|---|---|---|---|
| atggcttccc | acttcctcaa | atccctcctt | ctcctctcca | cctatgccct | caccatctca | 60 |
| gcagaataca | caggcttcgt | gggaacacta | gacccaaagt | ccataggcat | acaccacaag | 120 |
| aaaaccctaa | gccacttcag | gttctactgg | cacgaagtct | tcagcggaga | aaaccccaca | 180 |
| tcggttagaa | tcattccctc | actccccaaa | tacaacgcaa | ccacaacctt | cggctccgtt | 240 |
| ggaatctttg | acaccccttt | aaccgtggga | cctgaggtgt | actccaaggt | tgtcggaaaa | 300 |
| gccgagggct | tgtttgcctc | cacgtcacaa | acgcagtttg | acctgttact | gatttacaac | 360 |
| ttcgcgttga | cccaagggaa | gtacaacggc | agcaccatca | cgttcacggg | gaggagcccc | 420 |
| ctctcggaga | aggtgaggga | gctgcccatt | gttggtggta | gtggggtctt | caaatttgcc | 480 |
| actgggtatg | ttgagtctag | gacgctaagt | tttgatcccc | aaacaaggaa | taacacggtt | 540 |
| cagttcgacg | tgtatattta | ctattga | | | | 567 |

<210> SEQ ID NO 3
<211> LENGTH: 748
<212> TYPE: DNA
<213> ORGANISM: Glycine max

<400> SEQUENCE: 3

| | | | | | | |
|---|---|---|---|---|---|---|
| atcacccaat | ccacttcctc | taattgacac | ccacctaaac | catggcttcc | cacttcctca | 60 |
| aatccctcct | tctcctctcc | acctatgccc | tcaccatctc | agcagaatac | acaggcttcg | 120 |
| tgggaacact | agacccaaag | tccataggca | tacaccacag | aaaaccctaa | gccacttcag | 180 |
| gttctactgg | cacgaagtct | tcagcggaga | aaaccccac | atcggttaga | atcattccct | 240 |

```
cactccccaa atacaacgca accacaacct tcggctccgt tggaatcttt gacacccctt    300
taaccgtggg acctgaggtg tactccaagg ttgtcggaaa agccgagggc ttgtttgcct    360
ccacgtcaca aacgcagttt gacctgttac tgatttacaa cttcgcgttg acccaaggga    420
agtacaacgg cagcaccatc acgttcacgg ggaggagccc cctctcggag aaggtgaggg    480
agctgcccat tgttggtggt agtggggtct tcaaatttgc cactgggtat gttgagtcta    540
ggacgctaag ttttgatccc caaacaagga ataacacggt tcagttcgac gtgtatattt    600
actattgatg attattgaaa gtgtttttt catgttgatg cgttatcgct ttggtctgtc    660
tcacctagtt tctacataag tttcctcttt tgagggcatg tggtgtcatg aataaagtc    720 atctttgggc aaaaaaaaaa aaaaaaaa                                       748

<210> SEQ ID NO 4
<211> LENGTH: 689
<212> TYPE: DNA
<213> ORGANISM: Glycine microphylla

<400> SEQUENCE: 4
ttaattcatc actttcatca cccaatccac tcctctaatt aacacccacc aacaccatgg     60
cttcccactt cctcaaatcc ctccttctcc tctccaccta tgccctcacc atctcagcag    120
aatacacagg cttcgtgggg acactagacc caaagtccat aggcatacac acaagaaaa    180 ccctaagcca cttcaggttc tactggcacg aagtcttcag cggagaaaac cccacaacgg    240
ttagaatcat tccctcactc cccaaataca acacaaccac aaccttcggt tccgttggaa    300
tctttgacaa cactttaacc gtgggacctg aggtgtactc caaggttgcc ggaaaagccg    360
agggcttgtt tgcctccacg tcacaaacgc agtttaacct gttactgatt tacagcttcg    420
cgttgaccca agggaagtac aacggcagca ccatcacgtt cacggggagg agccccctct    480
cggagaaggt gagggagctg cccattgttg gtggcagtgg ggtcttcaaa tttgccactg    540
ggtatgttga gtctaggacg ctaagttttg atccccaaac gaggaataac acggttcagt    600
tcgacgtgta tatttactat tgatgattat tgaatgtgtt tttacatgt tgatgtgtta    660 gagctttggt gtgtgtcact tagttttcta                                     689

<210> SEQ ID NO 5
<211> LENGTH: 703
<212> TYPE: DNA
<213> ORGANISM: Glycine pescadrensis

<400> SEQUENCE: 5
ataaattctt gcattaattc atcactttca tcacccaatc catttcctct aattaacacc     60
caccaaaacc atggcttccc acttcctcaa atccctcctt ctcctctcca cctatgccct    120
caccatctca gcagaataca caggcttcgt gggcacacta gacccaaagt ccataggcat    180
acaccacaag aaaaccctaa accacttcag gttctactgg cacgaagtct tcagcggaga    240
aaaccccaca tcggttagaa tcattccctc actccccaaa tacaacacaa ccacaacctt    300
cggttccgtt ggaatctctg acaacgcttt aaccgtggga cctgaggtgt actccaaggt    360
tgtcggaaaa gccgagggct tgtttgtctc cacgtcacaa acgcagtttg acctgttact    420
gatttacaac ttcgcgttga cccaagggaa gtacaacggc agcaccatca cgttcacggg    480
gaggagcccc ctctcggaga aggtgaggga gctgcccatt gtaggtggca gtggggtctt    540
caaatttccc actgggtatg ttgagtctag gacgctaagt tttgatcccc aaacgaggaa    600
```

```
taacacggtt cagttcgacg tgtatattta ctattgatga ttattgaatg tgttttttcc      660
atgttgatgt gttatagctt tggtatgtgt cacttagttt cta                        703

<210> SEQ ID NO 6
<211> LENGTH: 674
<212> TYPE: DNA
<213> ORGANISM: Glycine tabacina

<400> SEQUENCE: 6
catcacccaa tccactcctc taattaacac ccaccaacac catggcttcc cacttcctca       60
aatccctcct tctcctctcc acctatgccc tcaccatctc agcagaatac acaggcttcg      120
tggggacact agacccaaag tccataggca tacaccacaa gaaaacccta agccacttca      180
ggttctactg gcacgaagtc ttcagcggag aaaaccccac aacggttaga atcattccct      240
cactccccaa atacaacaca accacaacct tcggttccgt tggaatcttt gacaacactt      300
taaccgtggg acctgaggtg tactctaagg ttgccggaaa agccgagggc ttgtttgcct      360
ccacgtcaca aacgcagttt aacctgttac tgatttacag cttcgcgttg acccaaggga      420
agtacaacgg cagcaccatc acgttcacgg ggaggagccc cctctcggag aaggtgaggg      480
agctgcccat tgttggtggc agtggggtct tcaaatttgc cactgggtat gttgagtcta      540
ggacgctaag ttttgatccc caaacgagga ataacacggt tcagttcgac gtgtatattt      600
actattgatg attattgaat gtgttttta catgttgatg tgttagagct ttggtgtgtg      660
tcacttagtt tcta                                                        674

<210> SEQ ID NO 7
<211> LENGTH: 728
<212> TYPE: DNA
<213> ORGANISM: Glycine tabacina

<400> SEQUENCE: 7
cctacttcga tgcttccccc accttataaa ttcttgcatt aattcatcac tttcatcacc       60
caatccattt cctctaatta acacccacca aaaccatggc ttcccacttc ctcaaatccc      120
tccttctcct ctccacctat gccctcacca tctcagcaga atacacaggc ttcgtgggca      180
cactagaccc aaagtccata ggcatacacc acaagaaaac cctaaaccac ttcaggttct      240
actggcacga agtcttcagc ggagaaaaac ccacatcggt tagaatcatt ccctcactcc      300
ccaaatacaa cacaaccaca accttcggtt ccgttggaat ctctgacaac gctttaaccg      360
tgggacctga ggtgtactcc aaggttgtcg gaaaagccga gggcttgttt gtctccacgt      420
cacaaacgca gtttgacctg ttactgattt acaacttcgc gttgacccaa gggaagtaca      480
acggcagcac catcacgttc acggggagga gccccctctc ggagaaggtg agggagctgc      540
ccattgtagg tggcagtggg gtcttcaaat tttccactgg gtatgttgag tctaggacgc      600
taagttttga tccccaaacg aggaataaca cggttcagtt cgacgtgtat atttactatt      660
gatgattatt gaatgtgttt tttccatgtt gatgtgttat agctttggta tgtgtcactt      720
agtttcta                                                               728

<210> SEQ ID NO 8
<211> LENGTH: 745
<212> TYPE: DNA
<213> ORGANISM: Glycine tomentella

<400> SEQUENCE: 8
cacctacttc gatgcttccc cccaccttat aaattcttgc attaattcat cactttcatc       60
```

```
acccaatcca tttcctctaa ttaacaccca ccaaaaccat ggcttccac ttcctcaaat    120 ccctccttct cctctccacc tatgccctca ccatctcagc agaatacaca ggcttcgtgg    180
gcacactaga cccaaagtcc ataggcatac accacaagaa aaccctaaac cacttcaggt    240
tctactggca cgaagtcttc agcggagaaa accccacatc ggttagaatc attccctcac    300
tccccaaata caacacaacc acaaccttcg gttccgttgg aatctctgac aacgctttaa    360
ccgtgggacc tgaggtgtac tccaaggttg tcggaaaagc cgagggcttg tttgtctcca    420
cgtcacaaac gcagtttgac ctgttactga tttacaactt cgcgttgacc caagggaagt    480
acaacggcag caccatcacg ttcacgggga ggagccccct ctcggagaag gtgagggagc    540
tgcccattgt aggtggcagt ggggtcttca aattttccac tgggtatgtt gagtctagga    600
tgctaagttt tgatcccaa acgaggaata acacggttca gttcgacgtg tatatttact    660
attgatgatt attgaatgtg tttttttccat gttgatgtgt tatagctttg gtatgtgtca    720
cttagtttct atataagttt ccama                                          745
```

<210> SEQ ID NO 9
<211> LENGTH: 188
<212> TYPE: PRT
<213> ORGANISM: Glycine max

<400> SEQUENCE: 9

```
Met Ala Ser His Phe Leu Lys Ser Leu Leu Leu Ser Thr Tyr Ala
1               5                   10                  15

Leu Thr Ile Ser Ala Glu Tyr Thr Gly Phe Val Gly Thr Leu Asp Pro
            20                  25                  30

Lys Ser Ile Gly Ile His His Lys Lys Thr Leu Ser His Phe Arg Phe
        35                  40                  45

Tyr Trp His Glu Val Phe Ser Gly Glu Asn Pro Thr Ser Val Arg Ile
    50                  55                  60

Ile Pro Ser Leu Pro Lys Tyr Asn Ala Thr Thr Thr Phe Gly Ser Val
65                  70                  75                  80

Gly Ile Phe Asp Thr Pro Leu Thr Val Gly Pro Glu Val Tyr Ser Lys
                85                  90                  95

Val Val Gly Lys Ala Glu Gly Leu Phe Ala Ser Thr Ser Gln Thr Gln
            100                 105                 110

Phe Asp Leu Leu Leu Ile Tyr Asn Phe Ala Leu Thr Gln Gly Lys Tyr
        115                 120                 125

Asn Gly Ser Thr Ile Thr Phe Thr Gly Arg Ser Pro Leu Ser Glu Lys
    130                 135                 140

Val Arg Glu Leu Pro Ile Val Gly Gly Ser Gly Val Phe Lys Phe Ala
145                 150                 155                 160

Thr Gly Tyr Val Glu Ser Arg Thr Leu Ser Phe Asp Pro Gln Thr Arg
                165                 170                 175

Asn Asn Thr Val Gln Phe Asp Val Tyr Ile Tyr Tyr
            180                 185
```

<210> SEQ ID NO 10
<211> LENGTH: 188
<212> TYPE: PRT
<213> ORGANISM: Glycine max

<400> SEQUENCE: 10

```
Met Ala Ser His Phe Leu Lys Ser Leu Leu Leu Ser Thr Tyr Ala
1               5                   10                  15
```

```
Leu Thr Ile Ser Ala Glu Tyr Thr Gly Phe Val Gly Thr Leu Asp Pro
            20                  25                  30

Lys Ser Ile Gly Ile His His Lys Thr Leu Ser His Phe Arg Phe
        35                  40                  45

Tyr Trp His Glu Val Phe Ser Gly Glu Asn Pro Thr Ser Val Arg Ile
 50                  55                  60

Ile Pro Ser Leu Pro Lys Tyr Asn Ala Thr Thr Phe Gly Ser Val
 65              70                  75                  80

Gly Ile Phe Asp Thr Pro Leu Thr Val Gly Pro Glu Val Tyr Ser Lys
                85                  90                  95

Val Val Gly Lys Ala Glu Gly Leu Phe Ala Ser Thr Ser Gln Thr Gln
            100                 105                 110

Phe Asp Leu Leu Leu Ile Tyr Asn Phe Ala Leu Thr Gln Gly Lys Tyr
            115                 120                 125

Asn Gly Ser Thr Ile Thr Phe Thr Gly Arg Ser Pro Leu Ser Glu Lys
            130                 135                 140

Val Arg Glu Leu Pro Ile Val Gly Gly Ser Gly Val Phe Lys Phe Ala
145                 150                 155                 160

Thr Gly Tyr Val Glu Ser Arg Thr Leu Ser Phe Asp Pro Gln Thr Arg
                165                 170                 175

Asn Asn Thr Val Gln Phe Asp Val Tyr Ile Tyr Tyr
            180                 185

<210> SEQ ID NO 11
<211> LENGTH: 188
<212> TYPE: PRT
<213> ORGANISM: Glycine microphylla

<400> SEQUENCE: 11

Met Ala Ser His Phe Leu Lys Ser Leu Leu Leu Ser Thr Tyr Ala
1               5                   10                  15

Leu Thr Ile Ser Ala Glu Tyr Thr Gly Phe Val Gly Thr Leu Asp Pro
            20                  25                  30

Lys Ser Ile Gly Ile His His Lys Lys Thr Leu Ser His Phe Arg Phe
            35                  40                  45

Tyr Trp His Glu Val Phe Ser Gly Glu Asn Pro Thr Thr Val Arg Ile
 50                  55                  60

Ile Pro Ser Leu Pro Lys Tyr Asn Thr Thr Thr Phe Gly Ser Val
 65              70                  75                  80

Gly Ile Phe Asp Asn Thr Leu Thr Val Gly Pro Glu Val Tyr Ser Lys
                85                  90                  95

Val Ala Gly Lys Ala Glu Gly Leu Phe Ala Ser Thr Ser Gln Thr Gln
            100                 105                 110

Phe Asn Leu Leu Leu Ile Tyr Ser Phe Ala Leu Thr Gln Gly Lys Tyr
            115                 120                 125

Asn Gly Ser Thr Ile Thr Phe Thr Gly Arg Ser Pro Leu Ser Glu Lys
            130                 135                 140

Val Arg Glu Leu Pro Ile Val Gly Gly Ser Gly Val Phe Lys Phe Ala
145                 150                 155                 160

Thr Gly Tyr Val Glu Ser Arg Thr Leu Ser Phe Asp Pro Gln Thr Arg
                165                 170                 175

Asn Asn Thr Val Gln Phe Asp Val Tyr Ile Tyr Tyr
            180                 185
```

<210> SEQ ID NO 12
<211> LENGTH: 188
<212> TYPE: PRT
<213> ORGANISM: Glycine pescadrensis

<400> SEQUENCE: 12

Met Ala Ser His Phe Leu Lys Ser Leu Leu Leu Ser Thr Tyr Ala
1               5                   10                  15

Leu Thr Ile Ser Ala Glu Tyr Thr Gly Phe Val Gly Thr Leu Asp Pro
            20                  25                  30

Lys Ser Ile Gly Ile His His Lys Lys Thr Leu Asn His Phe Arg Phe
                35                  40                  45

Tyr Trp His Glu Val Phe Ser Gly Glu Asn Pro Thr Ser Val Arg Ile
    50                  55                  60

Ile Pro Ser Leu Pro Lys Tyr Asn Thr Thr Thr Phe Gly Ser Val
65                  70                  75                  80

Gly Ile Ser Asp Asn Ala Leu Thr Val Gly Pro Glu Val Tyr Ser Lys
                85                  90                  95

Val Val Gly Lys Ala Glu Gly Leu Phe Val Ser Thr Ser Gln Thr Gln
            100                 105                 110

Phe Asp Leu Leu Leu Ile Tyr Asn Phe Ala Leu Thr Gln Gly Lys Tyr
        115                 120                 125

Asn Gly Ser Thr Ile Thr Phe Thr Gly Arg Ser Pro Leu Ser Glu Lys
    130                 135                 140

Val Arg Glu Leu Pro Ile Val Gly Gly Ser Gly Val Phe Lys Phe Ser
145                 150                 155                 160

Thr Gly Tyr Val Glu Ser Arg Thr Leu Ser Phe Asp Pro Gln Thr Arg
                165                 170                 175

Asn Asn Thr Val Gln Phe Asp Val Tyr Ile Tyr Tyr
            180                 185

<210> SEQ ID NO 13
<211> LENGTH: 188
<212> TYPE: PRT
<213> ORGANISM: Glycine tabacina

<400> SEQUENCE: 13

Met Ala Ser His Phe Leu Lys Ser Leu Leu Leu Ser Thr Tyr Ala
1               5                   10                  15

Leu Thr Ile Ser Ala Glu Tyr Thr Gly Phe Val Gly Thr Leu Asp Pro
            20                  25                  30

Lys Ser Ile Gly Ile His His Lys Lys Thr Leu Ser His Phe Arg Phe
                35                  40                  45

Tyr Trp His Glu Val Phe Ser Gly Glu Asn Pro Thr Thr Val Arg Ile
    50                  55                  60

Ile Pro Ser Leu Pro Lys Tyr Asn Thr Thr Thr Phe Gly Ser Val
65                  70                  75                  80

Gly Ile Phe Asp Asn Thr Leu Thr Val Gly Pro Glu Val Tyr Ser Lys
                85                  90                  95

Val Ala Gly Lys Ala Glu Gly Leu Phe Ala Ser Thr Ser Gln Thr Gln
            100                 105                 110

Phe Asn Leu Leu Leu Ile Tyr Ser Phe Ala Leu Thr Gln Gly Lys Tyr
        115                 120                 125

Asn Gly Ser Thr Ile Thr Phe Thr Gly Arg Ser Pro Leu Ser Glu Lys
    130                 135                 140

Val Arg Glu Leu Pro Ile Val Gly Gly Ser Gly Val Phe Lys Phe Ala

```
                    145                 150                 155                 160
Thr Gly Tyr Val Glu Ser Arg Thr Leu Ser Phe Asp Pro Gln Thr Arg
                    165                 170                 175

Asn Asn Thr Val Gln Phe Asp Val Tyr Ile Tyr Tyr
                    180                 185

<210> SEQ ID NO 14
<211> LENGTH: 188
<212> TYPE: PRT
<213> ORGANISM: Glycine tabacina

<400> SEQUENCE: 14

Met Ala Ser His Phe Leu Lys Ser Leu Leu Leu Ser Thr Tyr Ala
1               5                   10                  15

Leu Thr Ile Ser Ala Glu Tyr Thr Gly Phe Val Gly Thr Leu Asp Pro
                    20                  25                  30

Lys Ser Ile Gly Ile His His Lys Lys Thr Leu Asn His Phe Arg Phe
                    35                  40                  45

Tyr Trp His Glu Val Phe Ser Gly Glu Asn Pro Thr Ser Val Arg Ile
                    50                  55                  60

Ile Pro Ser Leu Pro Lys Tyr Asn Thr Thr Thr Phe Gly Ser Val
65                  70                  75                  80

Gly Ile Ser Asp Asn Ala Leu Thr Val Gly Pro Glu Val Tyr Ser Lys
                    85                  90                  95

Val Val Gly Lys Ala Glu Gly Leu Phe Val Ser Thr Ser Gln Thr Gln
                    100                 105                 110

Phe Asp Leu Leu Leu Ile Tyr Asn Phe Ala Leu Thr Gln Gly Lys Tyr
                    115                 120                 125

Asn Gly Ser Thr Ile Thr Phe Thr Gly Arg Ser Pro Leu Ser Glu Lys
                    130                 135                 140

Val Arg Glu Leu Pro Ile Val Gly Gly Ser Gly Val Phe Lys Phe Ser
145                 150                 155                 160

Thr Gly Tyr Val Glu Ser Arg Thr Leu Ser Phe Asp Pro Gln Thr Arg
                    165                 170                 175

Asn Asn Thr Val Gln Phe Asp Val Tyr Ile Tyr Tyr
                    180                 185

<210> SEQ ID NO 15
<211> LENGTH: 188
<212> TYPE: PRT
<213> ORGANISM: Glycine tomentella

<400> SEQUENCE: 15

Met Ala Ser His Phe Leu Lys Ser Leu Leu Leu Ser Thr Tyr Ala
1               5                   10                  15

Leu Thr Ile Ser Ala Glu Tyr Thr Gly Phe Val Gly Thr Leu Asp Pro
                    20                  25                  30

Lys Ser Ile Gly Ile His His Lys Lys Thr Leu Asn His Phe Arg Phe
                    35                  40                  45

Tyr Trp His Glu Val Phe Ser Gly Glu Asn Pro Thr Ser Val Arg Ile
                    50                  55                  60

Ile Pro Ser Leu Pro Lys Tyr Asn Thr Thr Thr Phe Gly Ser Val
65                  70                  75                  80

Gly Ile Ser Asp Asn Ala Leu Thr Val Gly Pro Glu Val Tyr Ser Lys
                    85                  90                  95

Val Val Gly Lys Ala Glu Gly Leu Phe Val Ser Thr Ser Gln Thr Gln
```

```
                100              105              110
Phe Asp Leu Leu Leu Ile Tyr Asn Phe Ala Leu Thr Gln Gly Lys Tyr
            115                      120                  125

Asn Gly Ser Thr Ile Thr Phe Thr Gly Arg Ser Pro Leu Ser Glu Lys
        130                      135              140

Val Arg Glu Leu Pro Ile Val Gly Gly Ser Gly Val Phe Lys Phe Ser
145                     150                  155                 160

Thr Gly Tyr Val Glu Ser Arg Met Leu Ser Phe Asp Pro Gln Thr Arg
                    165                 170                 175

Asn Asn Thr Val Gln Phe Asp Val Tyr Ile Tyr Tyr
                180                 185

<210> SEQ ID NO 16
<211> LENGTH: 623
<212> TYPE: DNA
<213> ORGANISM: Solanum sp.

<400> SEQUENCE: 16
cattccatgg ccaaactaat actccaaatc ttcaccattt ccctcttcct ttctctggtg    60
gcctttcgcg ccaccggaga agaagataat tatattttg gaaatccat aaacaaaaaa    120 cccacaaggt taagaaagga aaaatcagt cattttcgat ttttttggca tgatatttta    180
agtggttcaa accaacatc aatgatgatt attccaccac ctaaaaacac aacaacaggt    240
tttggacaaa tgaatatgat agataatgcc ttaaccttag gaccaaaact aagttccaag    300
attgttggta gggcacaagg gttttatggt gctgcttcac ttaatgatgt tggattaatg    360
atggttatga attttgcttt tattgaaggg aaatataatg gaagtacttt tactatactt    420
ggtcggaatc cggtgttcga aaggtgaga gagatggcgg tgatcggagg gagtgggctt    480
ttccgatttg ctagaggata tgttcaagct agtactcatt catgggattt caaaactgga    540
gatgctactg ttcagtatga tgcttatgtc tttgcattat tgaggtttac taatttttata   600 tattttcatc gtgtcaattt atg                                            623

<210> SEQ ID NO 17
<211> LENGTH: 648
<212> TYPE: DNA
<213> ORGANISM: Solanum peruvianum

<400> SEQUENCE: 17
tcaaagaatt tacttccatt ccatggccaa actaatactc caaatcttca ccatttccct    60
cttcctttct ctggtggcct ttcgcgccac cggagaagaa gataattatg ttttggaaa    120 atccataaac aaaaaaccca caaggttaag aaaggaaaaa ttcagtcatt ttcgatttta    180
ttggcatgat attttaagtg gttcaaaacc aacatcaatg atgattattc caccactaa    240 aaacacaaca acaggttttg gacaaatgaa tatgatagat aatgccttaa ccttaggacc    300
aaaactaagt tccaagattg ttggtagggc acaagggttt tatggtgctg cttcacttaa    360
tgatgttgga ttaatgatgg ttatgaattt tgcttttatt gaagggaaat ataatggaag    420 tactttttact atacttggtc ggaatccggt gttcgagaag gtgagagaga tggcggtgat    480
cggagggact gggcttttcc gatttgctag aggatatgtt gaagctagta ctcattcatg    540
ggatttcaaa actggagatg ctactgttca gtatgatgct tatgtcttgc attattgagg    600
tttactaatt ttatatattt tcatcgtgtc aatttatgcg acctagtt                 648

<210> SEQ ID NO 18
```

```
<211> LENGTH: 552
<212> TYPE: DNA
<213> ORGANISM: Solanum chmielewskii

<400> SEQUENCE: 18
attccatggc caaactaata ctccaaatct tcaccatttc cctcttcctt tctctggtgg      60
cctttcgcgc cacyggagaa gaagataatt atattttgg aaaatccata acaaaaaac      120 ccacaaggtt aagaaggaa aaaatcagtc attttcgatt ttattggcat gatattttaa      180
gtggttcaaa accaacatca atgatgatta ttccaccacc taaaaacaca acaacaggtt      240
ttggacaaat gaatatgata gataatgcct taaccttagg accaaaacta agttccaaga      300
ttgttggtag ggcacaaggg ttttatggtg ctgcttcact taatgatgtt ggattaatga      360
tggttatgaa ttttgctttt attgaaggga aatataatgg aagtactttt actatacttg      420
gtcggaatcc ggtgtttgag aaggtgagag agatggcggt gataggaggg agtgggcttt      480
tccgatttgc tagaggatat gttcaagcta gtactcattc atgggatttc aaaactggag      540
atgctactgt tc                                                         552

<210> SEQ ID NO 19
<211> LENGTH: 608
<212> TYPE: DNA
<213> ORGANISM: Solanum habrochaites

<400> SEQUENCE: 19
tacttccatt ccatggccaa actaatactc caaatcttca ccatttccct cttcctttct      60
ctggtggcct ttcgsccac cggagaagaa gataatyata tttttgaaaa atccataaac      120
aaaaaaccca aaggttaag aaagsaaaaa ttcagtcatt ttcgatttta ttggcatgat      180
attctaagtg gttcaaaacc aacatcaatg atgattattc caccacctaa aaacacaaca      240
acaggttttg gacaaatgaa tatgatagat aatgccttaa ccttaggacc aaaactaagt      300
tccaagattg ttggtagggc acagggttt tatggtgctg cttcacttaa tgatgttgga      360
ttaatgatgg ttatgaattt tgcttttatt gaagggaaat ayaatggaag tacttttact      420
atacttggtc ggaatccggt gwtcgagaag gtgagagaga tggcggtgat cggagggag      480 gggctttcc gatttgctag aggatatgtt caagctagta ctcattcatg ggatttcaaa      540
actggagatg ctactgttca gtatgatgct tatgtcttgc attattgagg tttactaatt      600
ttatatat                                                              608

<210> SEQ ID NO 20
<211> LENGTH: 639
<212> TYPE: DNA
<213> ORGANISM: Solanum corneliomulleri

<400> SEQUENCE: 20
cttcaccaac tgactcaaag aatttacttc cattccatgg ccaaactaat actcctaatc      60 ttcaccatt ccgtcttcct ttctctggtg gcctttcgtg ccaccggaga agaagataat      120 tatattttg aaaatccat aaacaaaaaa cccacaaggt taagaaagga aaaattcagt      180 catttcgat tttattggca tgatatttta agtggttcaa aaccaacatc aatgatgatt      240
attccaccac ctaaaaacac aacaacaggt tttggacaaa tgaatatgat agataatgcc      300
ttaaccttag gaccaaaact aagttccaag attgttggaa gggcacaagg gtttatggt      360 gctgcttcac ttaatgatgt tggattaatg atggttatga ttttgctttt attgaaggg      420 aaatataatg gaagtacttt tactatactt ggtcggaatc cggtgttcga aaggtgaga      480
```

```
gagatggcgg tgatcggagg gagtgggctt ttccgatttg ctagaggata tgttcaagct    540
agtactcatt catgggattt caaaactgga gatgctactg ttcagtatga tgcttatgtc    600
ttgcattatt gaggtttact aattttatat attttcatc                           639
```

<210> SEQ ID NO 21
<211> LENGTH: 623
<212> TYPE: DNA
<213> ORGANISM: Capsicum annuum

<400> SEQUENCE: 21

```
gcacgaggct caaagaatct acttccatgg ccaaactaat actccaaatc ttctccattt     60
ccgttctcta ttcactggta gcctttccag ccacgggaga agaagatcat attttttggaa   120 aatccataaa tgaaaagtcc atgaggctaa aagggaaaaa actcagccat ttcagatttt    180
attggcacga cgtcctcagt ggctccaaac caacatctat gataattatc ccacctccca    240
aaaatactac cacaggcttt ggccaaatga atatgataga taatgcccta accttaggac    300
cagagctgag ttccaggata gttggaaggg cacaagggtt ttacgctgct gcttcactaa    360
atgatgttgg cttaatgatg gtcatgaact ttgcttttat tgaaggaaaa tataatggga    420
gcaccttcac tatacttgga cgaaatccgg tatttgagaa ggtgagagag atggccgtga    480
tcggcggcag tgggcttttc cgatttgcta aggatatgt tcaggctagt actcattcat    540
tggatttcaa aactggcgat gctactgttc agtatgatgc tatgttttg cattattgaa     600 gtttactaat attatatatc act                                            623
```

<210> SEQ ID NO 22
<211> LENGTH: 650
<212> TYPE: DNA
<213> ORGANISM: Capsicum annuum

<400> SEQUENCE: 22

```
gcacgaggta cttccatggc caaactaata ctccaaatct tctccatttc cgttctctat     60
tcactggtag cctttccagc cacgggagaa gaagatcata ttttggaaa atccataaat    120 gaaaagtcca tgaggctaaa agggaaaaa ctcagccatt tcagatttta ttggcacgac    180
gtcctcagtg ctccaaacc aacatctatg ataattatcc cacctcccaa aaatactacc    240
acaggctttg gccaaatgaa tatgatagat aatgccctaa ccttaggacc agagctgagt    300
tccaggatag ttggaagggc acaagggttt tacgctgctg cttcactaaa tgatgttggc    360
ttaatgatgg tcatgaactt tgcttttatt gaaggaaaat ataatgggag caccttcact    420
atacttggac gaaatccggt atttgagaag gtgagagaga tggccgtgat cggcggcagt    480
gggcttttcc gatttgctag aggatatgtt caggctagta ctcattcatt ggatttcaaa    540
actggcgatg ctactgttca gtatgatgcc tatgttttgc attattgaag tttactaata    600
ttatatatca ctctaatcgg ctagctggct tttaattaat aattatgtcg               650
```

<210> SEQ ID NO 23
<211> LENGTH: 560
<212> TYPE: DNA
<213> ORGANISM: Solanum melongena

<400> SEQUENCE: 23

```
atggccaaac tatcactcca atcttcacc atctccattc tcctttttct ggttgccttt      60
ccggcaaccg gagaagaaga taattatact tttggaaaat ccataaataa aaagtctatg    120
```

-continued

```
aggttaagaa aggagaaact cagccatttc agattttatt ggcatgatgt cctaagtggc    180
tcaaaaccaa catcaatgat gattattcca ccacctaaaa acaccacaac aggttttgga    240
caaatgaata tgatagataa tgccttaacc ttaggagcag agttgagttc caagattgtt    300
ggaagggcac aagggtttta cgctgctgct tcacttaatg atgttggatt aatgatggta    360
atgaattttg cttttattga agggaaatat aatggaagca ctttcactat acttggacgg    420
aatccggtgt ttgagaaggt gagggagatg gcggtgatcg gaggaagtgg acttttccga    480
tttgctagag gatatgttca ggccagtact cattcatggg attacaaaac tggagatgct    540
actgtgaagt atgatgctta                                                560
```

<210> SEQ ID NO 24
<211> LENGTH: 729
<212> TYPE: DNA
<213> ORGANISM: Solanum tuberosum

<400> SEQUENCE: 24

```
gaaaattctc caccaagtga ctcaaagaat ttacttccat tccatggcca aaataatact     60
ccaaatcttc accatttcca tcttcctttc tctggtggcc tttccggcca ccggagaaga    120
agatacttat atttttggaa aatctataaa caaaaaaccc acaaggttaa aaaaggaaaa    180
attcagtcat tttcgatttt attggcatga tattctaagt ggttcaaaac caacatcaat    240
gatgattatt ccaccatcta aaacacaac aacaggtttt gggcaaatga atatgataga    300
taatgcctta accttaggac cagaattaag ttccaagatt gttggaaggg cgcaagggtt    360
ttatggtgct gcttcactta atgatgttgg tttaatgatg ttatgaatt ttgctttat    420 tgaagggaaa tataatggaa gtactttac tatacttggt cggaatccgg tgttcgagaa    480
ggtgagagag atggcggtga tcggagggag tgggcttttc cgatttgcta gaggatatgt    540
tgaagctagt actcattcat gggattttaa aactggagat gctacggttc agtatgatgc    600
ttatgtcttg cattattaag gttttactaa ttttgtatgt tttcgttgtg tcaatttat    660 aagatttagt ttaactggat actaaattta tgaaatatcc cattttgttc aaaaaaaaaa    720
aaaaaaaaa                                                            729
```

<210> SEQ ID NO 25
<211> LENGTH: 206
<212> TYPE: PRT
<213> ORGANISM: Solanum sp.
<220> FEATURE:
<221> NAME/KEY: misc_feature
<222> LOCATION: (206)..(206)
<223> OTHER INFORMATION: Xaa can be any naturally occurring amino acid

<400> SEQUENCE: 25

```
Met Ala Lys Leu Ile Leu Gln Ile Phe Thr Ile Ser Leu Phe Leu Ser
1               5                   10                  15

Leu Val Ala Phe Arg Ala Thr Gly Glu Glu Asp Asn Tyr Ile Phe Gly
            20                  25                  30

Lys Ser Ile Asn Lys Lys Pro Thr Arg Leu Arg Lys Glu Lys Ile Ser
        35                  40                  45

His Phe Arg Phe Trp His Asp Ile Leu Ser Gly Ser Lys Pro Thr
    50                  55                  60

Ser Met Met Ile Ile Pro Pro Lys Asn Thr Thr Thr Gly Phe Gly
65                  70                  75                  80

Gln Met Asn Met Ile Asp Asn Ala Leu Thr Leu Gly Pro Lys Leu Ser
            85                  90                  95
```

```
Ser Lys Ile Val Gly Arg Ala Gln Gly Phe Tyr Gly Ala Ala Ser Leu
        100                 105                 110

Asn Asp Val Gly Leu Met Met Val Met Asn Phe Ala Phe Ile Glu Gly
        115                 120                 125

Lys Tyr Asn Gly Ser Thr Phe Thr Ile Leu Gly Arg Asn Pro Val Phe
        130                 135                 140

Glu Lys Val Arg Glu Met Ala Val Ile Gly Gly Ser Gly Leu Phe Arg
145                 150                 155                 160

Phe Ala Arg Gly Tyr Val Gln Ala Ser Thr His Ser Trp Asp Phe Lys
                165                 170                 175

Thr Gly Asp Ala Thr Val Gln Tyr Asp Ala Tyr Val Phe Ala Leu Leu
        180                 185                 190

Arg Phe Thr Asn Phe Ile Tyr Phe His Arg Val Asn Leu Xaa
        195                 200                 205

<210> SEQ ID NO 26
<211> LENGTH: 191
<212> TYPE: PRT
<213> ORGANISM: Solanum peruvianum

<400> SEQUENCE: 26

Met Ala Lys Leu Ile Leu Gln Ile Phe Thr Ile Ser Leu Phe Leu Ser
1               5                   10                  15

Leu Val Ala Phe Arg Ala Thr Gly Glu Glu Asp Asn Tyr Val Phe Gly
            20                  25                  30

Lys Ser Ile Asn Lys Lys Pro Thr Arg Leu Arg Lys Glu Lys Phe Ser
        35                  40                  45

His Phe Arg Phe Tyr Trp His Asp Ile Leu Ser Gly Ser Lys Pro Thr
    50                  55                  60

Ser Met Met Ile Ile Pro Pro Lys Asn Thr Thr Gly Phe Gly
65                  70                  75                  80

Gln Met Asn Met Ile Asp Asn Ala Leu Thr Leu Gly Pro Lys Leu Ser
                85                  90                  95

Ser Lys Ile Val Gly Arg Ala Gln Gly Phe Tyr Gly Ala Ala Ser Leu
        100                 105                 110

Asn Asp Val Gly Leu Met Met Val Met Asn Phe Ala Phe Ile Glu Gly
        115                 120                 125

Lys Tyr Asn Gly Ser Thr Phe Thr Ile Leu Gly Arg Asn Pro Val Phe
        130                 135                 140

Glu Lys Val Arg Glu Met Ala Val Ile Gly Gly Thr Gly Leu Phe Arg
145                 150                 155                 160

Phe Ala Arg Gly Tyr Val Glu Ala Ser Thr His Ser Trp Asp Phe Lys
                165                 170                 175

Thr Gly Asp Ala Thr Val Gln Tyr Asp Ala Tyr Val Leu His Tyr
        180                 185                 190

<210> SEQ ID NO 27
<211> LENGTH: 183
<212> TYPE: PRT
<213> ORGANISM: Solanum chmielewskii
<220> FEATURE:
<221> NAME/KEY: misc_feature
<222> LOCATION: (183)..(183)
<223> OTHER INFORMATION: Xaa can be any naturally occurring amino acid

<400> SEQUENCE: 27

Met Ala Lys Leu Ile Leu Gln Ile Phe Thr Ile Ser Leu Phe Leu Ser
```

```
                1               5                   10                  15
Leu Val Ala Phe Arg Ala Thr Gly Glu Glu Asp Asn Tyr Ile Phe Gly
                20                  25                  30

Lys Ser Ile Asn Lys Lys Pro Thr Arg Leu Arg Lys Glu Lys Ile Ser
                35                  40                  45

His Phe Arg Phe Tyr Trp His Asp Ile Leu Ser Gly Ser Lys Pro Thr
                50                  55                  60

Ser Met Met Ile Ile Pro Pro Lys Asn Thr Thr Thr Gly Phe Gly
 65                 70                  75                  80

Gln Met Asn Met Ile Asp Asn Ala Leu Thr Leu Gly Pro Lys Leu Ser
                85                  90                  95

Ser Lys Ile Val Gly Arg Ala Gln Gly Phe Tyr Gly Ala Ala Ser Leu
                100                 105                 110

Asn Asp Val Gly Leu Met Met Val Met Asn Phe Ala Phe Ile Glu Gly
                115                 120                 125

Lys Tyr Asn Gly Ser Thr Phe Thr Ile Leu Gly Arg Asn Pro Val Phe
                130                 135                 140

Glu Lys Val Arg Glu Met Ala Val Ile Gly Gly Ser Gly Leu Phe Arg
145                 150                 155                 160

Phe Ala Arg Gly Tyr Val Gln Ala Ser Thr His Ser Trp Asp Phe Lys
                165                 170                 175

Thr Gly Asp Ala Thr Val Xaa
                180
```

<210> SEQ ID NO 28
<211> LENGTH: 191
<212> TYPE: PRT
<213> ORGANISM: Solanum habrochaites
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid

<400> SEQUENCE: 28

```
Met Ala Lys Leu Ile Leu Gln Ile Phe Thr Ile Ser Leu Phe Leu Ser
  1               5                   10                  15

Leu Val Ala Phe Arg Ala Thr Gly Glu Glu Asp Asn Xaa Ile Phe Glu
                20                  25                  30

Lys Ser Ile Asn Lys Lys Pro Thr Arg Leu Arg Lys Xaa Lys Phe Ser
                35                  40                  45

His Phe Arg Phe Tyr Trp His Asp Ile Leu Ser Gly Ser Lys Pro Thr
                50                  55                  60

Ser Met Met Ile Ile Pro Pro Lys Asn Thr Thr Thr Gly Phe Gly
 65                 70                  75                  80

Gln Met Asn Met Ile Asp Asn Ala Leu Thr Leu Gly Pro Lys Leu Ser
                85                  90                  95

Ser Lys Ile Val Gly Arg Ala Gln Gly Phe Tyr Gly Ala Ala Ser Leu
                100                 105                 110

Asn Asp Val Gly Leu Met Met Val Met Asn Phe Ala Phe Ile Glu Gly
                115                 120                 125
```

Lys Tyr Asn Gly Ser Thr Phe Thr Ile Leu Gly Arg Asn Pro Val Xaa
            130                 135                 140

Glu Lys Val Arg Glu Met Ala Val Ile Gly Gly Ser Gly Leu Phe Arg
145                 150                 155                 160

Phe Ala Arg Gly Tyr Val Gln Ala Ser Thr His Ser Trp Asp Phe Lys
                165                 170                 175

Thr Gly Asp Ala Thr Val Gln Tyr Asp Ala Tyr Val Leu His Tyr
            180                 185                 190

<210> SEQ ID NO 29
<211> LENGTH: 191
<212> TYPE: PRT
<213> ORGANISM: Solanum corneliomulleri

<400> SEQUENCE: 29

Met Ala Lys Leu Ile Leu Leu Ile Phe Thr Ile Ser Val Phe Leu Ser
1               5                   10                  15

Leu Val Ala Phe Arg Ala Thr Gly Glu Glu Asp Asn Tyr Ile Phe Gly
            20                  25                  30

Lys Ser Ile Asn Lys Lys Pro Thr Arg Leu Arg Lys Glu Lys Phe Ser
        35                  40                  45

His Phe Arg Phe Tyr Trp His Asp Ile Leu Ser Gly Ser Lys Pro Thr
50                  55                  60

Ser Met Met Ile Ile Pro Pro Lys Asn Thr Thr Thr Gly Phe Gly
65                  70                  75                  80

Gln Met Asn Met Ile Asp Asn Ala Leu Thr Leu Gly Pro Lys Leu Ser
                85                  90                  95

Ser Lys Ile Val Gly Arg Ala Gln Gly Phe Tyr Gly Ala Ala Ser Leu
            100                 105                 110

Asn Asp Val Gly Leu Met Met Val Met Asn Phe Ala Phe Ile Glu Gly
        115                 120                 125

Lys Tyr Asn Gly Ser Thr Phe Thr Ile Leu Gly Arg Asn Pro Val Phe
130                 135                 140

Glu Lys Val Arg Glu Met Ala Val Ile Gly Gly Ser Gly Leu Phe Arg
145                 150                 155                 160

Phe Ala Arg Gly Tyr Val Gln Ala Ser Thr His Ser Trp Asp Phe Lys
                165                 170                 175

Thr Gly Asp Ala Thr Val Gln Tyr Asp Ala Tyr Val Leu His Tyr
            180                 185                 190

<210> SEQ ID NO 30
<211> LENGTH: 190
<212> TYPE: PRT
<213> ORGANISM: Capsicum annuum

<400> SEQUENCE: 30

Met Ala Lys Leu Ile Leu Gln Ile Phe Ser Ile Ser Val Leu Tyr Ser
1               5                   10                  15

Leu Val Ala Phe Pro Ala Thr Gly Glu Glu Asp His Ile Phe Gly Lys
            20                  25                  30

Ser Ile Asn Glu Lys Ser Met Arg Leu Lys Arg Glu Lys Leu Ser His
        35                  40                  45

Phe Arg Phe Tyr Trp His Asp Val Leu Ser Gly Ser Lys Pro Thr Ser
    50                  55                  60

Met Ile Ile Ile Pro Pro Pro Lys Asn Thr Thr Thr Gly Phe Gly Gln
65                  70                  75                  80

```
Met Asn Met Ile Asp Asn Ala Leu Thr Leu Gly Pro Glu Leu Ser Ser
             85                  90                  95

Arg Ile Val Gly Arg Ala Gln Gly Phe Tyr Ala Ala Ser Leu Asn
        100                 105                 110

Asp Val Gly Leu Met Met Val Met Asn Phe Ala Phe Ile Glu Gly Lys
            115                 120                 125

Tyr Asn Gly Ser Thr Phe Thr Ile Leu Gly Arg Asn Pro Val Phe Glu
        130                 135                 140

Lys Val Arg Glu Met Ala Val Ile Gly Gly Ser Gly Leu Phe Arg Phe
145                 150                 155                 160

Ala Arg Gly Tyr Val Gln Ala Ser Thr His Ser Leu Asp Phe Lys Thr
                165                 170                 175

Gly Asp Ala Thr Val Gln Tyr Asp Ala Tyr Val Leu His Tyr
        180                 185                 190
```

<210> SEQ ID NO 31
<211> LENGTH: 190
<212> TYPE: PRT
<213> ORGANISM: Capsicum annuum

<400> SEQUENCE: 31

```
Met Ala Lys Leu Ile Leu Gln Ile Phe Ser Ile Ser Val Leu Tyr Ser
1               5                   10                  15

Leu Val Ala Phe Pro Ala Thr Gly Glu Glu Asp His Ile Phe Gly Lys
            20                  25                  30

Ser Ile Asn Glu Lys Ser Met Arg Leu Lys Arg Glu Lys Leu Ser His
        35                  40                  45

Phe Arg Phe Tyr Trp His Asp Val Leu Ser Gly Ser Lys Pro Thr Ser
    50                  55                  60

Met Ile Ile Ile Pro Pro Pro Lys Asn Thr Thr Thr Gly Phe Gly Gln
65                  70                  75                  80

Met Asn Met Ile Asp Asn Ala Leu Thr Leu Gly Pro Glu Leu Ser Ser
                85                  90                  95

Arg Ile Val Gly Arg Ala Gln Gly Phe Tyr Ala Ala Ser Leu Asn
        100                 105                 110

Asp Val Gly Leu Met Met Val Met Asn Phe Ala Phe Ile Glu Gly Lys
            115                 120                 125

Tyr Asn Gly Ser Thr Phe Thr Ile Leu Gly Arg Asn Pro Val Phe Glu
        130                 135                 140

Lys Val Arg Glu Met Ala Val Ile Gly Gly Ser Gly Leu Phe Arg Phe
145                 150                 155                 160

Ala Arg Gly Tyr Val Gln Ala Ser Thr His Ser Leu Asp Phe Lys Thr
                165                 170                 175

Gly Asp Ala Thr Val Gln Tyr Asp Ala Tyr Val Leu His Tyr
        180                 185                 190
```

<210> SEQ ID NO 32
<211> LENGTH: 187
<212> TYPE: PRT
<213> ORGANISM: Solanum melongena
<220> FEATURE:
<221> NAME/KEY: misc_feature
<222> LOCATION: (187)..(187)
<223> OTHER INFORMATION: Xaa can be any naturally occurring amino acid

<400> SEQUENCE: 32

```
Met Ala Lys Leu Ser Leu Gln Ile Phe Thr Ile Ser Ile Leu Leu Phe
1               5                   10                  15
```

Leu Val Ala Phe Pro Ala Thr Gly Glu Glu Asp Asn Tyr Thr Phe Gly
            20                  25                  30

Lys Ser Ile Asn Lys Lys Ser Met Arg Leu Arg Lys Glu Lys Leu Ser
        35                  40                  45

His Phe Arg Phe Tyr Trp His Asp Val Leu Ser Gly Ser Lys Pro Thr
    50                  55                  60

Ser Met Met Ile Ile Pro Pro Lys Asn Thr Thr Thr Gly Phe Gly
65                  70                  75                  80

Gln Met Asn Met Ile Asp Asn Ala Leu Thr Leu Gly Ala Glu Leu Ser
                85                  90                  95

Ser Lys Ile Val Gly Arg Ala Gln Gly Phe Tyr Ala Ala Ala Ser Leu
            100                 105                 110

Asn Asp Val Gly Leu Met Met Val Met Asn Phe Ala Phe Ile Glu Gly
            115                 120                 125

Lys Tyr Asn Gly Ser Thr Phe Thr Ile Leu Gly Arg Asn Pro Val Phe
    130                 135                 140

Glu Lys Val Arg Glu Met Ala Val Ile Gly Gly Ser Gly Leu Phe Arg
145                 150                 155                 160

Phe Ala Arg Gly Tyr Val Gln Ala Ser Thr His Ser Trp Asp Tyr Lys
                165                 170                 175

Thr Gly Asp Ala Thr Val Lys Tyr Asp Ala Xaa
            180                 185

<210> SEQ ID NO 33
<211> LENGTH: 191
<212> TYPE: PRT
<213> ORGANISM: Solanum tuberosum

<400> SEQUENCE: 33

Met Ala Lys Ile Ile Leu Gln Ile Phe Thr Ile Ser Ile Phe Leu Ser
1               5                   10                  15

Leu Val Ala Phe Pro Ala Thr Gly Glu Glu Asp Thr Tyr Ile Phe Gly
            20                  25                  30

Lys Ser Ile Asn Lys Lys Pro Thr Arg Leu Lys Lys Glu Lys Phe Ser
        35                  40                  45

His Phe Arg Phe Tyr Trp His Asp Ile Leu Ser Gly Ser Lys Pro Thr
    50                  55                  60

Ser Met Met Ile Ile Pro Pro Ser Lys Asn Thr Thr Thr Gly Phe Gly
65                  70                  75                  80

Gln Met Asn Met Ile Asp Asn Ala Leu Thr Leu Gly Pro Glu Leu Ser
                85                  90                  95

Ser Lys Ile Val Gly Arg Ala Gln Gly Phe Tyr Gly Ala Ala Ser Leu
            100                 105                 110

Asn Asp Val Gly Leu Met Met Val Met Asn Phe Ala Phe Ile Glu Gly
            115                 120                 125

Lys Tyr Asn Gly Ser Thr Phe Thr Ile Leu Gly Arg Asn Pro Val Phe
    130                 135                 140

Glu Lys Val Arg Glu Met Ala Val Ile Gly Gly Ser Gly Leu Phe Arg
145                 150                 155                 160

Phe Ala Arg Gly Tyr Val Glu Ala Ser Thr His Ser Trp Asp Phe Lys
                165                 170                 175

Thr Gly Asp Ala Thr Val Gln Tyr Asp Ala Tyr Val Leu His Tyr
            180                 185                 190

<210> SEQ ID NO 34
<211> LENGTH: 652
<212> TYPE: DNA
<213> ORGANISM: Phaseolus vulgaris

<400> SEQUENCE: 34

```
tcctctaacc accaaaacca tggctaccaa attcctctta tcgttccttc tcatctcctg      60
ctatgtcctc tccatctcag gagagaaaga acaggtttc gtgggctcag tagaccctaa     120
gtccttaagc tacaagaaga agcacactct tagccacttc aggttctatt ggcacgaaat    180
cttcagtgga agcaacccct cctcggttag aatcattcca ccacaaccaa agtacagcac    240
aaccaccacc ttcggttcgg tgggagtatt cgacaacgtg ttgaccctag acccgagtt     300 gtactcaaag gttgtgggaa gtgctgaagg gttgtactcc tccacatcac aaaaggagtt    360
tgcccttttg gtgattacga actttgtgtt gaccgaaggg aagtacaatg gtagcaccat    420
cacgttcgtg gggagaagtc ccattgctca aaggtgagg gagatgcctg tggttggtgg    480
cagtggtgtt ttcagatttg ccaggggctt tgttgagtcc aggactctgt cttttgatcc    540
ccaaacgagg aacaacacaa ttgagtacaa cgtctacgtt taccactaat tgttgtgttt    600
tataggatgt taaggagttt gatcattgtt gttgttcttc aaaaaggctg ta            652
```

<210> SEQ ID NO 35
<211> LENGTH: 640
<212> TYPE: DNA
<213> ORGANISM: Phaseolus vulgaris

<400> SEQUENCE: 35

```
acttcctcta accaccaaaa ccatggctac caaattcctc ttatcgttcc ttctcatctc     60
ctgctatgtc ctctccatct caggagagaa agaaacaggt tcgtgggct cagtagaccc    120 taagtcctta agctacaaga agaagcacac tcttagccac ttcaggttct attggcacga    180
aatcttcagt ggaagcaacc cctcctcggt tagaatcatt ccaccacaac caaagtacag    240
cacaaccacc accttcggtt cggtgggagt attcgacaac gtgttgaccc taggacccga    300
gttgtactca aaggttgtgg gaagtgctga agggttgtac tcctccacat cacaaaagga    360
gtttgccctt ttggtgatta cgaactttgt gttgaccgaa gggaagtaca atggtagcac    420
catcacgttc gtggggagaa gtcccattgc tcagaaggtg agggagatgc ctgtcgttgg    480
tggcagtggt gttttcagat ttgccagggg ctttgttgag tccaggactc tggcttttga    540
tccccaaacg aggaacaaca cattgagta caacgtctac gtttaccact aattgttgtg    600
cttttaagga tgttaaggag tttgatcatt gttgttgttc                         640
```

<210> SEQ ID NO 36
<211> LENGTH: 564
<212> TYPE: DNA
<213> ORGANISM: Phaseolus vulgaris

<400> SEQUENCE: 36

```
gaaacaggtt tcgtgggctc agtagaccct aagtccttaa gctacaagaa gaagcacacy     60
cttagccact tcaggttcta ttggcacgaa atcttcagtg gaagcaaccc ctcctcggtt    120
agaatcattc caccacaacc aaagtacagc acaaccacca ccttcggttc ggtgggagta    180
ttcgacaacg tgttgaccct aggacccgag ttgtactcaa aggttgtggg aagtgctgaa    240
gggttgtact cctccacatc acaaaaggag tttgcccttt tggtgattac gaactttgtg    300
ttgaccgaag ggaagtacaa tggtagcacc atcacgttcg tggggagaag tcccattgct    360
```

-continued

```
cagaaggtga gggagatgcc tgtggttggy ggcagtggtg ttttcagatt tgccaggggc    420
tttgttgagt ccaggactct gtcttttgat ccccaaacga ggaacaacac aattgagtac    480
aacgtctacg ttaccacta attgttgtgt tttataggat gttaaggagt ttgatcattg     540
ttgttgttct tcaaaaaggc tgta                                           564
```

<210> SEQ ID NO 37
<211> LENGTH: 189
<212> TYPE: PRT
<213> ORGANISM: Phaseolus vulgaris

<400> SEQUENCE: 37

```
Met Ala Thr Lys Phe Leu Leu Ser Phe Leu Leu Ile Ser Cys Tyr Val
1               5                   10                  15

Leu Ser Ile Ser Gly Glu Lys Glu Thr Gly Phe Val Gly Ser Val Asp
            20                  25                  30

Pro Lys Ser Leu Ser Tyr Lys Lys Lys His Thr Leu Ser His Phe Arg
        35                  40                  45

Phe Tyr Trp His Glu Ile Phe Ser Gly Ser Asn Pro Ser Ser Val Arg
    50                  55                  60

Ile Ile Pro Pro Gln Pro Lys Tyr Ser Thr Thr Thr Thr Phe Gly Ser
65                  70                  75                  80

Val Gly Val Phe Asp Asn Val Leu Thr Leu Gly Pro Glu Leu Tyr Ser
                85                  90                  95

Lys Val Val Gly Ser Ala Glu Gly Leu Tyr Ser Ser Thr Ser Gln Lys
            100                 105                 110

Glu Phe Ala Leu Leu Val Ile Thr Asn Phe Val Leu Thr Glu Gly Lys
        115                 120                 125

Tyr Asn Gly Ser Thr Ile Thr Phe Val Gly Arg Ser Pro Ile Ala Gln
    130                 135                 140

Lys Val Arg Glu Met Pro Val Val Gly Gly Ser Gly Val Phe Arg Phe
145                 150                 155                 160

Ala Arg Gly Phe Val Glu Ser Arg Thr Leu Ser Phe Asp Pro Gln Thr
                165                 170                 175

Arg Asn Asn Thr Ile Glu Tyr Asn Val Tyr Val Tyr His
            180                 185
```

<210> SEQ ID NO 38
<211> LENGTH: 189
<212> TYPE: PRT
<213> ORGANISM: Phaseolus vulgaris

<400> SEQUENCE: 38

```
Met Ala Thr Lys Phe Leu Leu Ser Phe Leu Leu Ile Ser Cys Tyr Val
1               5                   10                  15

Leu Ser Ile Ser Gly Glu Lys Glu Thr Gly Phe Val Gly Ser Val Asp
            20                  25                  30

Pro Lys Ser Leu Ser Tyr Lys Lys Lys His Thr Leu Ser His Phe Arg
        35                  40                  45

Phe Tyr Trp His Glu Ile Phe Ser Gly Ser Asn Pro Ser Ser Val Arg
    50                  55                  60

Ile Ile Pro Pro Gln Pro Lys Tyr Ser Thr Thr Thr Thr Phe Gly Ser
65                  70                  75                  80

Val Gly Val Phe Asp Asn Val Leu Thr Leu Gly Pro Glu Leu Tyr Ser
                85                  90                  95

Lys Val Val Gly Ser Ala Glu Gly Leu Tyr Ser Ser Thr Ser Gln Lys
```

```
              100                 105                 110
Glu Phe Ala Leu Leu Val Ile Thr Asn Phe Val Leu Thr Glu Gly Lys
            115                 120                 125

Tyr Asn Gly Ser Thr Ile Thr Phe Val Gly Arg Ser Pro Ile Ala Gln
        130                 135                 140

Lys Val Arg Glu Met Pro Val Val Gly Gly Ser Gly Val Phe Arg Phe
145                 150                 155                 160

Ala Arg Gly Phe Val Glu Ser Arg Thr Leu Ala Phe Asp Pro Gln Thr
            165                 170                 175

Arg Asn Asn Thr Ile Glu Tyr Asn Val Tyr Val Tyr His
        180                 185

<210> SEQ ID NO 39
<211> LENGTH: 166
<212> TYPE: PRT
<213> ORGANISM: Phaseolus vulgaris

<400> SEQUENCE: 39

Glu Thr Gly Phe Val Gly Ser Val Asp Pro Lys Ser Leu Ser Tyr Lys
1               5                   10                  15

Lys Lys His Thr Leu Ser His Phe Arg Phe Tyr Trp His Glu Ile Phe
            20                  25                  30

Ser Gly Ser Asn Pro Ser Ser Val Arg Ile Ile Pro Pro Gln Pro Lys
        35                  40                  45

Tyr Ser Thr Thr Thr Thr Phe Gly Ser Val Gly Val Phe Asp Asn Val
    50                  55                  60

Leu Thr Leu Gly Pro Glu Leu Tyr Ser Lys Val Val Gly Ser Ala Glu
65                  70                  75                  80

Gly Leu Tyr Ser Ser Thr Ser Gln Lys Glu Phe Ala Leu Leu Val Ile
            85                  90                  95

Thr Asn Phe Val Leu Thr Glu Gly Lys Tyr Asn Gly Ser Thr Ile Thr
            100                 105                 110

Phe Val Gly Arg Ser Pro Ile Ala Gln Lys Val Arg Glu Met Pro Val
        115                 120                 125

Val Gly Gly Ser Gly Val Phe Arg Phe Ala Arg Gly Phe Val Glu Ser
    130                 135                 140

Arg Thr Leu Ser Phe Asp Pro Gln Thr Arg Asn Asn Thr Ile Glu Tyr
145                 150                 155                 160

Asn Val Tyr Val Tyr His
            165

<210> SEQ ID NO 40
<211> LENGTH: 693
<212> TYPE: DNA
<213> ORGANISM: Coffea arabica

<400> SEQUENCE: 40
atggctagaa tttcagcatt tcctctcctc accatcttca tcttcatttc ctgcatcacc      60
gttcaggtca cttatggtga tgaagaatac gagtttgtca agcaattga tccaaaagta     120 gcactaaaga tgaagaaaga aaagctaagc cttttcaggt tctactgca cgacatcctc     180 agtggcaaag cacctacttc agtcatggtg gtgccacctc gaaaaccaa ttcattcact     240 gcttttggcc tggtgaacat gatcgataat cctttaactg tcggcccgga gctcagctca     300
aaattggtcg ggagggctca agggttttat gcatcagctt cacaagagga aattggcttc     360
ttgatgacca tgaactttgc tttcactgaa ggtaagtata atggaagcac cctcaccgtg     420
```

```
ttagggagga atccggtgct caaaaaggtg agggagatgc cggtggtcgg cggaagtggg    480
cttttccgat tgctaatgg ttatgctcag gcatcaaccc acaactttga ccccaagact    540
ggtgatgctg ttgttgagta caacatctat gttatgcatt attgatgatc gtgggattgt    600
tttcccttag atcggact ttttcctttg cttttgtttt cttttttgtct cttggtattt    660 ctgctagaaa ttttgtgggg cataatatat cca                                693
```

<210> SEQ ID NO 41
<211> LENGTH: 693
<212> TYPE: DNA
<213> ORGANISM: Coffea arabica

<400> SEQUENCE: 41

```
atggctagaa tttcagcatt tcctctcctc accatcttca tcttcatttc ctgcatcacc     60
gttcaggtca cttatggtga tgaagaatac gagtttgtca agcaattga tccaaaagta    120 gcactaaaga tgaagaaaga aaagctaagc cttttcaggt tctactgca cgacatcctc    180 agtggcaaag cacctacttc agtcatggtg gtgccacctc cgaaaaccaa ttcattcact    240
gcttttggcc tggtgaacat gatcgataat ccgttaactg ttggcccgga cctcagctca    300
aaattggtcg ggagggctca agggttttat gcatcagctt cacaggagga aattggcttc    360
ttgatgacca tgaactttgc tttcactgaa ggtaagtata atggaagcac cctcaccgtg    420
ttagggagga atccggtgct caaaaaggtg agggagatgc cggtagtcgg cggaagtggg    480
cttttccgat tgctaatgg ttatgctcag gcatcaaccc acaactttga ccccaagact    540
ggtgatgctg ttgttgagta caacatctat gttatgcatt attgatgatc gtgggattgt    600
tttcccttag atcggact ttttcctttg cttttgtttt cttttttgtct cttggtattt    660 ctgctagaaa ttttgtgggg cataatatat cca                                693
```

<210> SEQ ID NO 42
<211> LENGTH: 646
<212> TYPE: DNA
<213> ORGANISM: Capsicum annuum

<400> SEQUENCE: 42

```
aatctacttc catggccaaa ctaatactcc aaatcttctc catttccgtt ctctattcac     60
tggtagcctt tccagccacg ggagaagaag atcatatttt tggaaaatcc ataaatgaaa    120
agtccatgag gctaaaaagg gaaaaactca gccatttcag attttattgg cacgacgtcc    180
tcagtggctc caaaccaaca tctatgataa ttatcccacc tcccaaaaat actaccacag    240
gctttggcca aatgaatatg atagataatg ccctaacctt aggaccagag ctgagttcca    300
ggatagttgg aagggcacaa gggttttacg ctgctgcttc actaaatgat gttggcttaa    360
tgatggtcat gaactttgct tttattgaag gaaaatataa tgggagcacc ttcactatac    420
ttggacgaaa tccggtattt gagaaggtga gagagatggc cgtgatcggc ggcagtgggc    480
ttttccgatt tgctagagga tatgttcagg ctagtactca ttcattggat ttcaaaactg    540
gcgatgctac tgttcagtat gatgcctatg ttttgcatta ttgaagttta ctaatattat    600
atatcactct aatcggctag ctggctttta attaataatt atgtcg                   646
```

<210> SEQ ID NO 43
<211> LENGTH: 194
<212> TYPE: PRT
<213> ORGANISM: Coffea arabica

<400> SEQUENCE: 43

```
Met Ala Arg Ile Ser Ala Phe Pro Leu Leu Thr Ile Phe Ile Phe Ile
1               5                   10                  15

Ser Cys Ile Thr Val Gln Val Thr Tyr Gly Asp Glu Glu Tyr Glu Phe
            20                  25                  30

Val Lys Ala Ile Asp Pro Lys Val Ala Leu Lys Met Lys Lys Glu Lys
        35                  40                  45

Leu Ser Leu Phe Arg Phe Tyr Trp His Asp Ile Leu Ser Gly Lys Ala
    50                  55                  60

Pro Thr Ser Val Met Val Pro Pro Lys Thr Asn Ser Phe Thr
65                  70                  75                  80

Ala Phe Gly Leu Val Asn Met Ile Asp Asn Pro Leu Thr Val Gly Pro
                85                  90                  95

Glu Leu Ser Ser Lys Leu Val Gly Arg Ala Gln Gly Phe Tyr Ala Ser
            100                 105                 110

Ala Ser Gln Glu Glu Ile Gly Phe Leu Met Thr Met Asn Phe Ala Phe
        115                 120                 125

Thr Glu Gly Lys Tyr Asn Gly Ser Thr Leu Thr Val Leu Gly Arg Asn
    130                 135                 140

Pro Val Leu Lys Lys Val Arg Glu Met Pro Val Val Gly Gly Ser Gly
145                 150                 155                 160

Leu Phe Arg Phe Ala Asn Gly Tyr Ala Gln Ala Ser Thr His Asn Phe
                165                 170                 175

Asp Pro Lys Thr Gly Asp Ala Val Val Glu Tyr Asn Ile Tyr Val Met
            180                 185                 190

His Tyr
```

<210> SEQ ID NO 44
<211> LENGTH: 194
<212> TYPE: PRT
<213> ORGANISM: Coffea arabica

<400> SEQUENCE: 44

```
Met Ala Arg Ile Ser Ala Phe Pro Leu Leu Thr Ile Phe Ile Phe Ile
1               5                   10                  15

Ser Cys Ile Thr Val Gln Val Thr Tyr Gly Asp Glu Glu Tyr Glu Phe
            20                  25                  30

Val Lys Ala Ile Asp Pro Lys Val Ala Leu Lys Met Lys Lys Glu Lys
        35                  40                  45

Leu Ser Leu Phe Arg Phe Tyr Trp His Asp Ile Leu Ser Gly Lys Ala
    50                  55                  60

Pro Thr Ser Val Met Val Pro Pro Lys Thr Asn Ser Phe Thr
65                  70                  75                  80

Ala Phe Gly Leu Val Asn Met Ile Asp Asn Pro Leu Thr Val Gly Pro
                85                  90                  95

Asp Leu Ser Ser Lys Leu Val Gly Arg Ala Gln Gly Phe Tyr Ala Ser
            100                 105                 110

Ala Ser Gln Glu Glu Ile Gly Phe Leu Met Thr Met Asn Phe Ala Phe
        115                 120                 125

Thr Glu Gly Lys Tyr Asn Gly Ser Thr Leu Thr Val Leu Gly Arg Asn
    130                 135                 140

Pro Val Leu Lys Lys Val Arg Glu Met Pro Val Val Gly Gly Ser Gly
145                 150                 155                 160

Leu Phe Arg Phe Ala Asn Gly Tyr Ala Gln Ala Ser Thr His Asn Phe
```

```
                     165                 170                 175
Asp Pro Lys Thr Gly Asp Ala Val Val Glu Tyr Asn Ile Tyr Val Met
                 180                 185                 190

His Tyr

<210> SEQ ID NO 45
<211> LENGTH: 190
<212> TYPE: PRT
<213> ORGANISM: Capsicum annuum

<400> SEQUENCE: 45

Met Ala Lys Leu Ile Leu Gln Ile Phe Ser Ile Ser Val Leu Tyr Ser
1               5                   10                  15

Leu Val Ala Phe Pro Ala Thr Gly Glu Glu Asp His Ile Phe Gly Lys
            20                  25                  30

Ser Ile Asn Glu Lys Ser Met Arg Leu Lys Arg Glu Lys Leu Ser His
        35                  40                  45

Phe Arg Phe Tyr Trp His Asp Val Leu Ser Gly Ser Lys Pro Thr Ser
    50                  55                  60

Met Ile Ile Ile Pro Pro Pro Lys Asn Thr Thr Thr Gly Phe Gly Gln
65                  70                  75                  80

Met Asn Met Ile Asp Asn Ala Leu Thr Leu Gly Pro Glu Leu Ser Ser
                85                  90                  95

Arg Ile Val Gly Arg Ala Gln Gly Phe Tyr Ala Ala Ala Ser Leu Asn
            100                 105                 110

Asp Val Gly Leu Met Met Val Met Asn Phe Ala Phe Ile Glu Gly Lys
        115                 120                 125

Tyr Asn Gly Ser Thr Phe Thr Ile Leu Gly Arg Asn Pro Val Phe Glu
    130                 135                 140

Lys Val Arg Glu Met Ala Val Ile Gly Gly Ser Gly Leu Phe Arg Phe
145                 150                 155                 160

Ala Arg Gly Tyr Val Gln Ala Ser Thr His Ser Leu Asp Phe Lys Thr
                165                 170                 175

Gly Asp Ala Thr Val Gln Tyr Asp Ala Tyr Val Leu His Tyr
            180                 185                 190

<210> SEQ ID NO 46
<211> LENGTH: 858
<212> TYPE: DNA
<213> ORGANISM: Zea mays

<400> SEQUENCE: 46
accacacgta cgcccacacc agataataca ctacagcaca gcaccgacaa cacctctcaa      60
gtaacccagc aggcaccatg gccgccgccg tgcccctcct cctcctcctg ctactgccaa    120
cgaccctgat ggccgcgtcg gcggcgtccg gcggcgagaa gagcacgcac atcaagctgt    180
actggcacga cgtggtgagc gggccgagcc cgacggcggt gccggtggcg caggcggcgg    240
tgaccaacac ctccaagacc gccttcggca tggtggtggt gatcgacgac ccgctgaccg    300
agggccccga cctcaagtcc tccaagccgc tcggccgcgc gcagggcacc tacgtcggcg    360
cgggcaagga cgagctctcc ctgatgatga acatgaattt cgtgttccag gccgcgagt    420 acaacggcag caccgtcgcc atcatgggcc ggaacgccgt gttcgacgcc gtccgcgaga    480
tggccgtcgt gggcggcacc ggcgcgttca ggatggcgcg cgggtacgcg caggcccgca    540
cgcacacctt cgacctcaac accggcgacg ccaccgtcga gtacaacctc tacatcaagc    600
```

```
actgctagc tagcccatcg gctttgtgtt tctgattgtt ggtgctcata tatgaacacg    660
atcgaactcc ataattgtct tgtgagctca atttgtgcca ctggcttttg cagttttggt    720 gaaaagaag agggtaatta aaggacgata gcttcggtcg ttgtaagctg acttcgattt    780
aacttgcaca atgattgagg acttaaagaa taaagatagt aatagacttt gtttatctga    840
tcaaaaaaaa aaaaaaa                                                   858
```

<210> SEQ ID NO 47
<211> LENGTH: 761
<212> TYPE: DNA
<213> ORGANISM: Sorghum sp.

<400> SEQUENCE: 47

```
aaaaaaaacc accaccaccc atcgccatgg ccaccaccac gctcttcctc ctcctctgcg     60
ccgccgcggc actcgcatca gcggcagccg ccgccgacga caccgggttc acgaccttca    120
agctctactt ccacgacatc gtggcgggga cgtcgtcccc aaccgcgtg cggatcgcgc    180 aggcggcgtc gtccaacacc tcctccacct ccttcggcgc cgtggtggcc atcgacgacc    240
ctctcaccac ggggcccacg cggtcgtccg gcaccgagat cggccgcgcc cagggcacct    300
acacgttcgc ggaccagacc acgttcggcc tcctcatggt gatgaacttc gtgttcaccg    360
ccggcgacca aacggcagc acgctctcca tcctcggccg gaacgaggtg ctcaccgacg    420
tccgcgagat gagcatcgtc ggcggcagcg gaaagttccg catggccaag ggctatgtcc    480
aggcgcacac cattgattcc ggcgccacca ccggggagac cgtcgtccag tacaccgtca    540
acgtcaagac gccctagcta gcttagttgg tttcttgctc cggccggccg ggggcctgct    600
ggtgctgcca tggcttgttg tattgtgtgc gtctccggca gctttgtaca cacctgcttt    660
tgccgttctt cggtgttagt acatgacatg acatgtggta gattgagatt tcagatcgac    720
tcgatcttca tcactattga gcgggattta tttggatttg c                        761
```

<210> SEQ ID NO 48
<211> LENGTH: 570
<212> TYPE: DNA
<213> ORGANISM: Oryza sativa,

<400> SEQUENCE: 48

```
gagacgacgg cgacgacgac gcacatcaag gtgtactggc acgacgtggt gagcgggccg     60
agcccgacgg cggtgcaggt ggcgagggcg gcgacgacca actcgtcggc gagcttcttc    120
ggcgccgtgg tggtgatcga cgacccgctg acgtcgggcc ccgacctgaa cgcctcgtcg    180
ccggtgggcc gcgcccaggg cacctacgtc agcgccggca aggacacggt ggcgctgctc    240
atgaacatga acttcgtctt ccagtccggc aggtacaacg gcagcaccgt cgccatcatg    300
ggccgcaacg aggtcttcgc cgccgtccgc gagatggccg tcgtcggcgg caccggcgtc    360
ttccggtggg cccgcggcta cgcccaggcc cggacccaca ccttcgacat gaagaccggc    420
gacgccaccg ttgagtacaa cctctacatc aaccactgaa ctagtcatct ttctcatgag    480 ttttttttt acctttcag aaattatgga tttagttaat agttaatttt tacttagcac      540
caaataattg atgattaatc ttgcttggct                                     570
```

<210> SEQ ID NO 49
<211> LENGTH: 528
<212> TYPE: DNA
<213> ORGANISM: Triticum sp.

<400> SEQUENCE: 49

```
aagggaaatc atggcctctg ccgtgctctt cgtcctcctc gccctggcca ccatgcaacc    60
gcagaccgcg tcgtcccaga aggagacgca cctcaaggtg tactggcacg acgtggtgag   120
cggaccggac ccgacgtcag tgccggtggc gcgcgcgacc acgaccaaca cctccaagac   180
agccttcggc gtcgtcatgg tcatggacaa ctcactcacc gaggggccga gcctcaactc   240
atccaggctc atgggccgcg cccagggcac ctacatcgcc gccggcaagg accagctggc   300
gctgctcatg ctcatgaact tccttttcac cgccggcaag tacaacggca gcagcgtcgc   360
cattatgggt cgcaacgccg tgttcaccga ggtccgcgag atggctgtcg tcggcggtac   420
cggcgttttc aggtgggctc agggtacgc gcaggccagg acgcacacct tggacctcaa   480
gaccggcgac gccaccgttg agtacaacgt attcatcatg cactagtc              528
```

<210> SEQ ID NO 50
<211> LENGTH: 732
<212> TYPE: DNA
<213> ORGANISM: Hordeum sp.

<400> SEQUENCE: 50

```
ggactactcg acagaaaatc catggcctct gcagcgctct tctttgtcct cctcgccctg    60
gccacaatgc tgccgcagac cgcgtcgtcc gagaaggaga cgcacctcaa ggtgtactgg   120
cacgacgtgg tgagcggccc gaacccgacg tcggtgccgg tggcgcgtgc ggccacgacc   180
aacacctcca agacagcctt cggcgtcgtc atggtcatcg acaaccccact caccgagggg   240
ggcagcctca actcatccag gctcatgggc gcgcccagg gcacctacat cgccgccggc   300
aaggaccagc tggcgctgct catgctcatg aacttcgtct tcactgccgg cgagtacaac   360
ggcagcagcg tcgccattat gggtcgcaac gccgtgttca ccgaggtccg cgagatggct   420
gtcgtcggcg gtaccggcgt tttcaggtgg gctcgtgggt acgcgcaggc caggacgcac   480
accttggacc tcaagaccgg cgacgccacc gttgagtaca agtattcgt catgcactag   540
tcgtctcggc cgtggtcaca ttttaccagg acttttgtat acactcaagt tacaagaata   600
atttatttat ttttgcggat gaagaataaa tttatttata tgcgttactt acggaaaact   660
tttctcacaa ttcgtgtgtg tgtcattcac aattgatggt gctgccgttt aatattgata   720
ttgtattatt gt                                                      732
```

<210> SEQ ID NO 51
<211> LENGTH: 175
<212> TYPE: PRT
<213> ORGANISM: Zea mays

<400> SEQUENCE: 51

```
Met Ala Ala Ala Val Pro Leu Leu Leu Leu Leu Leu Pro Thr Thr
 1               5                  10                  15

Leu Met Ala Ala Ser Ala Ala Ser Gly Gly Glu Lys Ser Thr His Ile
                20                  25                  30

Lys Leu Tyr Trp His Asp Val Val Ser Gly Pro Ser Pro Thr Ala Val
            35                  40                  45

Pro Val Ala Gln Ala Ala Val Thr Asn Thr Ser Lys Thr Ala Phe Gly
        50                  55                  60

Met Val Val Ile Asp Asp Pro Leu Thr Glu Gly Pro Asp Leu Lys
 65                  70                  75                  80

Ser Ser Lys Pro Leu Gly Arg Ala Gln Gly Thr Tyr Val Gly Ala Gly
                85                  90                  95
```

```
Lys Asp Glu Leu Ser Leu Met Met Asn Met Asn Phe Val Phe Gln Ala
                100                 105                 110
Gly Glu Tyr Asn Gly Ser Thr Val Ala Ile Met Gly Arg Asn Ala Val
            115                 120                 125
Phe Asp Ala Val Arg Glu Met Ala Val Val Gly Gly Thr Gly Ala Phe
        130                 135                 140
Arg Met Ala Arg Gly Tyr Ala Gln Ala Arg Thr His Thr Phe Asp Leu
145                 150                 155                 160
Asn Thr Gly Asp Ala Thr Val Glu Tyr Asn Leu Tyr Ile Lys His
                165                 170                 175
```

<210> SEQ ID NO 52
<211> LENGTH: 176
<212> TYPE: PRT
<213> ORGANISM: Sorghum sp.

<400> SEQUENCE: 52

```
Met Ala Thr Thr Thr Leu Phe Leu Leu Leu Cys Ala Ala Ala Ala Leu
1               5                   10                  15
Ala Ser Ala Ala Ala Ala Asp Asp Thr Gly Phe Thr Thr Phe Lys
            20                  25                  30
Leu Tyr Phe His Asp Ile Val Ala Gly Thr Ser Ser Pro Thr Ala Val
        35                  40                  45
Arg Ile Ala Gln Ala Ala Ser Ser Asn Thr Ser Ser Thr Ser Phe Gly
50                  55                  60
Ala Val Val Ala Ile Asp Asp Pro Leu Thr Thr Gly Pro Thr Arg Ser
65                  70                  75                  80
Ser Gly Thr Glu Ile Gly Arg Ala Gln Gly Thr Tyr Thr Phe Ala Asp
                85                  90                  95
Gln Thr Thr Phe Gly Leu Leu Met Val Met Asn Phe Val Phe Thr Ala
                100                 105                 110
Gly Asp His Asn Gly Ser Thr Leu Ser Ile Leu Gly Arg Asn Glu Val
            115                 120                 125
Leu Thr Asp Val Arg Glu Met Ser Ile Val Gly Gly Ser Gly Lys Phe
        130                 135                 140
Arg Met Ala Lys Gly Tyr Val Gln Ala His Thr Ile Asp Ser Gly Ala
145                 150                 155                 160
Thr Thr Gly Glu Thr Val Val Gln Tyr Thr Val Asn Val Lys Thr Pro
                165                 170                 175
```

<210> SEQ ID NO 53
<211> LENGTH: 152
<212> TYPE: PRT
<213> ORGANISM: Oryza sativa

<400> SEQUENCE: 53

```
Glu Thr Thr Ala Thr Thr His Ile Lys Val Tyr Trp His Asp Val
1               5                   10                  15
Val Ser Gly Pro Ser Pro Thr Ala Val Gln Val Ala Arg Ala Ala Thr
            20                  25                  30
Thr Asn Ser Ser Ala Ser Phe Phe Gly Ala Val Val Ile Asp Asp
        35                  40                  45
Pro Leu Thr Ser Gly Pro Asp Leu Asn Ala Ser Ser Pro Val Gly Arg
    50                  55                  60
Ala Gln Gly Thr Tyr Val Ser Ala Gly Lys Asp Thr Val Ala Leu Leu
65                  70                  75                  80
```

Met Asn Met Asn Phe Val Phe Gln Ser Gly Arg Tyr Asn Gly Ser Thr
                85                  90                  95

Val Ala Ile Met Gly Arg Asn Glu Val Phe Ala Val Arg Glu Met
            100                 105                 110

Ala Val Val Gly Gly Thr Gly Val Phe Arg Trp Ala Arg Gly Tyr Ala
            115                 120                 125

Gln Ala Arg Thr His Thr Phe Asp Met Lys Thr Gly Asp Ala Thr Val
        130                 135                 140

Glu Tyr Asn Leu Tyr Ile Asn His
145                 150

<210> SEQ ID NO 54
<211> LENGTH: 171
<212> TYPE: PRT
<213> ORGANISM: Triticum sp.

<400> SEQUENCE: 54

Met Ala Ser Ala Val Leu Phe Val Leu Leu Ala Leu Ala Thr Met Gln
1               5                   10                  15

Pro Gln Thr Ala Ser Ser Gln Lys Glu Thr His Leu Lys Val Tyr Trp
            20                  25                  30

His Asp Val Val Ser Gly Pro Asp Pro Thr Ser Val Pro Val Ala Arg
        35                  40                  45

Ala Thr Thr Thr Asn Thr Ser Lys Thr Ala Phe Gly Val Val Met Val
    50                  55                  60

Met Asp Asn Ser Leu Thr Glu Gly Pro Ser Leu Asn Ser Ser Arg Leu
65                  70                  75                  80

Met Gly Arg Ala Gln Gly Thr Tyr Ile Ala Ala Gly Lys Asp Gln Leu
                85                  90                  95

Ala Leu Leu Met Leu Met Asn Phe Leu Phe Thr Ala Gly Lys Tyr Asn
            100                 105                 110

Gly Ser Ser Val Ala Ile Met Gly Arg Asn Ala Val Phe Thr Glu Val
            115                 120                 125

Arg Glu Met Ala Val Val Gly Gly Thr Gly Val Phe Arg Trp Ala Pro
        130                 135                 140

Gly Tyr Ala Gln Ala Arg Thr His Thr Leu Asp Leu Lys Thr Gly Asp
145                 150                 155                 160

Ala Thr Val Glu Tyr Asn Val Phe Ile Met His
                165                 170

<210> SEQ ID NO 55
<211> LENGTH: 172
<212> TYPE: PRT
<213> ORGANISM: Hordeum sp.

<400> SEQUENCE: 55

Met Ala Ser Ala Ala Leu Phe Phe Val Leu Leu Ala Leu Ala Thr Met
1               5                   10                  15

Leu Pro Gln Thr Ala Ser Ser Glu Lys Glu Thr His Leu Lys Val Tyr
            20                  25                  30

Trp His Asp Val Val Ser Gly Pro Asn Pro Thr Ser Val Pro Val Ala
        35                  40                  45

Arg Ala Ala Thr Thr Asn Thr Ser Lys Thr Ala Phe Gly Val Val Met
    50                  55                  60

Val Ile Asp Asn Pro Leu Thr Glu Gly Gly Ser Leu Asn Ser Ser Arg
65                  70                  75                  80

Leu Met Gly Arg Ala Gln Gly Thr Tyr Ile Ala Ala Gly Lys Asp Gln
                85                  90                  95

Leu Ala Leu Leu Met Leu Met Asn Phe Val Phe Thr Ala Gly Glu Tyr
            100                 105                 110

Asn Gly Ser Ser Val Ala Ile Met Gly Arg Asn Ala Val Phe Thr Glu
            115                 120                 125

Val Arg Glu Met Ala Val Val Gly Gly Thr Gly Val Phe Arg Trp Ala
        130                 135                 140

Arg Gly Tyr Ala Gln Ala Arg Thr His Thr Leu Asp Leu Lys Thr Gly
145                 150                 155                 160

Asp Ala Thr Val Glu Tyr Lys Val Phe Val Met His
                165                 170

<210> SEQ ID NO 56
<211> LENGTH: 573
<212> TYPE: DNA
<213> ORGANISM: Gossypium hirsutum

<400> SEQUENCE: 56
atggctaaac tttcagaaaa caccctagct gcccacttca tcttcaccat tttcatcgtt      60
tcagctttag ctgaaaacgg cagtagcttc gcgagaacca tggacaagaa ggtgttgggg     120
atgaagaagg aaaagctcag ccactttagg ctatactggc acgacattgt tggcgggaaa     180
aacgcgacgg cggttccggt ggttttccca tcgaggaatt caacgacggc gttcggtatg     240
atcagtgtaa tagacgatcc tttaacgatg agacctgaat taagttcgaa atggtggga      300 agagcacaag ggttttactc ggcggcgtca caacaagaag taggattgtt gatggcgatg     360
aattttgctt ttatggaagg gaaatataat gggagtacga taacgatatt ggggaggaac     420
acggtgtttt caaaggcgag ggaaatgccg gtgatcggcg gtagtggact atttaggttt     480
gctagagggt atgttgaagc tagaacgcat ctttttgatc ctgctactgg tgatgctgtg     540
gttcagtatg attgttatgt tatgcattat tga                                  573

<210> SEQ ID NO 57
<211> LENGTH: 190
<212> TYPE: PRT
<213> ORGANISM: Gossypium hirsutum

<400> SEQUENCE: 57

Met Ala Lys Leu Ser Glu Asn Thr Leu Ala Ala His Phe Ile Phe Thr
1               5                   10                  15

Ile Phe Ile Val Ser Ala Leu Ala Glu Asn Gly Ser Ser Phe Ala Arg
            20                  25                  30

Thr Met Asp Lys Lys Val Leu Gly Met Lys Lys Glu Lys Leu Ser His
        35                  40                  45

Phe Arg Leu Tyr Trp His Asp Ile Val Gly Gly Lys Asn Ala Thr Ala
    50                  55                  60

Val Pro Val Phe Pro Ser Arg Asn Ser Thr Thr Ala Phe Gly Met
65                  70                  75                  80

Ile Ser Val Ile Asp Asp Pro Leu Thr Met Arg Pro Glu Leu Ser Ser
                85                  90                  95

Lys Met Val Gly Arg Ala Gln Gly Phe Tyr Ser Ala Ala Ser Gln Gln
            100                 105                 110

Glu Val Gly Leu Leu Met Ala Met Asn Phe Ala Phe Met Glu Gly Lys
        115                 120                 125

Tyr Asn Gly Ser Thr Ile Thr Ile Leu Gly Arg Asn Thr Val Phe Ser

```
            130                 135                 140
Lys Ala Arg Glu Met Pro Val Ile Gly Gly Ser Gly Leu Phe Arg Phe
145                 150                 155                 160

Ala Arg Gly Tyr Val Glu Ala Arg Thr His Leu Phe Asp Pro Ala Thr
                165                 170                 175

Gly Asp Ala Val Val Gln Tyr Asp Cys Tyr Val Met His Tyr
            180                 185                 190
```

<210> SEQ ID NO 58
<211> LENGTH: 594
<212> TYPE: DNA
<213> ORGANISM: Gossypium hirsutum

<400> SEQUENCE: 58

```
atggctagga ttcctcttct cttagcttcc aaattcatct tcttatccat tttatcctcc    60
tcaggcgtca tccgatgcac ccgaggcgaa aacaatgacg atcatggctt catccagagc   120
cttgaccgag agtcgatggg cttaaaaaaa gaaaagctaa gtcactttcg catctactgg   180
cacgacattg ttagtggccg caatgctacg tcgatacgag tggttcgacc ttctaacgca   240
tcggtaacag ggttcggaat aatcaacatg atcgacaatc cattaacctt agggccgaac   300
ctaagctcga aactagtggg aagagcacaa gggttctacg cactctcgtc acaagaagaa   360
gtgggattgt tgatgtcgat gaactttgct ttcacggaag gaaatacaa tggtagcacg   420
atcacagtgt tggggagaaa cccagttttc aacaaagtga gggaaatgcg ggtgatcgga   480
ggcagcggac ttttccgatt cgcccgaggc tatgttcaag caagaactaa tacattaaac   540
ttgacaaccg gagatgccat tgttgaatac acttgttatg tgatgcatta ttga         594
```

<210> SEQ ID NO 59
<211> LENGTH: 197
<212> TYPE: PRT
<213> ORGANISM: Gossypium hirsutum

<400> SEQUENCE: 59

```
Met Ala Arg Ile Pro Leu Leu Leu Ala Ser Lys Phe Ile Phe Leu Ser
1               5                  10                  15

Ile Leu Ser Ser Ser Gly Val Ile Arg Cys Thr Arg Gly Glu Asn Asn
                20                  25                  30

Asp Asp His Gly Phe Ile Gln Ser Leu Asp Arg Glu Ser Met Gly Leu
            35                  40                  45

Lys Lys Glu Lys Leu Ser His Phe Arg Ile Tyr Trp His Asp Ile Val
50                  55                  60

Ser Gly Arg Asn Ala Thr Ser Ile Arg Val Val Arg Pro Ser Asn Ala
65                  70                  75                  80

Ser Val Thr Gly Phe Gly Ile Ile Asn Met Ile Asp Asn Pro Leu Thr
                85                  90                  95

Leu Gly Pro Asn Leu Ser Ser Lys Leu Val Gly Arg Ala Gln Gly Phe
            100                 105                 110

Tyr Ala Leu Ser Ser Gln Glu Glu Val Gly Leu Leu Met Ser Met Asn
        115                 120                 125

Phe Ala Phe Thr Glu Gly Lys Tyr Asn Gly Ser Thr Ile Thr Val Leu
        130                 135                 140

Gly Arg Asn Pro Val Phe Asn Lys Val Arg Glu Met Arg Val Ile Gly
145                 150                 155                 160

Gly Ser Gly Leu Phe Arg Phe Ala Arg Gly Tyr Val Gln Ala Arg Thr
                165                 170                 175
```

Asn Thr Leu Asn Leu Thr Thr Gly Asp Ala Ile Val Glu Tyr Thr Cys
            180                 185                 190

Tyr Val Met His Tyr
        195

<210> SEQ ID NO 60
<211> LENGTH: 664
<212> TYPE: DNA
<213> ORGANISM: Heliotropium curassavicum

<400> SEQUENCE: 60
gctctaacca ccataatcat ggctaccaaa ttcctcttat cgttcctttt catctcctgc      60
tatgtcctct ccatctcagc agacaaagaa acaggtttcg tgggcccagt tgatcctaag     120
tccgtaagct acaagaagaa gcacacattt agccacttca ggttctattg cacgaaatc     180 ttcagtggaa gcaacccctc ctctgttaga atcgttccac acaaccaaa gtacagcaca     240 accaccacct tcggttctgt gggagtattc gacaacgtgt tgaccctagg acccgagttg     300
tactcaaagg ttgtgggaag tgccgaaggg ttgtactcct ctgcttcaca aaaggagttt     360 gccctttttgg tcattatgaa cttcgcgttg accgaaggga agtacaatgg tagcaccatc     420
acgttcgtgg ggagaagccc catcgctcaa aaggtgagag agatgcctgt aattggtggc     480
accggtgttt tcagatttgc caggggctat gttgagtcct cgaccatcac ctttgatcct     540
caaacgagga acaacacaat tgagtacaac gtctatgttt accactaatt gttgtgtttt     600
gaaggatgtt gaggagtttg atcattgttg ttcttgttgt tcttgaaaaa ggctttagtg     660
tgcc                                                                 664

<210> SEQ ID NO 61
<211> LENGTH: 189
<212> TYPE: PRT
<213> ORGANISM: Heliotropium curassavicum

<400> SEQUENCE: 61

Met Ala Thr Lys Phe Leu Leu Ser Phe Leu Phe Ile Ser Cys Tyr Val
1               5                   10                  15

Leu Ser Ile Ser Ala Asp Lys Glu Thr Gly Phe Val Gly Pro Val Asp
            20                  25                  30

Pro Lys Ser Val Ser Tyr Lys Lys Lys His Thr Phe Ser His Phe Arg
        35                  40                  45

Phe Tyr Trp His Glu Ile Phe Ser Gly Ser Asn Pro Ser Ser Val Arg
    50                  55                  60

Ile Val Pro Pro Gln Pro Lys Tyr Ser Thr Thr Thr Phe Gly Ser
65                  70                  75                  80

Val Gly Val Phe Asp Asn Val Leu Thr Leu Gly Pro Glu Leu Tyr Ser
            85                  90                  95

Lys Val Val Gly Ser Ala Glu Gly Leu Tyr Ser Ser Ala Ser Gln Lys
        100                 105                 110

Glu Phe Ala Leu Leu Val Ile Met Asn Phe Ala Leu Thr Glu Gly Lys
    115                 120                 125

Tyr Asn Gly Ser Thr Ile Thr Phe Val Gly Arg Ser Pro Ile Ala Gln
130                 135                 140

Lys Val Arg Glu Met Pro Val Ile Gly Gly Thr Gly Val Phe Arg Phe
145                 150                 155                 160

Ala Arg Gly Tyr Val Glu Ser Ser Thr Ile Thr Phe Asp Pro Gln Thr
                165                 170                 175

Arg Asn Asn Thr Ile Glu Tyr Asn Val Tyr Val Tyr His
            180                 185

<210> SEQ ID NO 62
<211> LENGTH: 655
<212> TYPE: DNA
<213> ORGANISM: Vigna unguiculata

<400> SEQUENCE: 62
gctctaacca ccataatcat ggctaccaaa ttcctcttat cgttcctttt catctcctgc      60
tatgtcctct ccatctcagc agacaaagaa acaggtttcg tgggcccagt tgatcctaag     120
tccgtaagct acaagaagaa gcacacattt agccacttca ggttctattg gcacgaaatc     180
ttcagtggaa gcaaccccttc ctctgttaga atcgttccac cacaaccaaa gtacagcaca    240
accaccacct tcggttctgt gggagtattc gataacgtgt tgaccctagg acccgagttg     300
tactcaaagg ttgtgggaag tgccgaaggg ttgtactcct ctgcttcaca aaaggagttt     360
gcccttttgg tcattatgaa cttcgcgttg accgaaggga gtacaatgg tagcaccatc      420
acgttcgtgg ggagaagccc catcgctcaa aaggtaagag agatgcctgt gattggtggc     480
accggtgttt tcagatttgc cagggctat gttgagtcct cgaccatcac cttcgatcct      540
caaacgagga caacacaat tgagtacaac gtctatgttt accactaatt gttgtgtttt      600
gaaggatgtt gaggagtttg atcattgttg ttcttgaaaa aggctttagt gtgcc          655

<210> SEQ ID NO 63
<211> LENGTH: 189
<212> TYPE: PRT
<213> ORGANISM: Vigna unguiculata

<400> SEQUENCE: 63

Met Ala Thr Lys Phe Leu Leu Ser Phe Leu Phe Ile Ser Cys Tyr Val
1               5                   10                  15

Leu Ser Ile Ser Ala Asp Lys Glu Thr Gly Phe Val Gly Pro Val Asp
            20                  25                  30

Pro Lys Ser Val Ser Tyr Lys Lys Lys His Thr Phe Ser His Phe Arg
        35                  40                  45

Phe Tyr Trp His Glu Ile Phe Ser Gly Ser Asn Pro Ser Ser Val Arg
    50                  55                  60

Ile Val Pro Pro Gln Pro Lys Tyr Ser Thr Thr Thr Phe Gly Ser
65                  70                  75                  80

Val Gly Val Phe Asp Asn Val Leu Thr Leu Gly Pro Glu Leu Tyr Ser
                85                  90                  95

Lys Val Gly Ser Ala Glu Gly Leu Tyr Ser Ser Ala Ser Gln Lys
            100                 105                 110

Glu Phe Ala Leu Leu Val Ile Met Asn Phe Ala Leu Thr Glu Gly Lys
        115                 120                 125

Tyr Asn Gly Ser Thr Ile Thr Phe Val Gly Arg Ser Pro Ile Ala Gln
    130                 135                 140

Lys Val Arg Glu Met Pro Val Ile Gly Gly Thr Gly Val Phe Arg Phe
145                 150                 155                 160

Ala Arg Gly Tyr Val Glu Ser Ser Thr Ile Thr Phe Asp Pro Gln Thr
                165                 170                 175

Arg Asn Asn Thr Ile Glu Tyr Asn Val Tyr Val Tyr His
            180                 185

```
<210> SEQ ID NO 64
<211> LENGTH: 657
<212> TYPE: DNA
<213> ORGANISM: Gossypium hirsutum

<400> SEQUENCE: 64
cgtgcagaag atggctagga ttcctcttct cttagcttcc aaattcatct tcttatccat      60
tttatcctcc tcaggcgtca tccgatgcac ccgaggcgaa acaatgacg atcatggctt     120 catccagagc cttgaccgag agtcgatggg cttaaaaaaa gaaaagctaa gtcactttcg     180
catctactgg cacgacattg ttagtggccg caatgctacg tcgatacgag tggttcgacc     240
ttctaacgca tcggtaacag ggttcggaat aatcaacatg atcgacaatc cattaacctt     300
agggccgaac ctaagctcga aactagtggg aagagcacaa gggttctacg cactctcgtc     360
acaagaagaa gtgggattgt tgatgtcgat gaactttgct ttcacggaag ggaaatacaa     420
tggtagcacg atcacagtgt tggggagaaa cccagttttc aacaaagtga gggaaatgcg     480
ggtgatcgga ggcagcggac tttccgatt cgcccgaggc tatgttcaag caagaactaa     540
tacattaaac ttgacaaccg gagatgccat tgttgaatac acttgttatg tgatgcatta     600
ttgaatgtgt gacccatttg ctttgcatta ttataaagtt aaatttgctt taatcat       657

<210> SEQ ID NO 65
<211> LENGTH: 594
<212> TYPE: DNA
<213> ORGANISM: Gossypium hirsutum

<400> SEQUENCE: 65
atggctagga ttcctcttct cttagcttcc aaattcatct tcttatccat tttatcctcc      60
tcaggcgtca tccgatgcac ccgaggcgaa acaatgacg atcatggctt catccagagc     120
cttgaccgag agtcgatggg cttaaaaaaa gaaaagctaa gtcactttcg catctactgg     180
cacgacattg ttagtggccg caatgctacg tcgatacgag tggttcgacc ttctaacgca     240
tcggtaacag ggttcggaat aatcaacatg atcgacaatc cattaacctt agggccgaac     300
ctaagctcga aactagtggg aagagcacaa gggttctacg cactctcgtc acaagaagaa     360
gtgggattgt tgatgtcgat gaactttgct ttcacggaag ggaaatacaa tggtagcacg     420
atcacagtgt tggggagaaa cccagttttc aacaaagtga gggaaatgcg ggtgatcgga     480
ggcagcggac tttccgatt cgcccgaggc tatgttcaag caagaactaa tacattaaac     540
ttgacaaccg gagatgccat tgttgaatac acttgttatg tgatgcatta ttga            594
```